United States Patent [19]

Matsumoto et al.

[11] E Patent Number: Re. 33,635

[45] Reissued Date of Patent: Jul. 9, 1991

[54] ENZYMATIC ASSAY METHOD

[75] Inventors: Kunio Matsumoto; Tsutomu Hirata, both of Shizuoka, Japan

[73] Assignee: Toyo Jozo Kabushiki Kaisha, Shizuoka, Japan

[21] Appl. No.: 203,071

[22] Filed: Jun. 6, 1988

Related U.S. Patent Documents

Reissue of:

[64] Patent No.: 4,681,841
Issued: Jul. 21, 1987
Appl. No.: 538,680
Filed: Oct. 3, 1983

[51] Int. Cl.[5] ..... C12Q 1/00; C12Q 1/34; C12Q 1/44; G01N 33/50

[52] U.S. Cl. ..... 435/18; 435/4; 435/14; 435/19; 435/21; 435/22; 435/23; 435/24; 435/25; 435/817

[58] Field of Search ..... 435/4, 14, 18, 19, 21, 435/22, 23, 24, 25, 28, 817

[56] References Cited

U.S. PATENT DOCUMENTS

| | | | |
|---|---|---|---|
| 4,177,109 | 12/1979 | Tohyama et al. | 562/450 |
| 4,209,459 | 6/1980 | Nagasawa et al. | 435/24 |
| 4,384,041 | 5/1983 | Matsumoto et al. | 435/28 |
| 4,472,499 | 9/1984 | McCroskey | 435/4 |
| 4,529,709 | 7/1985 | Takabayashi et al. | 435/24 |

FOREIGN PATENT DOCUMENTS

| | | |
|---|---|---|
| 0108526 | 5/1984 | European Pat. Off. . |
| 3331588 | 3/1984 | Fed. Rep. of Germany . |
| 2103607 | 2/1983 | United Kingdom . |

OTHER PUBLICATIONS

Lin et al., J. Agric. Food Chem., 1981, 29, 253-257.

*Primary Examiner*—Sam Rosen
*Attorney, Agent, or Firm*—Young & Thompson

[57] ABSTRACT

A method for assaying a compound of the formula wherein $R_1$ is hydroxyl or amino, or hydrogen if at least one of $R_2$, $R_3$, $R_4$, $R_5$ and $R_6$ is hydroxyl or amino, and $R_2$, $R_3$, $R_4$, $R_5$ and $R_6$ are hydrogen, halogen, lower alkyl, lower alkoxy, amino, substituted amino, hydroxy, carboxyl or sulfo, or $R_5$ and $R_6$ together form a ring, comprises establishing a reaction system containing the compound to be assayed and a coupler and an enzyme capable of consuming oxygen and generating a pigment in the presence of the compound and the coupler. A detectable change in the reaction system is measured, to assay the compound in question. The measurement can comprise the measurement of consumed oxygen, as by an oxygen electrode. Or the measurement can comprise the measurement of the generated pigment, as by a colorimetric assay at a specific absorption wavelength thereof.

17 Claims, 32 Drawing Sheets

ENZYMATIC ASSAY METHOD

Matter enclosed in heavy brackets [ ] appears in the original patent but forms no part of this reissue specification; matter printed in italics indicates the additions made by reissue.

This invention relates to a method of assaying a compound of the formula

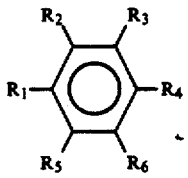

[I]

wherein $R_1$ is hydroxyl or amino, or hydrogen if at least one of $R_2$, $R_3$, $R_4$, $R_5$ or $R_6$ is hydroxyl or amino, and $R_2$, $R_3$, $R_4$, $R_5$ and $R_6$ are hydrogen, halogen, lower alkyl, lower alkoxy, amino, substituted amino, hydroxyl, carboxyl or sulfo, or $R_5$ and $R_6$ together form a ring, which comprises reacting the compound with an oxidase which consumes oxygen and generates a pigment, and measuring at least one of the detectable changes in the reaction system.

The present invention also provides an assay of hydrolase, in which compound [I] is liberated by the action of the hydrolase to be assayed, from a synthetic substrate, which has a component of the structure of compound [I], then oxidizing the thus-produced compound [I] by an oxidase in the presence of a coupler, and measuring the detectable changes.

Enzymatic analysis of a compound in a sample using an enzyme to form a pigment is well known. Most of these methods are assay methods using peroxidase, wherein hydrogen peroxide or phenol, or a compound which generates or liberates the same, is measured.

For example, in an assay of hydrogen peroxide, peroxidase acts in the presence of phenol and a chromogen such as 4-aminoantipyrine, to promote the reaction: $H_2O_2 \rightarrow H_2O + [O]$, in which the phenol and chromogen are oxidatively condensed by the oxidative action of [O] to form a pigment. The amount of hydrogen peroxide can be measured by measuring the absorption at the specific absorption wavelength of the pigment. For example, β-D-glucose forms hydrogen peroxide by the action of glucose oxidase as follows:

$$\beta\text{-D-glucose} + H_2O + O_2 \rightarrow \text{D-gluconate} + H_2O_2$$

The generated hydrogen peroxide is measured and the amount of β-D-glucose can thus be assayed.

This method is the preferred assay method for a reaction system which contains hydrogen peroxide or liberates or generates hydrogen peroxide, and is used in clinical biochemistry.

In the assay of a phenol-series compound, hydrogen peroxide should not be used as a reagent. Since hydrogen peroxide is an unstable compound, assaying a phenol-series compound by this method is not preferred, and in fact is almost unusable.

The enzymatic reaction for forming a pigment other than peroxidase, is that nicotine adenine dinucleotide or nicotine adenine dinucleotide phosphate [NAD(P)] is reduced to NAD(P)H by a dehydrogenase system, and the generated NAD(P) is linked with diaphorase and an electron transfer pigment to form formazane which is then measured by colorimetry. However, this method had disadvantages because the formed formazane is insoluble in water and the pigment adheres to the wall of the container.

We have previously found that p-phenylenediamine or its derivative is oxidized by the action of ascorbate oxidase or laccase to form a pigment, and that leucine aminopeptidase can be assayed by this method. See Japanese Unexam. Pat. Publ. No. 57-115345.

This previous assay method has a number of advantages, such as providing a mild enzymatic assay as compared with chemical methods, and the possibility of automatic rate assay. In this earlier assay method, when a phenol derivative is oxidized by oxidase, the phenol derivative is changed to a compound having an absorption maximum at 350–500 nm.

Quite surprisingly, we have now discovered that a compound of formula [I] and a coupler could be oxidatively condensed by an oxidase such as ascorbate oxidase or laccase, to form a pigment which was previously unknown and which had a different absorption maximum at 500–750 nm.

The compound [I] such as 3,5-dibromo-4-hydroxyaniline does not show color upon reaction with oxidase when a coupler is not used; however, it forms a pigment having an absorption maximum at 600–700 nm by oxidative condensation in the presence of a coupler. This reaction can therefore be considered to proceed by a previously unknown and novel reaction schema.

We have synthesized a synthetic substrate for hydrolase having a component of compound [I], and found that this substrate is hydrolyzed by a corresponding hydrolase to liberate a compound [I] which is changed to a pigment in the presence of a coupler. We have also found that this reaction can be used for the assay of hydrolase.

An object of the present invention is to provide an assay method of a compound [I] which comprises measuring the detectable changes in a reaction system by treating the compound to be assayed with an oxidase which consumes oxygen and generates a pigment in the presence of a coupler.

Another object of the present invention is to provide an assay method of hydrolase which comprises liberating a compound [I] from a synthetic substrate having a component of compound [I] in its structure by the action of hydrolase, treating the thus-produced component with an oxidase which consumes oxygen and generates a pigment in the presence of a coupler, and measuring the detectable changes in the reaction system.

The oxidases are those which consume oxygen and generate a pigment. Examples of the oxidase are ascorbate oxidase, laccase, aminophenol oxidase, polyphenol oxidase and tyrosinase. Preferred examples are ascorbate oxidase obtained from pumpkin, cucumber or chayote (Sechium edule), laccase obtained from a japan (urushi, japanese lacquer), Bacidiomycetes (Coriolus versicolor, Rhizopus or Polyporus versicolor), and tyrosinase. [J. Biochem., 50, 264 (1961), Biochim. Biophys. Acta, 73, 204 (1963), Acta Chem. Scand., 21, 2367 (1967)]. Commercially available enzymes can also be used. These enzymes can be used in the form of immobilized enzymes. The immobilized enzyme can be contacted with an oxygen electrode in an automatic analyzer and the electrochemical changes can be measured. Expensive enzyme can be saved by the use of these electrodes. Furthermore, the sensor, having an enzyme electrode of an immobilized enzyme and an oxygen electrode, can provide an assay method which is rapid, uses less reagent, and can be used for repeated measurements. Also colored specimens can be measured.

The couplers are substances which can oxidatively condense with a compound [I] to form a pigment. In the compound [I] wherein $R_1$ is amino, or hydrogen when at least one of $R_2$, $R_3$, $R_4$, $R_5$ and $R_6$ is amino, and $R_2$, $R_3$, $R_4$, $R_5$ and $R_6$ have the same meanings as hereinbefore (hereinafter called amino compound [I]), the preferred coupler is a compound of the formula

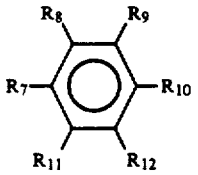

[III]

wherein $R_7$ is hydroxyl, amino or substituted amino $R_8$, $R_9$, $R_{10}$, $R_{11}$ and $R_{12}$ are hydrogen, halogen, lower alkyl, lower alkoxy, amino, substituted amino, hydroxyl, carboxyl or sulfo, or $R_{11}$ and $R_{12}$ together form a ring.

Examples of the coupler for amino compound [I] are phenol, salicylic acid, m-hydroxybenzoic acid, 2,6-dihydroxybenzoic acid, 2-amino-3-hydroxybenzoic acid, 2-hydroxy-5-aminobenzoic acid, p-hydroxybenzoic acid, methyl salicylate, o-methylphenol, m-methylphenol, p-methylphenol, o-methylphenol, m-methoxyphenol, p-methoxyphenol, o-chlorophenol, m-chlorophenol, p-chlorophenol, 2,3-dimethylphenol, 2,4-dimethylphenol, 2,5-dimethylphenol, 2,6-dimethylphenol, 3,5-dimethylphenol, 2,6-dichlorophenol, o-aminophenol, m-aminophenol, p-bromophenol, o-ethylphenol, m-ethylphenol, 2,4-dichlorophenol, 2,4-dibromophenol, 2,6-dibromophenol, 2,6-dibromo-4-aminophenol, 2,6-dichloro-4-aminophenol, 2,6-dimethoxyphenol, 2-methyl-6-chlorophenol, 2-chloro-5-methylphenol, 2-amino-4-chlorophenol, N,N-diethyl-m-aminophenol, 2-amino-4-methylphenol, o-carboxymethylphenol, 2-carboxy-4-aminophenol, 3,4-dihydroxyphenethylamine, α-naphthol, β-naphthol, 4-chloro-1-naphthol, 2-carboxy-1-naphthol, 1-hydroxy-2-naphthoic acid, 1-naphthol-2-sulfonate, 1-naphthol-3-sulfonate, 1-naphthol-4-sulfonate, 1-naphthol-8-sulfonate, 2-naphthol-6-sulfonate, 2-naphthol-7-sulfonate, 2-naphthol-8-sulfonate, 2-naphthol-3,6-disulfonate, 2-naphthol-6,8-disulfonate, N,N-diethyl-m-aminoaniline, N,N-dimethyl-m-aminoaniline, o-carboxyaniline, m-carboxyaniline, o-chloroaniline, m-chloroaniline, m-bromoaniline, o-methylaniline, m-methylaniline, N,N-dimethylaniline, N,N-diethylaniline, N,N-ethyl.ethylhydroxyaniline, N,N-ethyl.ethylhydroxy-m-toluidine, 3-amino-4-chloroaniline and 2-methyl-3-chloroaniline.

In the compound [I] wherein $R_1$ is hydroxyl, or hydrogen when at least one of $R_2$, $R_3$, $R_4$, $R_5$ and $R_6$ is hydroxyl, and $R_2$, $R_3$, $R_4$, $R_5$ and $R_6$ have the same meanings as hereinbefore (hereinafter called phenol compound [I]), the preferred coupler is a compound of the formula

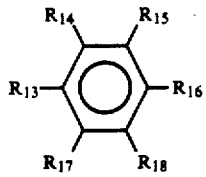

[IV]

wherein $R_{13}$ is amino or substituted amino, and $R_{14}$, $R_{15}$, $R_{16}$, $R_{17}$ and $R_{18}$ are hydrogen, halogen, lower alkyl, lower alkoxy, amino, substituted amino, hydroxyl, carboxyl or sulfo, or $R_{17}$ and $R_{18}$ together form a ring. Examples of couplers for phenol compound [I] are N-ethylaniline, N,N-dimethylaniline, N,N-diethylaniline, N,N-dimethyl-o-toluidine, N,N-dimethyl-p-toluidine, N,N-diethyl-o-toluidine, N,N-diethyl-m-toluidine, N,N-diethyl-p-toluidine, anthranylic acid, p-dimethylaminobenzoic acid, p-chloro-o-toluidine, m-phenylenediamine, p-phenylenediamine, aniline, o-methylaniline, m-methylaniline, o-carboxyaniline, o-chloroaniline, m-chloroaniline, m-bromoaniline, 2-methyl-5-carboxyaniline, N,N-ethyl-hydroxyethylaniline, N,N-dimethyl-m-phenylenediamine, N,N-dimethyl-p-phenylenediamine, N,N-diethyl-p-phenylenediamine, 2-methyl-m-phenylenediamine, 4-methyl-o-phenylenediamine, 4-methyl-m-phenylenediamine, 2-methoxy-5-chloroaniline, 2-ethylaniline, N,N-dimethyl-m-toluidine, 2-chloro-m-phenylenediamine, 2-methyl-3-chloroaniline, 2,5-dimethoxyaniline, 1-amino-5-naphthalenesulfonate, 1-amino-5-naphthalenesulfonate, N,N-ethyl.ethylhydroxy-m-toluidine, 3,5-dibromo-4-hydroxyaniline, 3,5-dichloro-4-hydroxyaniline, o-hydroxyaniline, m-hydroxyaniline, 2-amino-N,N-dimethylaniline, p-N,N-diethylaminoaniline, 2-methyl-3-aminoaniline, 2-methyl-5-aminoaniline, 3-carboxyaniline, 3-carboxy-4-hydroxyaniline and 2-methyl-5-carboxyaniline.

Examples of amino compound [I] are 4-hydroxy-3,5-dichloroaniline, 4-hydroxy-3,5-dibromoaniline, p-N,N-diethylaminoaniline, p-N,N-dimethylaminoaniline, m-phenylenediamine, p-phenylenediamine, o-aminophenol, m-aminophenol, aniline, o-toluidine, m-toluidine, o-carboxyaniline, o-chloroaniline, m-chloroaniline, m-bromoaniline, m-N,N-dimethylaminoaniline, 2-chloro-5-aminoaniline, 2-methyl-3-chloroaniline, 2,5-dimethoxyaniline, 2-methyl-3-aminoaniline, 2-methyl-5-aminoaniline, 2-methyl-5-carboxyaniline, 2-hydroxy-6-carboxyaniline, 2-hydroxy-5-methylaniline, 3-carboxyaniline, 2-carboxy-4-hydroxyaniline, 2-hydroxy-5-chloroaniline, o-ethylaniline, 2-methyl-5-carboxyaniline, 1-amino-6-naphthol-sulfonate and 3-amino-4-chloroaniline.

Examples of phenol compound [I] are 4-amino-2,6-dichlorophenol, 4-amino-2,6-dibromophenol, o-aminophenol, m-aminophenol, p-aminophenol, m-carboxyphenol, p-carboxyphenol, phenol, o-chlorophenol, m-chlorophenol, p-chlorophenol, p-bromophenol, o-ethylphenol, m-ethylphenol, o-methylphenol, m-methylphenol, p-methylphenol, o-methoxyphenol, salicyclic acid, methylsalicylate, o-carboxymethylphenol, m-N,N-diethylaminophenol, 2,4-dichlorophenol, 2,4-dibromophenol, 2,6-dibromophenol, 2,6-dimethoxyphenol, 3,5-dimethylphenol, 2,5-dimethylphenol, 2,4-dimethylphenol, 2,3-dimethylphenol, 2,6-dimethylphenol, 2-methyl-5-chlorophenol, 2-chloro-5-methylphenol, 2-amino-3-carboxyphenol, 2-amino-4-methlylphenol, 2-carboxy-4-aminophenol, 2-amino-4-methylphenol, 2-carboxy-4-aminophenol, 2-amino-4-chlorophenol, α-naphthol, β-naphthol, 4-chloro-1-naphthol, 2-carboxy-1-naphthol, 1-naphthol-2-sulfonate, 1-naphthol-3-sulfonate, 1-naphthol-4-sulfonate, 1-naphthol-8-sulfonate, 2-naphthol-6-sulfonate, 2-naphthol-8-sulfonate, 2-naphthol-3,6-disulfonate, and 8-hydroxy-quinoline-5-sulfonate. Examples of amino compound [I] or phenol compound [I] having both amino and hydroxyl are o-, m- or p-aminophenol, 2-chloro-4-aminophenol, 2-amino-4-carboxyphenol, 2-amino-4-methylphenol, 2-carboxy-4-aminophenol, 2-amino-4-chlorophenol, 2,6-dichloro-4-aminophenol and 2,6-dibromo-4-aminophenol.

Any couplers for amino compound [I] or phenol compound [I] can be used as the aminophenol series compounds hereinabove; however, when the coupler and the aminophenol compound are identical, these combinations of the coupler and the aminophenol compound should be excluded.

In the assay of the compound of formula [I] (hereinafter called compound [I]), a sample containing compound [I] is treated with oxidase which consumes oxygen and generates a pigment in the presence of a coupler [IV]. The amount of coupler used is equimolar or an excess for compound [I], and is an amount having a non-inhibitory action toward the enzyme. These couplers should be prepared for use in constant concentration in a buffer solution of neutral pH, such as Tris-HCl, phosphate, dimethylglutarate-NaOH, acetate, imidazole-HCl, Pipes-NaOH or citrate buffer. The amount of enzyme used is generally (for 0.1-5 ml of 0.1 mM/lit. of compound [I]) ascorbate oxidase 10-1000 units, preferably 50-200 units and laccase or tyrosinase 10-1000 units, preferably 50-500 units. The reaction temperature is about 25°-40° C., preferably about 37° C. The reaction time varies depending on the amount of enzyme used, the temperature and the assay procedure, and is generally more than one minute. Rate assay can preferably be performed in one minute and the other colorimetric assay is preferably performed in 5 minutes.

After the reaction is complete, at least one of the detectable changes is measured, and this is performed by measuring the amount of consumed oxygen or the generated pigment. Oxygen can be measured by electrochemical means such as an oxygen electrode. The amount of oxygen can be measured by colorimetry at 500-750 nm maximum absorption wavelength. The amount of compound [I] in the sample can be measured by calculation from a standard curve.

For the assay of compound [I], a synthetic substrate having a component of that compound [I] in its structure can also be assayed.

The synthetic substrate should be a substrate for hydrolase such as peptidase, protease, amylase, glycosidase, phosphatase, esterase or lipase. Further preferred hydrolases are commercially available enzymes, cultured broths containing enzymes, and specimens such as cells, tissues, urine, saliva and serum. In the present invention, a sample containing the hydrolase is mixed with a corresponding synthetic substrate, and the mixture is incubated at 37° C. to liberate the compound [I]. This compound [I] is treated with an oxidase which consumes oxygen and generates a pigment in the presence of a coupler as hereinbefore, to permit assay of the activity of the enzyme in the sample.

Embodiments of enzyme to be assayed, synthetic substrates and their production are illustrated as follows:

1) Peptidase and protease:

Among the peptidases, aminopeptidase has been known generically as an enzyme which acts on peptide chains to split the amino terminal and liberate amino acids or peptides. Examples of aminopeptidase are cysteine-aminopeptidase (EC: 3. 4. 11. 3), proline aminopeptidase (EC: 3. 4. 11. 5), arginine aminopeptidase (EC: 3. 4. 11. 6), tripeptide aminopeptidase (EC: 3. 4. 11. 4), X-prolyl dipeptidylaminopeptidase (wherein X is an acidic, neutral or basic amino acid residue), and dipeptidase (EC: 3. 4. 13. 11).

Cysteine aminopeptidase (hereinafter called CAP) is found in increased quantity in the blood during an abnormal pregnancy, and an assay of CAP is useful for diagnosis of the placental function and is used for checking a clinical diagnosis during the period of pregnancy.

Synthetic substrate S-benzyl-L-cysteinyl-p-nitroanilide or S-benzyl-L-cysteinyl-N,N-dimethylaminoanilide has been used for that assay. CAP activity is assayed by measuring the yellow color of the p-nitroaniline liberated from substrate S-benzyl-L-cysteinyl-p-nitroanilide. Measuring the yellow color thereof is effected by bilirubin serum or hemolytic serum. Furthermore, liberated p-nitroaniline is chemically reacted with p-dimethylamino cinnamaldehyde to form a red pigment which is measured at 565 nm. This method is impossible to use for rate-assay. Enzymatic activity is also assayed by measuring the blue-green color formed during the reaction of p-dimethylaminoaniline liberated from S-benzyl-L-cystenyl-p-dimethylaminoanilide by the action of CAP and an iron-complex reagent. This method is also impossible to use for rate assay, for chemical reasons.

In the present invention, a synthetic substrate is used, which is a compound having a component of amino compound [I] in its structure, obtained by reacting its amino group with the carboxyl group of an amino acid or peptide.

This synthetic substrate has the formula

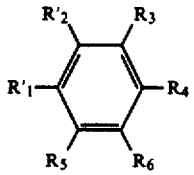

[V]

wherein one of $R'_1$ and $R'_2$ is $R_{19}CO—NH—$ and the other is hydrogen, $R_{19}CO—$ is an amino acid residue or peptide residue, and $R_3$, $R_4$, $R_5$ and $R_6$ have the same meanings as hereinbefore.

Examples of the $R_{19}CO—$ group are S-benzyl-L-cystenyl, L-alanyl and X-prolyl, wherein X is an acidic, neutral or basic amino acid residue.

A sample containing peptidase is reacted with a synthetic substrate of the formula [V] to liberate an amino compound [I] which is subjected to oxidative condensation with a corresponding coupler by oxidase. The resultant mixture is colorimetrically measured at 500-750 nm. The method hereinabove is the preferred method for automatic rate assay.

A synthetic substrate [V] can be produced by conventional peptide synthesis, for example by the condensation of S-benzyl-L-cysteine and an amino compound [I]. S-benzyl-L-cystein can be obtained by the benzylation of the thiol group in L-cysteine. In this synthesis, the functional group is protected if necessary. Protection is performed by any conventional method of peptide synthesis. For example, the α-amino group in L-cysteine is protected by a conventional protective group such as t-butoxycarbonyl, t-amyloxycarbonyl, benzyloxycarbonyl, adamantanyloxycarbonyl or o-nitrophenyl-thionitro-substituted benzyloxycarbonyl. The α-carboxyl group of S-benzyl-L-cysteine, wherein the α-amino group is protected, is activated for example by converting to an acid azide, acid anhydride, acid halogenide, acid imidazolide or activated ester, or by treating with carbodiimide, N,N-carbonyldiimidazole or an isoxazolium salt such as Woodward reagent.

The activated compound is reacted with an amino compound [I], preferably by the carbodiimide, azide, acid halogenide, activated ester or acid anhydride method. The reaction is carried out in an inert solvent such as dimethylformamide, dimethylacetamide dimethylsulfoxide, tetrahydrofuran, benzene, xylene, toluene or diethyl ether at −30° C. to room temperature, generally for 30 minutes to 50 hours, at an equimolar ratio of both compounds. After the reaction is complete, the protective group for the α-amino group is removed. For example, t-butoxycarbonyl is removed by 2N-hydrogen chloride in acetic acid or trifluoroacetic acid, and benzyloxycarbonyl is removed by catalytic hydrogenation using palladium-carbon or hydrogen bromide in acetic acid.

If the amino compound is a liquid, it can be used as the reactive liquid medium, or benzene can be used. The reaction proceeds at 50°–100° C. for 20 minutes to 5 hours.

The thus-obtained synthetic substrate can be purified by conventional extraction, washing, chromatography or otherwise. The product can also be prepared as its salt by reacting with an inorganic acid such as hydrochloric, hydrobromic or phosphoric, or an organic acid such as formic, acetic, propionic, or oxalic.

The enzymatic activity in a specimen such as serum can be assayed by adding a synthetic substrate in a buffer solution, and reacting the liberated amino compound [I] with a coupler in the presence of an oxidase.

X-prolyl-dipeptidyl-aminopeptidase (hereinafter called X-PDAP) wherein X is an amino acid residue, especially glycylprolyl-dipeptidyl aminopeptidase (hereinafter called GPDAP) is a dipeptidylaminopeptidase which hydrolyzes the N-terminal of peptides to liberate glycylproline.

Serum X-PDAP activity increases in acute or chronic hepatitis, hepatocirrhosis or tumor of the bile duct, and decreases in gastric tumor such as stomach cancer or pancreatic tumor. Assaying X-PDAP is useful for the diagnosis of gastric tumor.

Heretofore, synthetic substrates have been used, wherein X is glycine, for example (1) Gly-L-Pro-α-naphthylamide, (2) Gly-L-Pro-p-nitroanilide, (3) Gly-L-Pro-p-phenylazoanilide or (4) 7-(Gly-L-Pro)-4-methylcoumarinamide. For example, an assay method using (1) is a method in which enzymatically-liberated α-naphthylamine is chemically colored by 3-methyl-2-benzothiazolynone hydrazone (MBTH)-$FeCl_3$ and colorimetrically measured. However, α-naphthylamine has carcinogenicity and so is not hygienically safe. The method using (2) is a colorimetric method of measuring liberated yellow-colored p-nitroaniline, and is adversely affected by bilirubin serum or hemolytic serum. Methods using (3) and (4) also have disadvantages.

The present synthetic substrate is a compound wherein the amino group in amino compound [I] is combined with an X-L-prolyl group. Examples of group X are amino acid residues, for example neutral amino acids such as glycine or alanine, acidic amino acids such as aspartic acid or glutamic acid, or basic amino acids such as lysine or arginine. Any type of L-, D- or Dl-amino acid can also be used. A synthetic substrate dipeptide derivative can be used as the free base or as its salt such as p-toluenesulfonate, hydrochloride or hydrobromide. Preferred dipeptide derivatives are compounds wherein X is a neutral or basic amino acid; and dipeptides wherein X is an acidic amino acid are less hydrolyzed.

The present synthetic substrate can be synthesized by any conventional peptide synthesis. For example, the protective group of N-protected-X-prolyl-amino compound [I] is removed. N-protected amino acid-L-prolyl-amino compound [I] is synthesized by reacting an L-prolyl-amino compound [I] with an N-protected amino acid using a condensing reagent such as carbodiimide, or by the activated ester method using an N-protected amino acid having an activated carboxyl group. The protective group can be selected from conventional preferred protective groups, for example benzyloxycarbonyl, t-butyloxycarbonyl, t-amyloxycarbonyl or formyl. The functional side group, if any, is previously protected by any conventional method. For example, the side chain carboxy group in acidic amino acid is protected by a benzyl ester. The guanidino group in arginine is protected by any conventional protective group such as tosyl, nitro, p-nitrobenzyloxycarbonyl or 2-(isopropyloxycarbonyl)-3,4,5,6-tetrachlorobenzoyl, preferably tosyl or nitro. The N-ε-amino group in lysine is preferably protected by any conventional protective group for an α-amino group. The protective group of an N-protected-X-L-prolyl-amino compound [I] is removed by any conventional method. Selective removal of the protective group should be performed. Dipeptide derivatives can also be obtained by a method wherein previously-synthesized N-protected-X-L-proline is condensed with an amino compound [I] to obtain an N-protected-X-L-prolyl-amino compound [I]; then the protective group is removed.

Protease is a general term for enzymes which hydrolyze peptide bonds of peptides and proteins. Examples are pepsin, trypsin, α-chymotrypsin, microbial protease, thrombin, plasmin, plasma kallibrein tissue kallikrein, urokinase, factor Xa, collagenase, elastase or cathepsin.

The diagnostically important proteinases are trypsin and α-chymotrypsin for pancreatic function and protease for the clotting system or fibrinolytic system such as plasmin, thrombin, plasma kallitrein, tissue kallikrein, urokinase or factor Xa.

Heretofore, chromogenic peptide derivatives have been used as synthetic substrates for these assays. For example, the following substrates can be mentioned:

Substrates for thrombin:
Bz-Phe-Val-Arg-p-nitroanilide.HCl,
H-D-Phe-Pro-Arg-p-nitroanilide.HCl,
Tos-gly-Pro-Arg-p-nitroanilide.HCl,
Boc-Val-Pro-Arg-methylcoumarinamide,
H-D-Phe-Pro-Arg-aminoisophthalate dimethyl ester.

Substrates for factor Xa:
Bz-Ile-Glu-Gly-Arg-p-nitroanilide.HCl,
Boc-Ile-Glu-Gly-Arg-methylcoumarinamide.

Substrates for plasma kallikrein:
Bz-Pro-Phe-Arg-p-nitroanilide.HCl,
H-D-Pro-Phe-Arg-p-nitroanilide.2HCl,
Z-Phe-Arg-methylcoumarinamide.

Substrates for plasmin:
H-D-Val-Leu-Lys-p-nitroanilide.2HCl,
Tos-Gly-Pro-Arg-p-nitroanilide.HCl,
Boc-Glu-Lys-Lys-methylcoumarinamide,
Boc-Val-Leu-Lys-methylcoumarinamide,
H-D-Val-Leu-Lys-aminoisophthalate dimethyl ester.

Substrates for urokinase:
Bz-Val-Gly-Arg-p-nitroanilide HCl,
Pyro-Glu-Gly-Arg-p-nitroanilide.HCl,
Glutaryl-Gly-Arg-methylcoumarinamide.

Substrates for tissue kallikrein:
H-D-Val-Leu-Arg-p-nitroanilide.2HCl,
H-Pro-Phe-Arg-methylcoumarinamide.

As for the assay method, liberated p-nitroaniline, aminomethylcoumarin or aminoisophthalate dimethyl ester can be measured by the action of an enzyme in the specimen. In these methods, liberated p-nitroaniline shows a yellow color and is disadvantageously affected by, for example, jaundice color or hemolytic red color. Aminomethylcoumarin or aminoisophthalate dimethyl ester is measured by fluorometry and hence is disadvantageously affected by serum component. In order to avoid these disadvantages, a deproteinization procedure is required. The substrates for trypsin and chymotrypsin are generally acyl-basic amino acid- or acyl-aromatic amino acid-p-nitroanilide. p-Nitroaniline liberated therefrom is measured for assaying these enzymes. Similar disadvantages are found.

In the present invention, a compound of formula [V] hereinbefore, for example an acyl-basic amino acid (peptide having C terminal basic amino acid)-amino compound [I] or an acyl-aromatic amino acid-amino compound, is used as the synthetic substrate, and an amino compound [I] is liberated from this synthetic substrate by the action of trypsin, chymotrypsin or protease (an enzyme acting on the blood clotting system and fibrinolytic system) in the specimen. The liberated amino compound [I] is oxidatively condensed in the presence of a coupler by an oxidase, and the pigment formed is colorimetrically measured. The method is advantageously automated for rate-assay and is not affected by serum components because it has a specific absorption maximum wavelength at 500–750 nm.

Preferred examples of acyl-basic amino acids in synthetic substrates for these enzymes are as follows:

For thrombin:
Bz-Phe-Val-Arg-OH
H-D-Phe-Pro-Arg-OH
Tos-Gly-Pro-Arg-OH
Boc-Val-Pro-Arg-OH
H-D-Pro-Arg-OH For factor Xa:
Bz-Ile-Glu-Gly-Arg-OH
Boc-Ile-Glu-Gly-Arg-OH For plasma kallikrein:
Bz-Pro-Phe-Arg-OH
H-D-Pro-Phe-Arg-OH
Z-Phe-Arg-OH For plasmin:
Tos-Gly-Pro-Arg-OH
Boc-Glu-Lys-Lys-OH
Boc-Val-Leu-Lys-OH
H-D-Val-Leu-Lys-OH For urokinase:
Bz-Val-Gly-Arg-OH
Pyro-Glu-Gly-Arg-OH
Glutaryl-Gly-Arg-OH For tissue kallkrein:
H-D-Val-Leu-Arg-OH
Pro-Phe-Arg-OH Synthetic substrates having these components can also be produced in the same way as illustrated in connection with CAP and GPDAP hereinbefore. An example of synthesis of an amino compound [I] having N,N-diethylamino-p-phenylenediamine is as follows:

Boc-Arg($NO_2$)-OH and N,N-diethylamino-p-phenylenediamine (DEAA) are condensed by a water soluble carbodiimide (WSC) to obtain Boc-Arg($NO_2$)-DEAA. The tert-butyloxycarbonyl group (Boc-) is hydrated by HCl/ethyl acetate to obtain H-Arg($NO_2$)-DEAA. The obtained H-Arg($NO_2$)-DEAA and the amino-group-protected peptides are condensed in the same way as for CAP or GPDAP, for example by dehydration condensation in the presence of WSC in butanol, and the $NO_2$ group is removed by catalytic reduction with palladium/carbon to obtain an acylated basic amino acid-amino compound [I].

The compound [V] can be used for the detection of bacterial endotoxin. Heretofore, trace analysis of bacterial endotoxin using the phenomenon of gelation by amoebocyte lysate of horseshoe crabs and a trace amount of bacterial endotoxin, has been performed.

Recently, endotoxin has been used in clinical pathology. For example, a lymrus amoebocyte lysate test in the surgical field is used for clinical diagnosis of disease findings of exogenous endotoxemia or endotoxin shock caused by diseases showing an apparent infectious nidus. In the field of internal medicine, the effect of intestinal Gram negative bacterial endotoxin on hepatopathy and endogenous endotoxemia, for example the decrease of recticuloendotherial system functions such as detoxication of bacterial endotoxin in the liver, are a problem. For these purposes, the clinical determination of endotoxin on blood clotting, the fibrinolystic system, the kinin system, the circulatory system and the immune system has become important.

In the assay of the above bacterial endotoxin, specimens such as the patient's body fluids, especially blood, ascites, urine, pancreatic juice, liquor cerebrospinalis or bile, are used. These body fluids, however, have their own color, and these colors and the pigments caused by diseases such as the jaundice deep yellow color and the hemolytic red color, inhibit colorimetry. Furthermore, body fluids contain fluorescent substances and hence fluorometry may be inhibited.

In the present assay method, a synthetic substrate of compound [V] wherein $R_{19}CO$— is $R'_{19}$-Gly-Arg, in which $R'_{19}$ is an L-amino acid residue or a peptide residue having a protected N-terminal, and amoebocyte lysate and/or an enzyme precursor isolated therefrom, are reacted with a specimen containing bacterial endotoxin to liberate an amino compound [I]. The amino compound [I] is oxidatively condensed with a coupler by oxidase to colorimetrically assay the endotoxin. The said colorimetric assay can be carried out at 500–750 nm and is preferred for rate assay in an automatic analysis without being inhibited by contaminants in the specimen serum.

Amoebocyte lysate can be obtained by the hypotonic treatment of amoebocytes in the lymphocytes of horseshoe crabs, or as a commercial product (LAL-test; lymus amoebocyte lysate test). Commercially available products are, for example Pregel (Difco Lab., U.S.A.) and Pyrogent (Mallinckrodt Inc., U.S.A.)

The isolation and purification of the enzyme precursor can be effected by treating an amoebocyte lysate by column chromatography, electrophoresis, electrofocusing or affinity chromatography.

The amoebocyte lysate or the enzyme precursor separated therefrom is activated by bacterial endotoxin to form an active enzyme which acts specifically on a peptide of synthetic substrate [V], wherein $R'_{19}$ is, for example Boc-Leu-, Boc-Val-Leu-, Boc-Ser-, Boc-Val-Ser-, Bz-Leu-, Bz-Val-Leu-, Bz-Ser- or Bz-Val-Ser-. Synthesis of the substrate can be performed by the same method as illustrated for the protease hereinbefore.

(2) Sugar hydrolase (amylase, glycosidase):

Examples of sugar hydrolase are amylase, dextranase (EC: 3.2.1.11), cellulase (EC: 3.2.1.4) and glycosidase.

Amylase can be classified as α-amylase (EC: 3.2.1.1), β-amylase (EC: 3.2.1.2) or γ-amylase (EC: 3.2.1.3). α-amylase splits the α[1→4]-linkage between the glucose moiety in starch or lower a polymerized glucose and the oligomer. The said enzyme is originally produced in the pancreas and salivary gland, and increases due to acute pancreatitis. Assaying α-amylase is therefore an important clinical diagnostic procedure.

Various methods of assaying amylase activity are known. The blue starch method is a widely used method in which the blue color liberated by amylase action is colorimetrically assayed. In this method, the substrate is insoluble in water and filtration is essential for colorimetry but is undesirable for an automatic procedure. Furthermore, an assay method using a synthetic substrate for amylase is known. This latter method comprises reacting a synthetic substrate p-nitrophenylmaltopentaoside with α-amylase, liberating p-nitrophenyl by action of α-glucosidase and measuring the same by colorimetry. But this method is disadvantageous for assaying serum amylase because the reaction mixture is yellow, like bilirubin serum or hemolyzate. Another method, in which a synthetic substrate comprising 2,5-dichlorophenylmaltopentaoside is reacted with α-amylase, and further is treated with α-glycosidase and β-glycosidase to liberate 2,4-dichlorophenol which is oxidatively condensed with 4-aminoantipyrine by sodium periodate, with measurement of the absorbency at 500 nm, is known. This method is also disadvantageous because it is impossible to use in an automatic assay system.

The present invention is an improved assay method which is also advantageous for automatic rate assay.

In the amylase assay of the present invention, a synthetic substrate is used which is prepared by condensing a hydroxyl group of a malto-oligosaccharide and a phenolic hydroxyl group of a phenol compound [I]. The synthetic substrate is hydrolyzed by amylase at the malto-oligosaccharide moiety to liberate the phenol compound [I] in combination with glucoside, maltoside or maltopentaoside, which is treated with α- and β-glucosidase to form the phenol compound [I]. The liberated phenol compound [I] is measured colorimetrically.

Malto-oligosaccharides used in the present invention include saccharides consisting of 2–10 D-glucose with an α-1,4-glucoside bond. Examples are maltose, maltotriose, maltotetraose, maltopentaose and maltohexaose. Maltotetraose, maltopentaose and maltohexaose of the formula [VI] hereinbelow are preferred.

Examples of phenol compound [I] are compounds having α- or β-linkage with malto-oligosaccharide or its reduced terminal, which are easily hydrolyzed by α-glucosidase or β-glucosidase and are easily measurable. The said phenol compound [I] includes aminophenol series compounds as set forth hereinbefore.

The synthetic substrate of the present invention is a compound of the formula

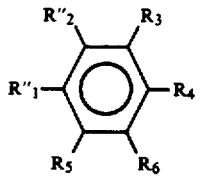

[VI]

wherein one of $R''_1$ and $R''_2$ is (S)n-O- and the other is hydrogen, S is a monosaccharide unit, n is an integer greater than one, and $R_3$, $R_4$, $R_5$ and $R_6$ having the same meanings as hereinbefore. A compound wherein (S) is a glucose moiety and n=2–8 to preferred.

The synthetic substrate [VI] is prepared by the conventional synthetic method with a malto-oligosaccharide. For example, a malto-oligosaccharide is acetylated, and acetyl maltooligosaccharide is condensed with phenol compound [I], then the resulting compound is deacetylated to prepare the product. [Experimental Chemistry, Vol. 24, p. 304 (1958), in Japanese].

Compound [VI] can also be obtained by the enzymatic reaction of phenol compound [I]-α-D-glucoside having one glucosyl group and maltodextrin by cyclomaltodextrin-gluconotransferase; EC: 2.4.1.19. [Wallenfels et al., Carbohydrate Res., 61, 359 (1978)]. By this method, a compound [VI] wherein n=2–8 is obtained which is purified by any conventional method.

Serum amylase is assayed by incubating the enzyme and a synthetic substrate, and α-glucosidase, if required with β-glucosidase, in a buffer solution, and measuring the thus-liberated phenol compound [I] with a coupler and an oxidase.

Examples of glucosidase to be assayed are α-glucosidase (EC: 3.2.1.20), β-glucosidase (EC: 3.2.1.21), α-galactosidase (EC: 3.2.1.22), β-galactosidase (EC: 3.2.1.23), α-mannosidase (EC: 3.2.1.24), β-mannosidase (EC: 3.2.1.25), β-glucuronidase (EC: 3.2.1.31), β-xylosidase (EC: 3.2.1.37), α-L-fusocidase (EC: 3.2.1.51), α-N-acetylgalactosaminidase (EC: 3.2.1.49), α-N-acetylglucosaminidase (EC: 3.2.1.50), β-N-acetylgalactosaminidase (EC: 3.2.1.53), and β-N-acetylglucosaminidase (EC: 3.2.1.30).

Their enzymatic activity can be measured by using a synthetic substrate [VI] wherein the monosaccharide moiety [S] is a pentose, hexose, hexosamine or uronic acid unit, and n=1. For example, a pentose unit such as a xylose unit, a hexose unit such as glucose unit, a galactose unit, a mannose unit or a fucose unit, a hexosamine unit such as an N-acetylgalactosamine unit or an N-acetylglucosamine unit and a uronic acid unit such as glucuronic acid can be mentioned. Glucosidase can be assayed by liberating a phenol compound [I] from a synthetic substrate by the action of the corresponding glucosidase, and measuring the phenol compound [I] with a coupler and an oxidase. For example, a commercially available substrate for glucosidase, phenyl-β-D-glucoside, is contacted with a sample containing glucosidase in a suitable buffer at 37° C., and liberated phenol is converted to a coloring substance with the corresponding coupler and oxidase.

(3) Phosphatase:

Phosphatase is an enzyme which catalyzes the hydrolysis of phosphate esters, and undergoes not only hydrolysis but also a reversible reaction, the direction of the reaction depending on the relative concentration of substrate and product.

In the human body, many phosphate ester compounds are known. The phosphatases which participate in the metabolism of these phosphate esters are classified according to the bond site of the substrate, i.e:

(1) phosphomonoesterase;
(2) phosphodiesterase;
(3) pyrophosphatase;
(4) metaphosphatase;
(5) polyphosphatase;
(6) phosphoamidase.

In clinical tests, phosphomonoesterase is used. Phosphomonoesterase hydrolyzes nonspecifically phenylphosphate, p-nitrophenylphosphate or β-glycerosphosphate. In general, the enzyme having optimum pH on the alkaline side is designated as alkaline phosphatase (EC: 3.1.3.1) (hereinafter called AlP) and that on the acidic side is called acid phosphatase (EC: 3.1.3.2) (hereinafter ACP).

Most AlP originates from the bones, liver, placenta, small intestine or mucosa; and since it is mainly located in the cell membranes, the enzyme participates in active transport through membranes, namely, metabolism.

Diseases is which serum AlP increases are known, such as rachitis, osteomalacia, diaclasis, hepatopathy, cholangitis or tumor, and the assay of serum AlP is important for clinical diagnosis of these maladies. Serum ACP assay is mainly used for the diagnosis of prostatic cancer, and is said to show some effect on the metastasis of mammary cancers.

Heretofore, phosphatase has been assayed by a method of measuring liberated phosphate after hydrolysis of an organic phosphate ester, and a method of measuring liberated phenol from a substrate which is an organic phosphate ester of a phenol.

But the method measuring phosphate is disadvantageous, because coexisting phosphate in the specimen is simultaneously measured and so inorganic phosphates in sample have to be measured and eliminated. Furthermore, the reaction time is very long, and deproteination is required.

A method measuring phenols, the Kind-King method, is that a substrate comprising phenyl phosphate is hydrolyzed to liberate phenol, and the liberated phenol is oxidatively condensed with 4-aminoantipyrine in the presence of potassium ferricyanate to form red-colored quinone which is colorimetrically measured. A modified Kind-King method is that a borate buffer is used for stabilizing the coloring. Furthermore, the method using an alkaline salt of an aromatic sulfonehalogenamide such as Chloramine T etc. in place of potassium ferricyanide (Jap. Pat. Unexam. Publ. No. 52-155597) or using hydrogen peroxideperoxidase has also been proposed. In these methods, potassium ferricyanate is a cyanide compound which causes polution, and they are not advantageous for rate assay; and moreover, the hydrogen peroxide is unstable.

Another method is known, namely, the Bessey-Lowry method or Huggins-Talalay method, in which a substrate comprising p-nitrophenyl phosphate or phenylphthalein phosphate is reacted with a sample containing phosphomonoesterase, and the liberated p-nitrophenol or phenolphthalein is colorimetrically measured under alkaline conditions. But this method has disadvantages due to being affected by bilirubin and hemoglobin in the blood.

Likewise, a further method, in which naphthol liberated from a substrate α-naphthyl phosphate is measured at 340 nm, has disadvantages such as the effect of contaminants in the sample and the carcinogenicity of α-naphthol.

In the present invention, there is used a synthetic substrate for assaying phosphate, of the formula

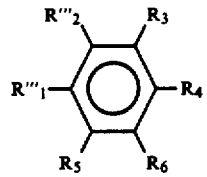

[VII]

wherein one of $R'''_1$ and $R'''_2$ is

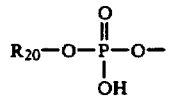

and the other is hydrogen, $R_{20}$—O— is HO— or a substituted or unsubstituted glycerol residue, and $R_3$, $R_4$, $R_5$ and $R_6$ have the same meanings as hereinbefore.

In case the group $R_{20}$—O— is an HO— group, phenol compound [I] is liberated from the said synthetic substrate by the enzymatic action of the phosphomonoesterase in the sample, and the phenol compound [I] is colored with a corresponding coupler and oxidase to measure phosphomonoesterase activity.

Examples of synthetic substrates [VII] can be compounds bound with phenol compound [I] and a mono- or diglyceride phosphate or phosphoric acid, and glycerophosphate or a fatty acid ester substituent thereof. Examples of phenol compound [I] are mentioned hereinbefore. Compound [VII] can be synthesized by any conventional synthetic method using phenol compound [I] and phosphoric acid, or glycerophosphate or a fatty acid ester substituent thereof, or a commercially available reagent can also be used. Enzymatic activity can be assayed in a suitable buffer at 37° C. by contacting a sample containing phosphomonoesterase with a synthetic substrate, liberating the phenol compound [I] and measuring the same by a method as set forth hereinbefore.

As enzymes in phosphodiesterase can be mentioned phospholipase C (EC: 3.1.4.4) and phospholipase D (EC: 3.1.4.4). The synthetic substrate therefor is a compound [VII] wherein $R_{20}$—O— is a substituted or unsubstituted glycerol residue. Examples of substituted glycerol residue are mono- and di-substituted fatty acid esters of glycerol. These synthetic substrates can also be used in the same way as in phosphomonoesterase. Phenol compound [I] is rapidly liberated in the case of phospholipase D; however, in the case of phospholipase C, it can be liberated when phosphatase is used jointly with phospholipase C.

(4) Esterase and lipase:

Esterase is an enzyme which hydrolyzes esters of fatty acids and alcohols, or synthesizes the same. An enzyme which hydrolyzes esters of lower fatty acids and monohydric alcohols is called esterase in its narrow meaning; and an enzyme which hydrolyzes fatty acid to three molecules of an ester of a higher fatty acid and the trihydric alcohol glycerol, is called lipase.

Examples of such enzymes are lipase in the pancreatic juice or caster oil, and esterase in the liver, stomach or serum. Lipase is known as an important enzyme for the diagnosis of pancreatitis in clinical biochemistry.

Hitherto-known assay methods of esterase and lipase are that a fatty acid ester is used as the substrate and enzymatically liberated fatty acid is measured by titration. This method has disadvantages, for example resulting from the high value in titration, and complex operation, and is unsuitable for the assay of many samples. Hence a simple colorimetric assay method has been desired.

A colorimetric assay using synthetic substrate p-nitro phenol acetate, p-nitrophenol laurylate or p-nitrophenol palmitate is one in which enzymatically-liberated p-nitrophenol is measured. This method has disadvantages because of the yellow color of the medium, which is affected by pigment (jaundice serum or hemolysate) in the specimen.

Another method using synthetic substrates, for example fatty acid esters of phenol, α-naphthol or β-naphthol such as phenol laurylate, β-naphthol laurylate or α-naphthyl palmitate, and measuring enzymatically liberated phenol, α- or β-naphthol, is known. Phenol is measured by the colorimetric method of Folin-Ciocalteau. But this method is quite complex and consumes much time and so is almost never used.

A further method is known, in which α-naphthol is reacted with Fast Violet B under alkaline conditions and the thus-formed red color of the diazonium salt is changed to colorless by 2% Triton X-100 solution and is colorimetrically measured at 520 nm. β-naphthol is bound with tetrazo-orthoanisidine to form a red colored insoluble pigment which is extracted with ethyl acetate to measure the same colorimetrically. These methods are, however, complex methods, and are dangerous due to the carcinogenicity of the naphthol.

The present assay method is one in which an ester compound of a fatty acid and a phenol compound [I] is used as the synthetic substrate. The said substrate has the formula

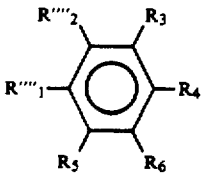

[VIII]

wherein one of $R''''_1$ and $R''''_2$ is $R_{21}$—CO—O— and the other is hydrogen in which $R_{21}$CO— is a fatty acid residue, and $R_3$, $R_4$, $R_5$ and $R_6$ have the same meanings hereinbefore. The said synthetic substrate is hydrolyzed by esterase or lipase in the sample to liberate phenol compound [I], which is oxidatively condensed with a coupler by oxidase. The method is preferred for automatic analysis during rate assay and without affecting the contaminant in the serum due to measuring at long wavelength at 500–750 nm. The synthetic substrate can be synthesized by any conventional method or can be obtained commercially.

Examples of fatty acids are acetic acid, propionic acid, butyric acid, valeric acid, caproic acid, enanthic acid, caprylic acid, pelargonic acid, capric acid, undecylic acid, lauric acid, tridecanic acid, myristic acid, pentadecanoic acid and palmitic acid. Conventional synthesis methods can be used.

In an assay, it is preferable that a buffer solution be used. The amount of the synthetic substrate depends upon the amount of the sample, the enzymatic activity and the reaction time and is generally 0.1–20 mM/lit. and 0.01–5 ml. The enzymatic reaction is carried out at approximately 37° C. for a sufficient time to liberate amino compound [I] or phenol compound [I], usually more than one minute.

Amino compound [I] or phenol compound [I] can be measured by the method hereinbefore described. The enzymatic reaction for liberating the compound [I] from the substrate, and the measurement for the compound [I], can be performed either separately or preferably in one step by adding previously the necessary reagents and enzyme.

Furthermore, consumed oxygen can be measured by an oxygen electrode, and automatic rate assay or other colorimetry can be used.

The reagents and oxidase used in the enzymatic assay can be in liquid form, immobilized form or can be layered on a film or filter paper. Non-ionic surface active agents for solubilization and increasing the hydrophilic nature of the synthetic substrate and other stabilizers for oxidase can optionally be added.

Abbreviations used hereinbelow:

2,6-dibromo-4-aminophenol: 2,6-DBAP

N,N-diethyl-p-phenylenediamine: N,N-DEPD

Figure 5:
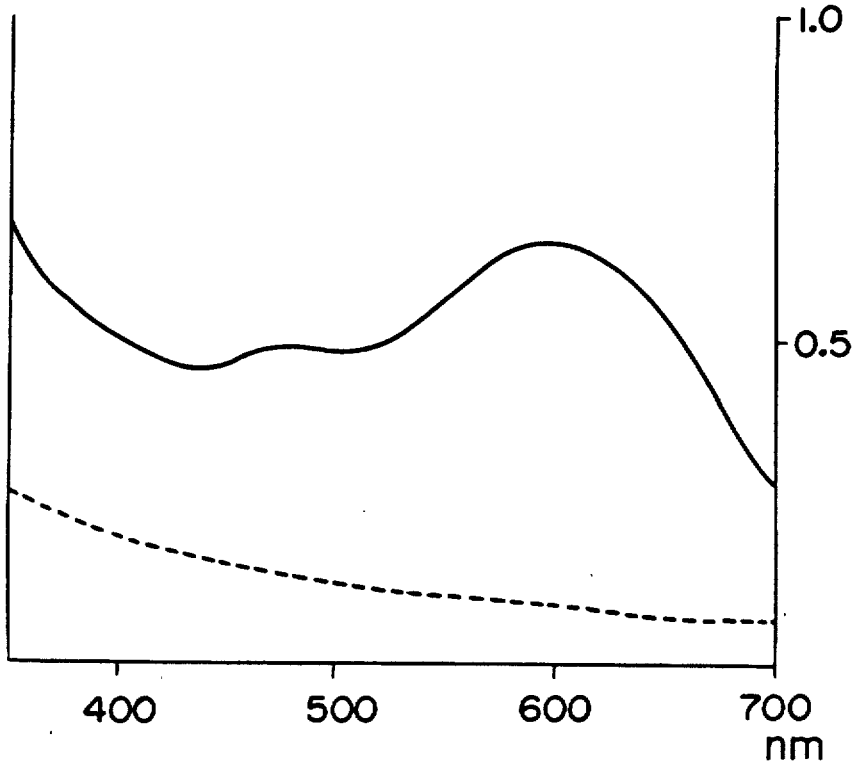
FIGS. 5 through 52 show the absorption curves (solid line) of pigments indicated in each numbered figure according to the following abbreviations.
Figure 6:
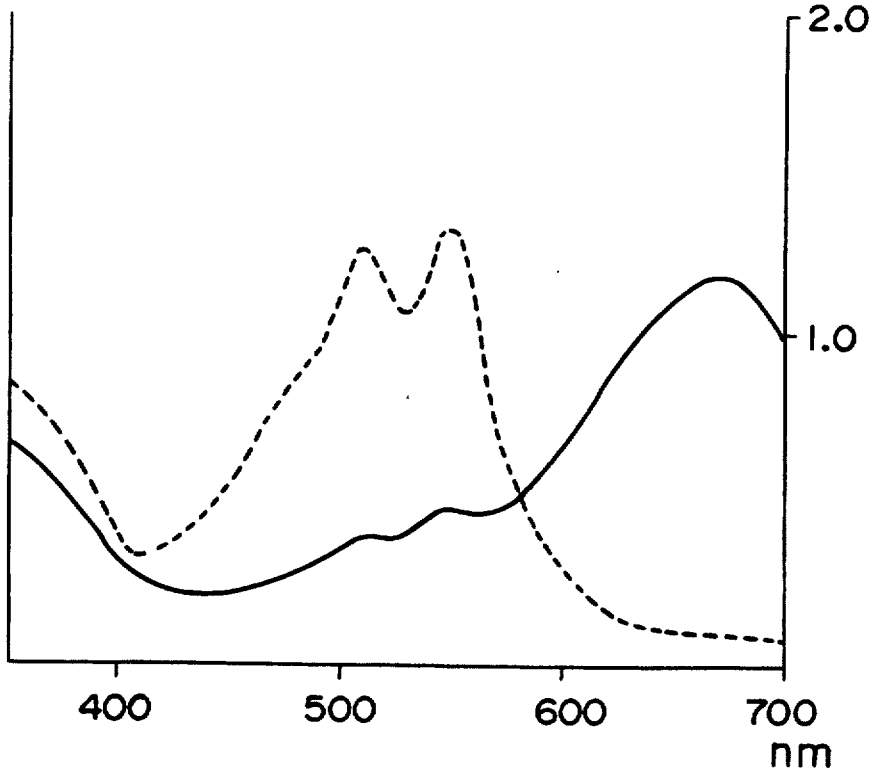
Figure 7:
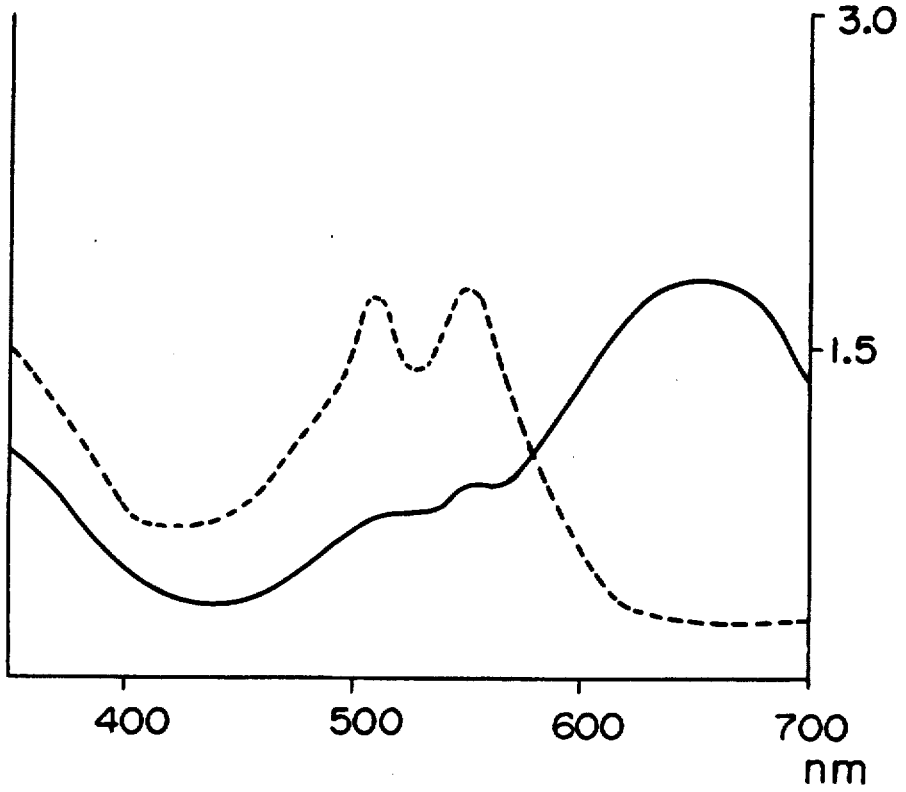
Figure 8:
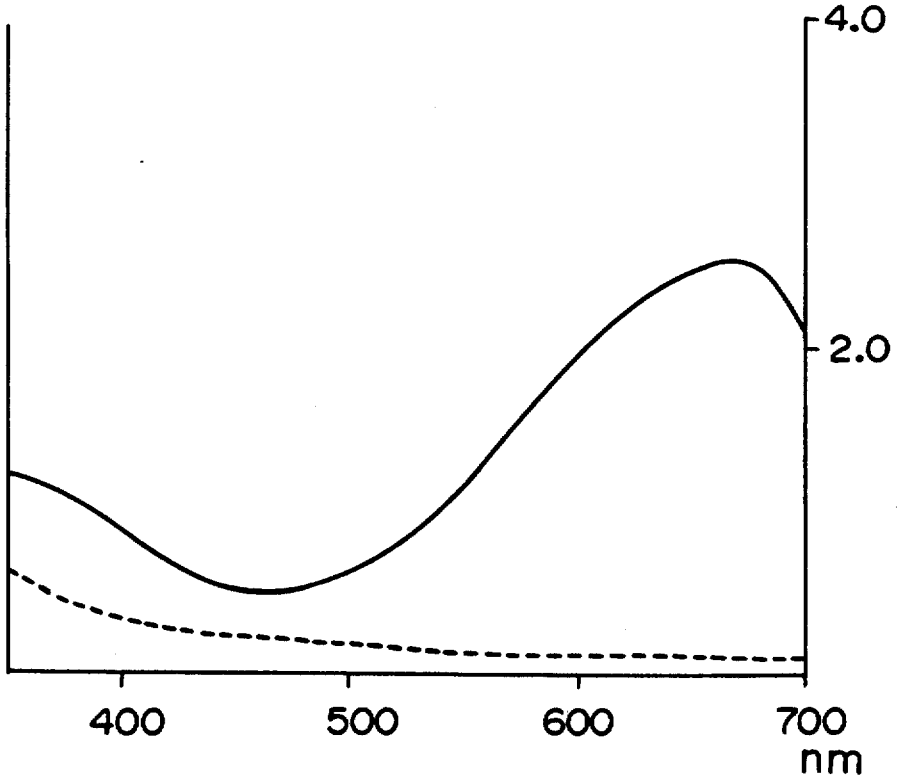
Figure 9:
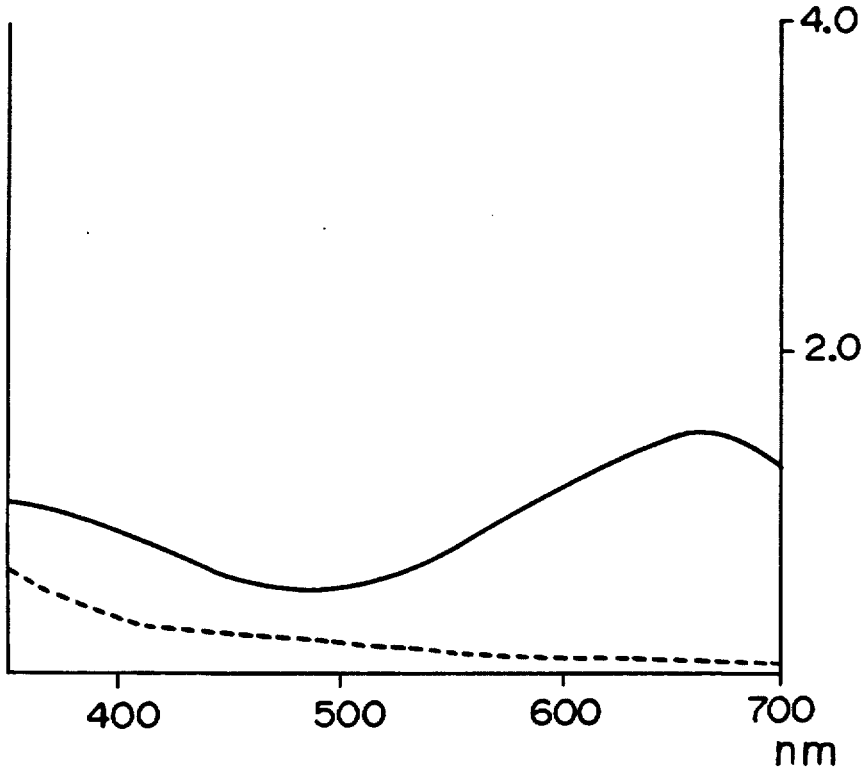
Figure 10:
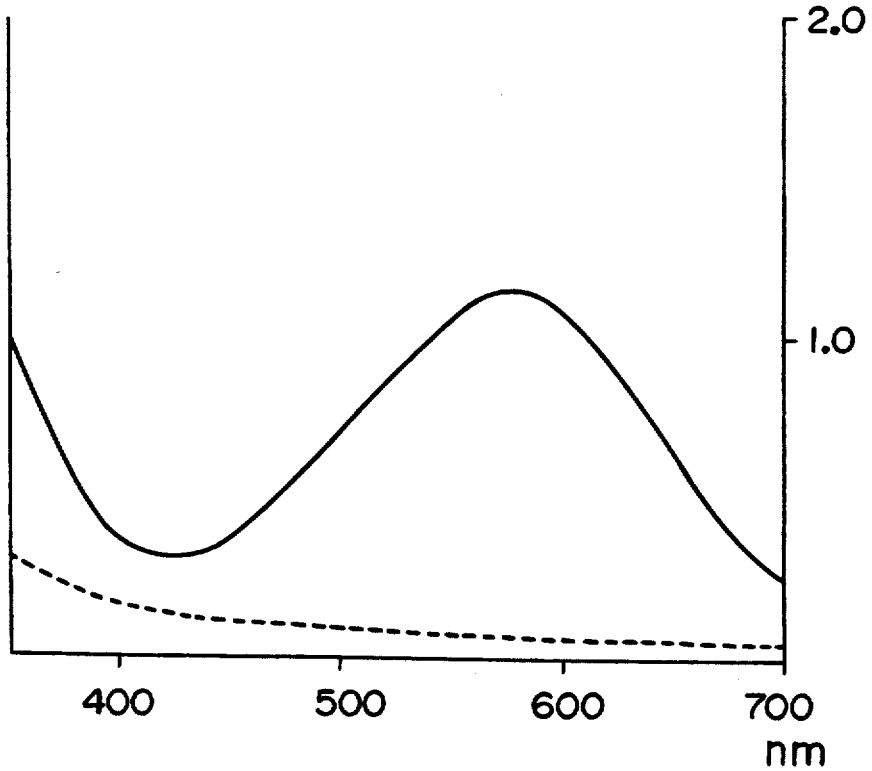
Figure 11:
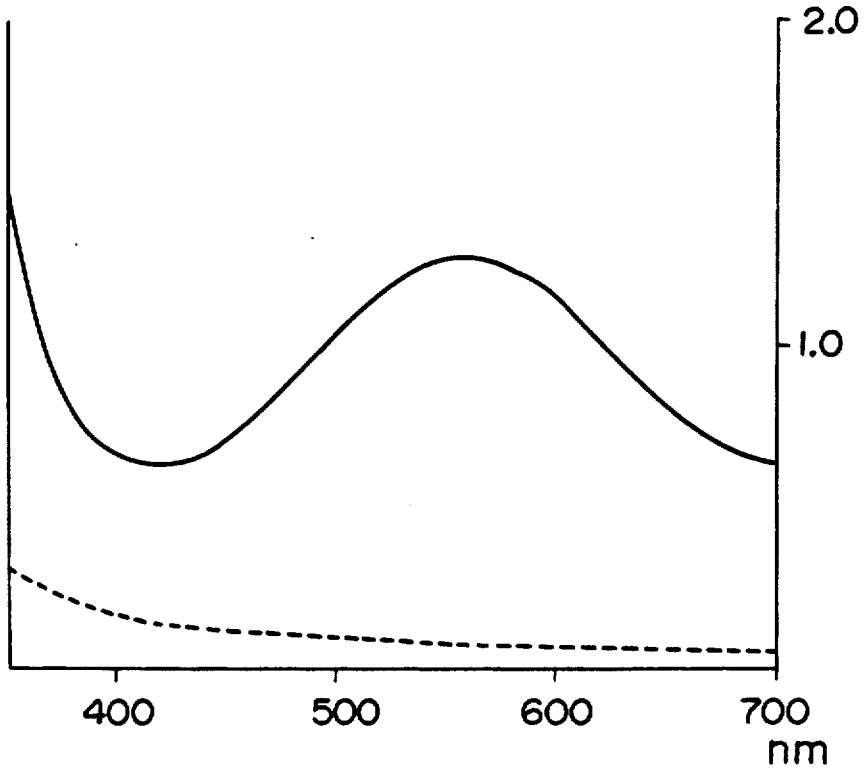
Figure 12:
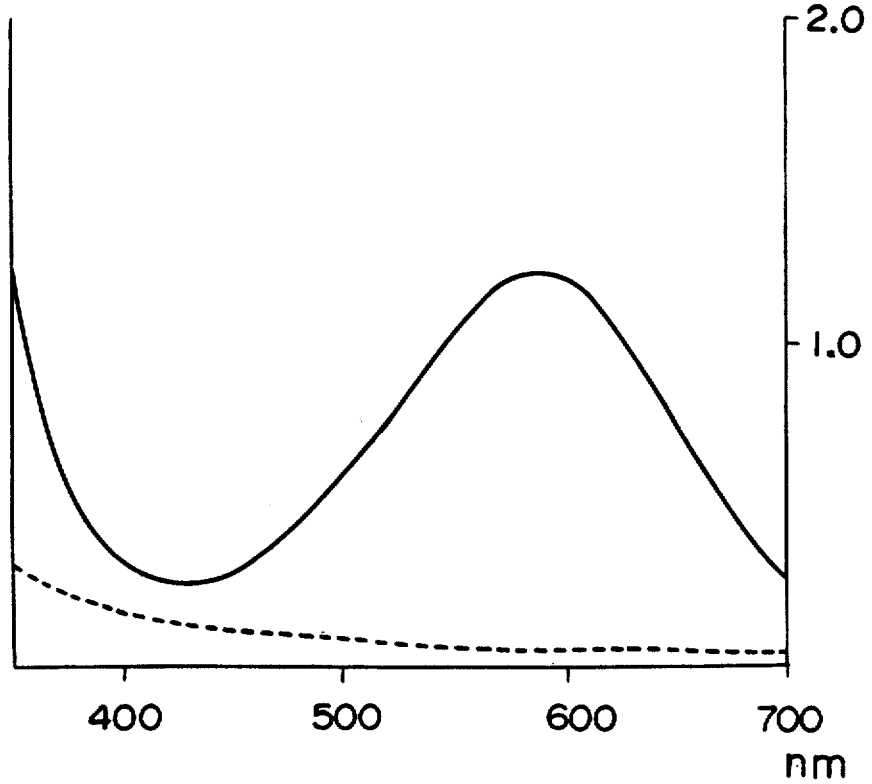
Figure 13:
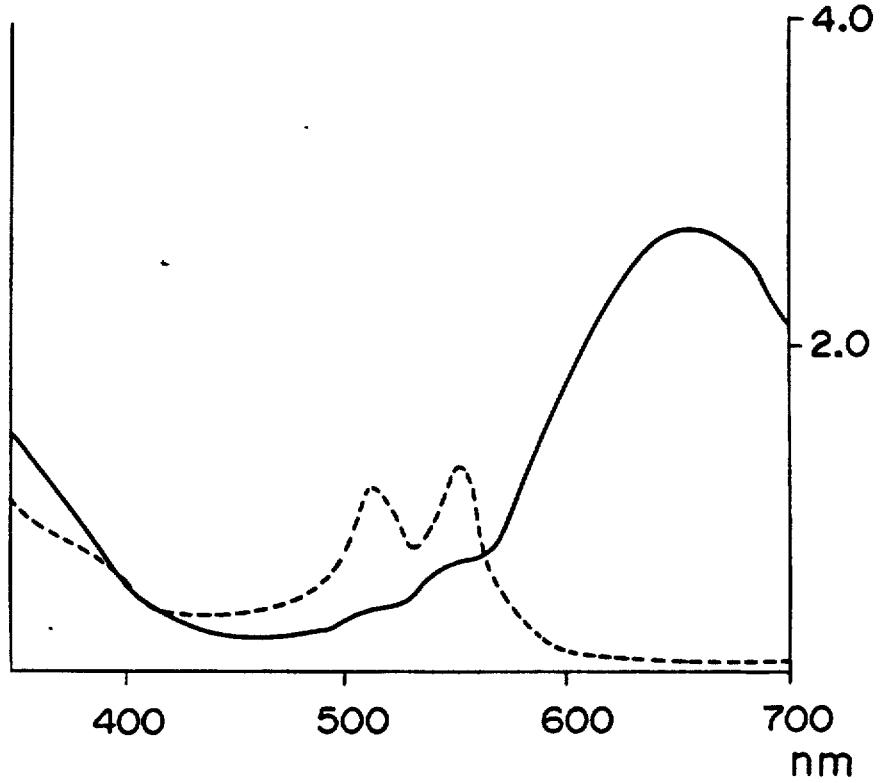
Figure 14:
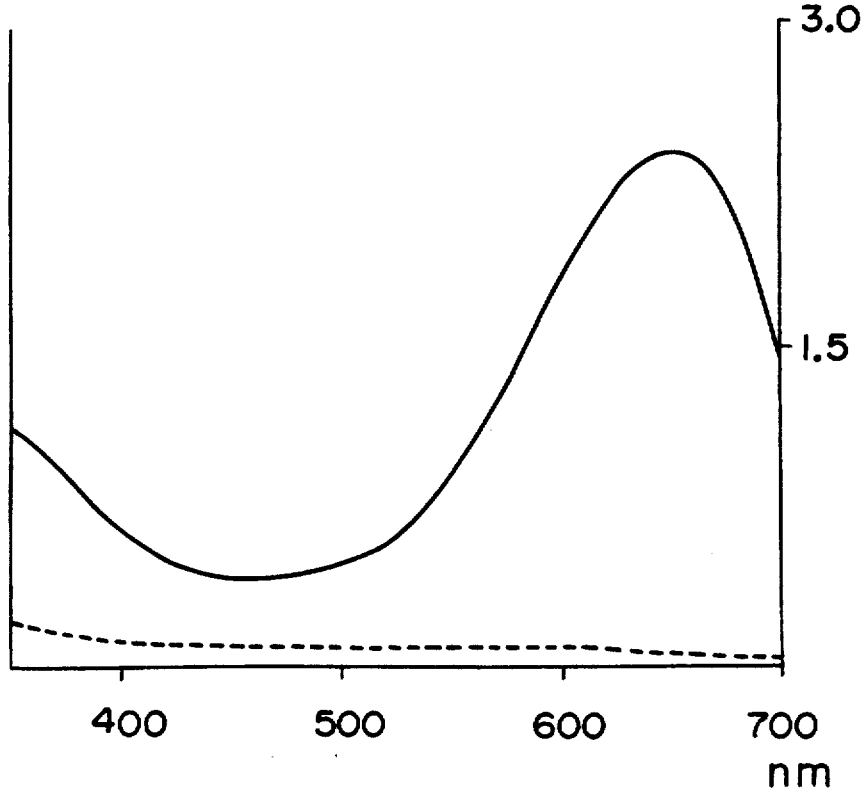
Figure 15:
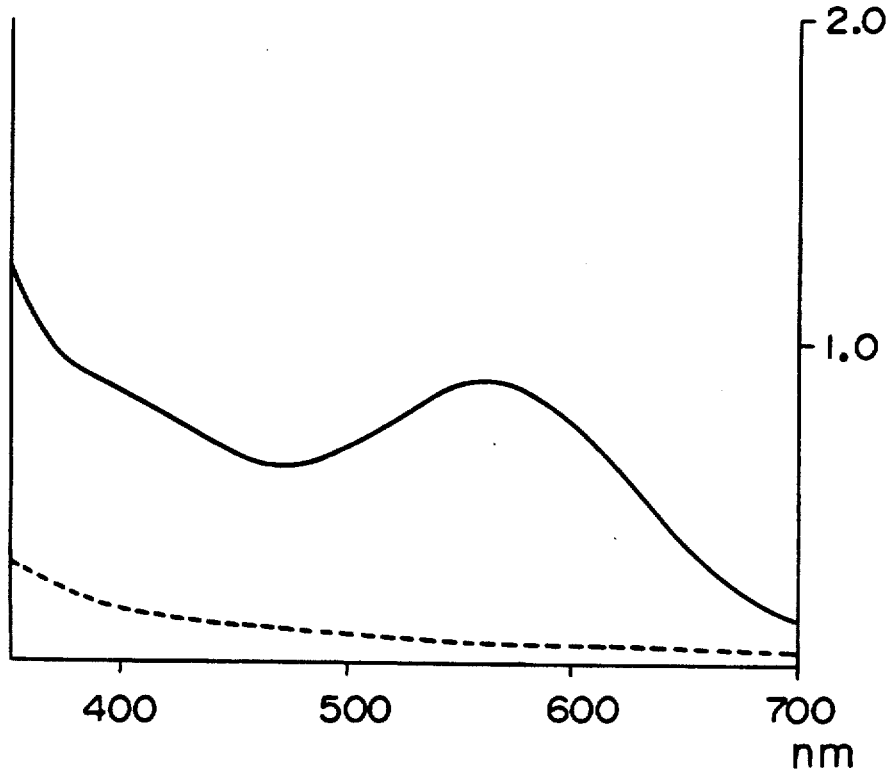
Figure 16:
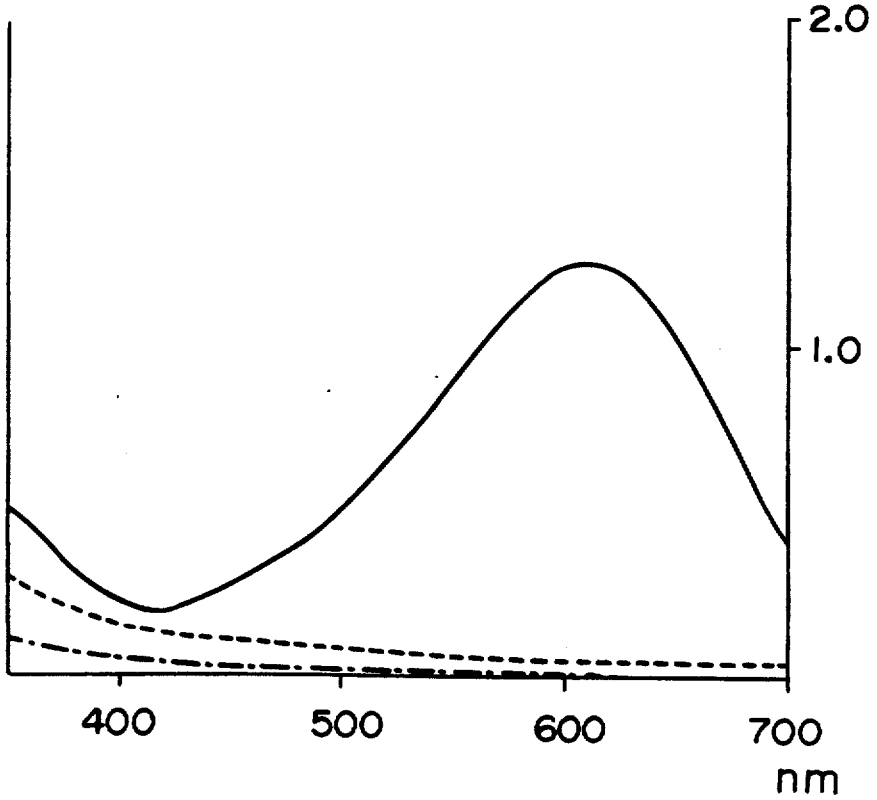
Figure 17:
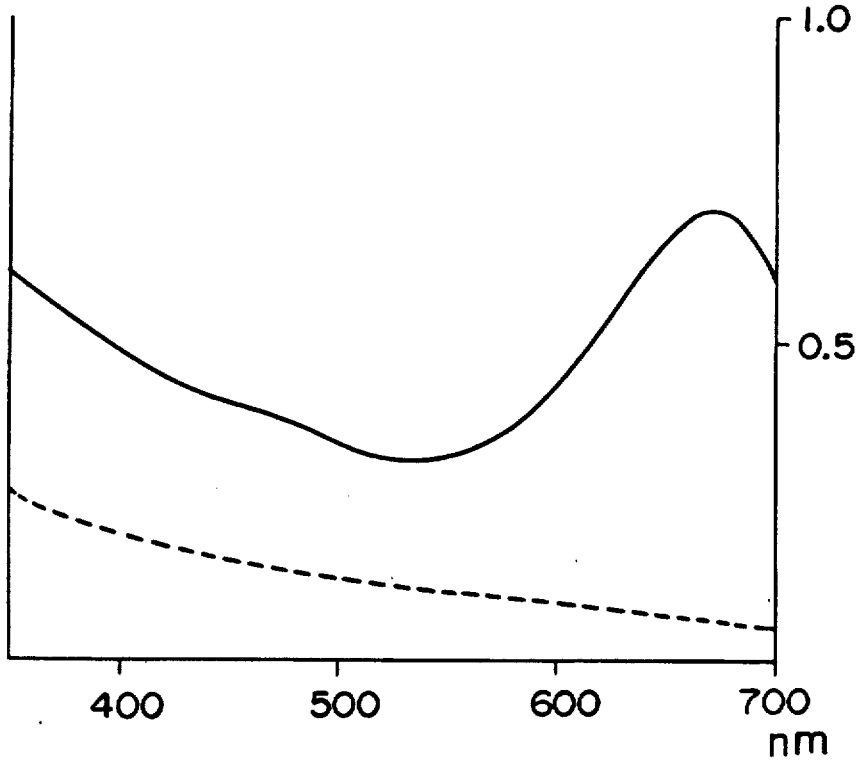
Figure 18:
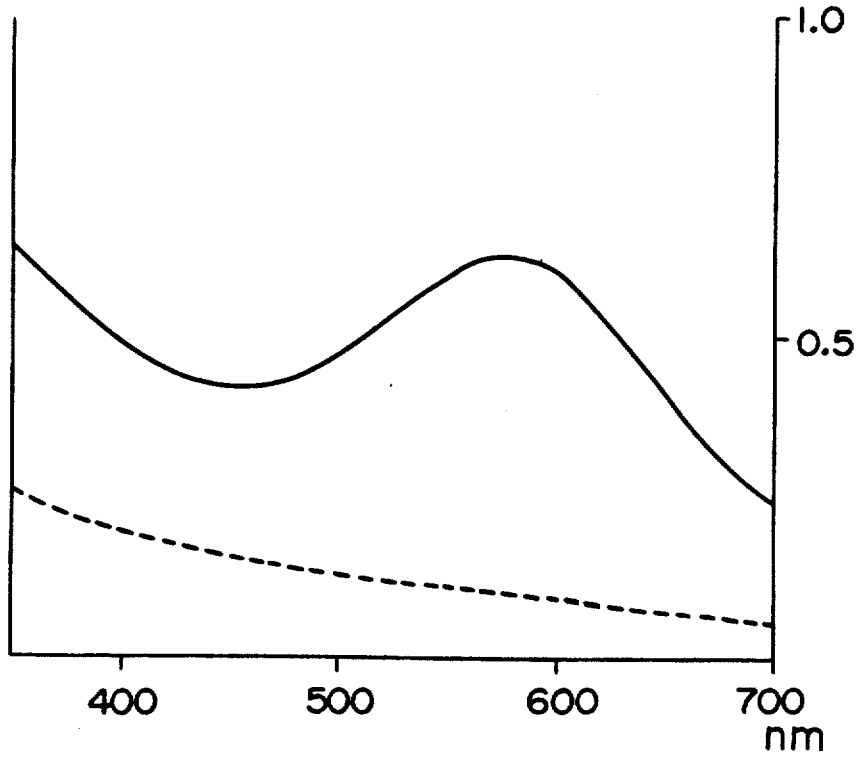
Figure 19:
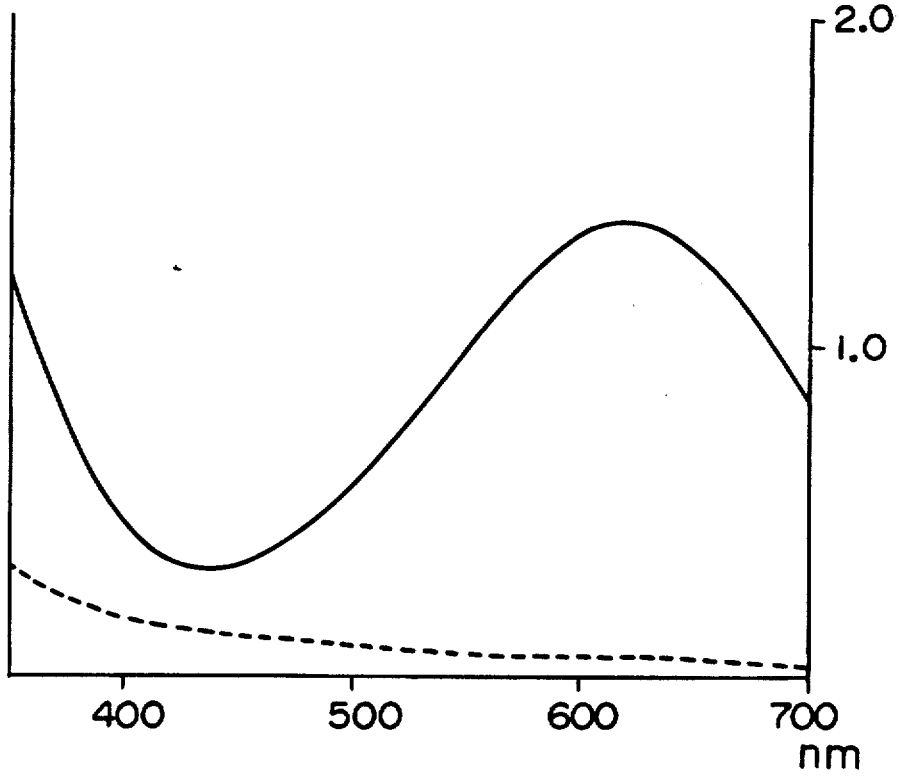
Figure 20:
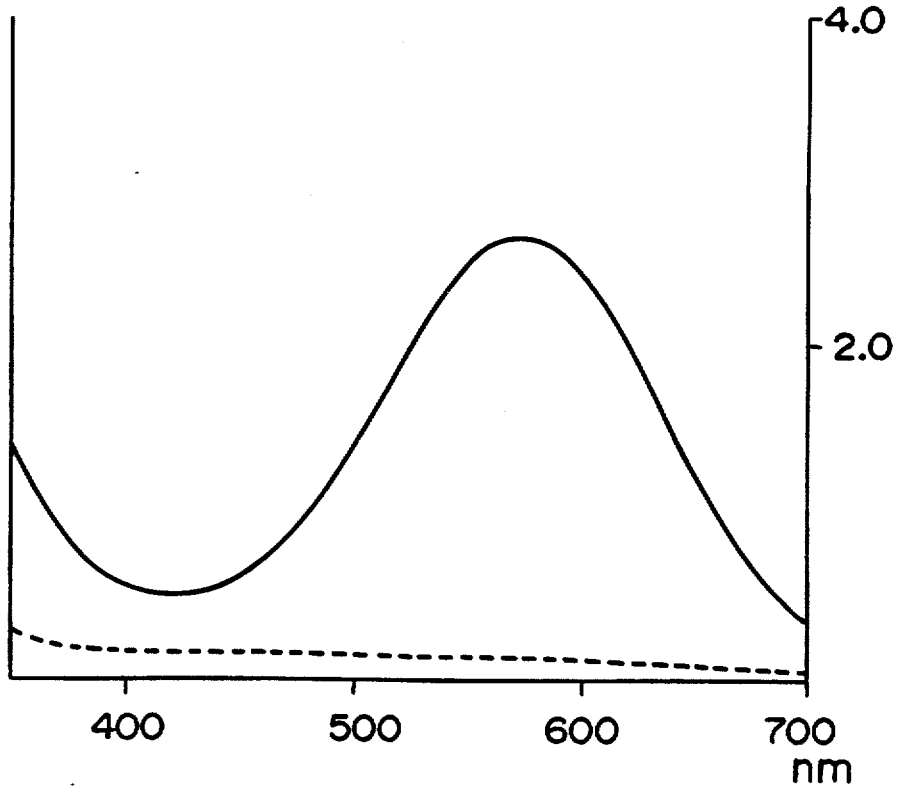
Figure 21:
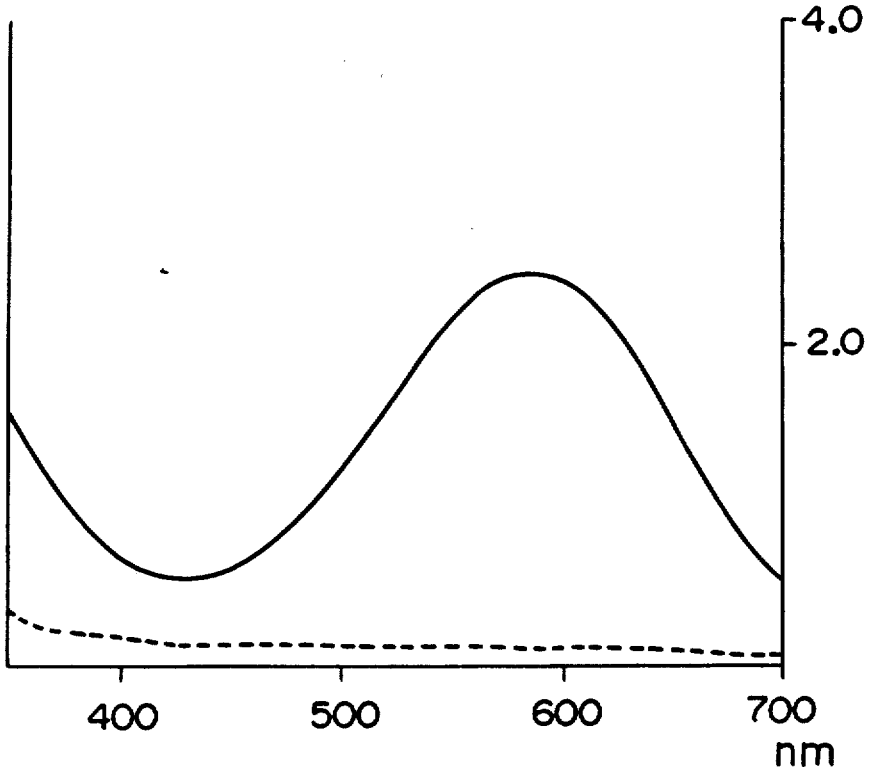
Figure 22:
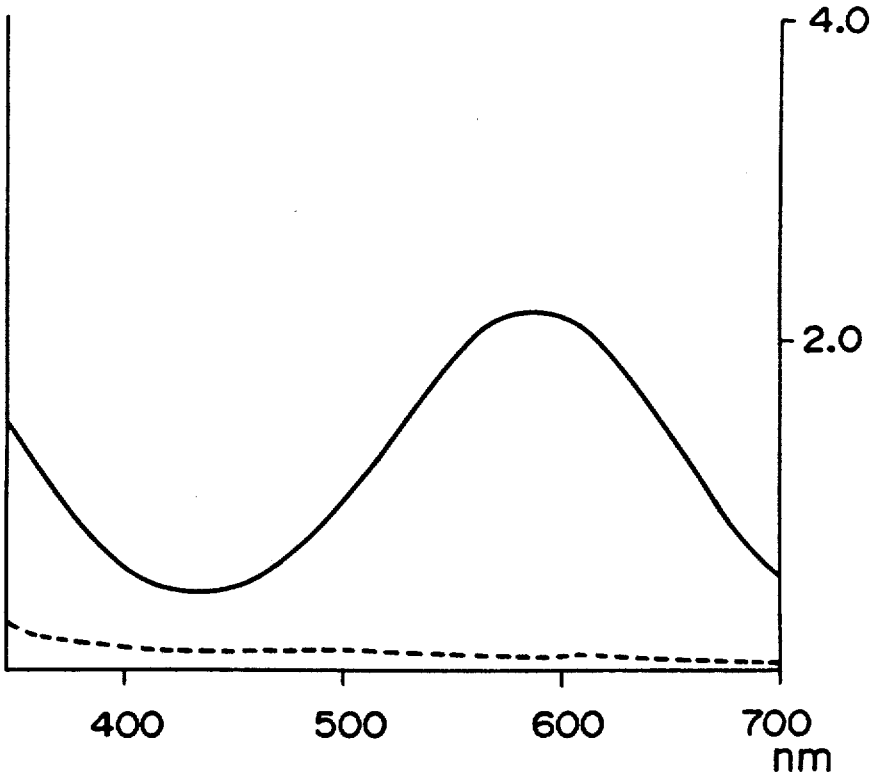
Figure 23:
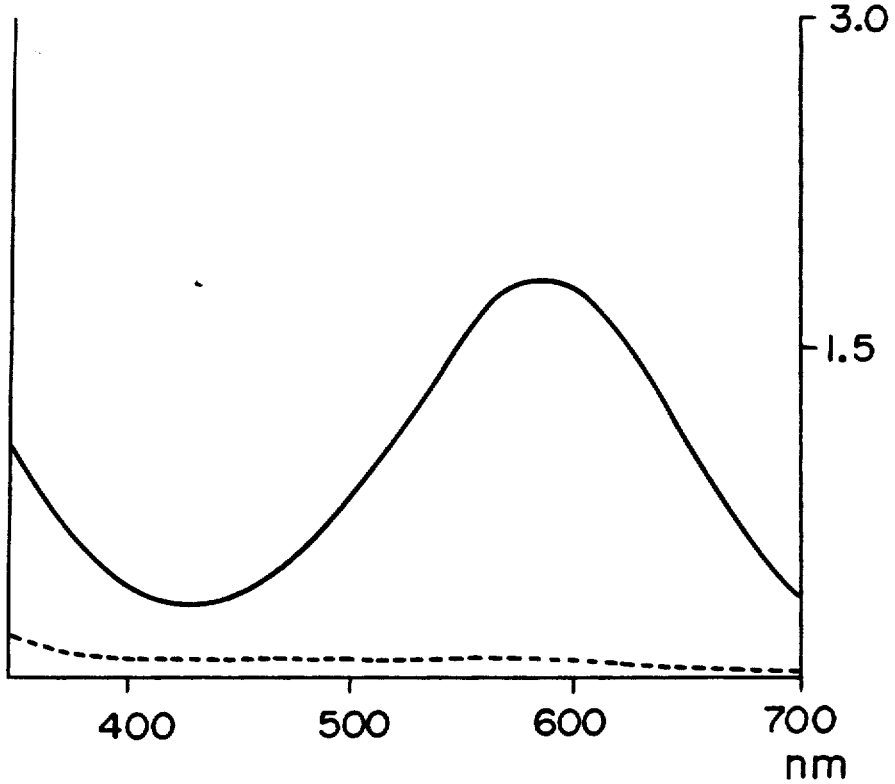
Figure 24:
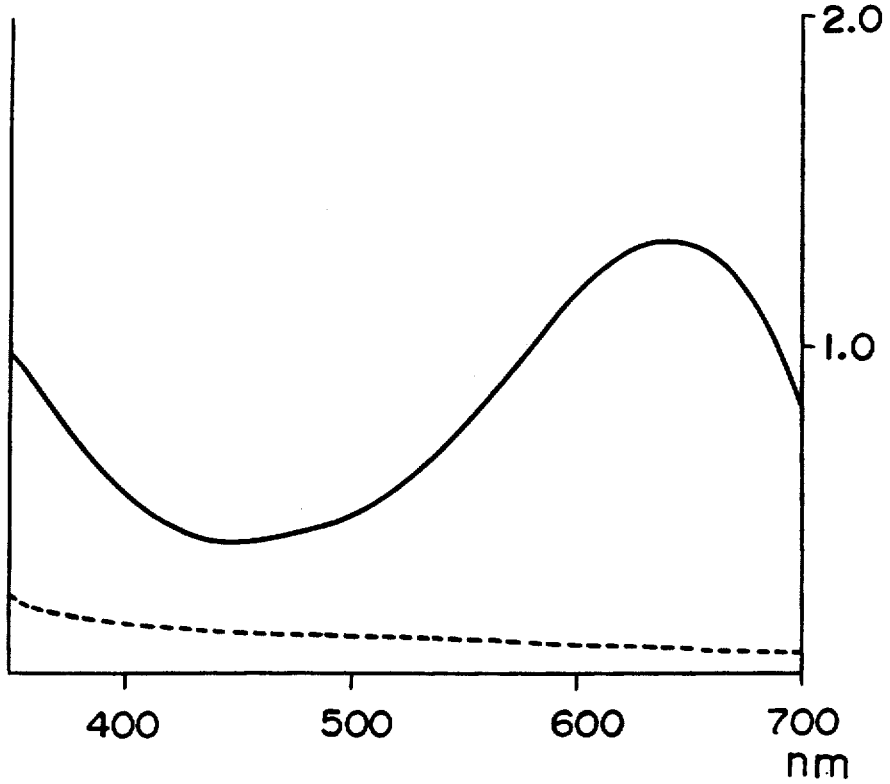
Figure 25:
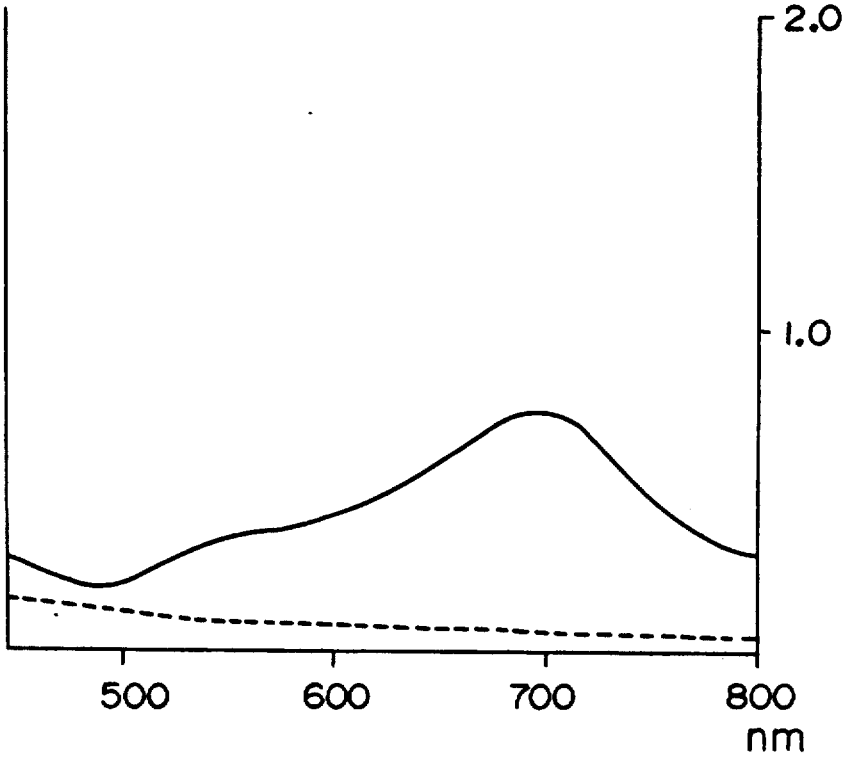
Figure 26:
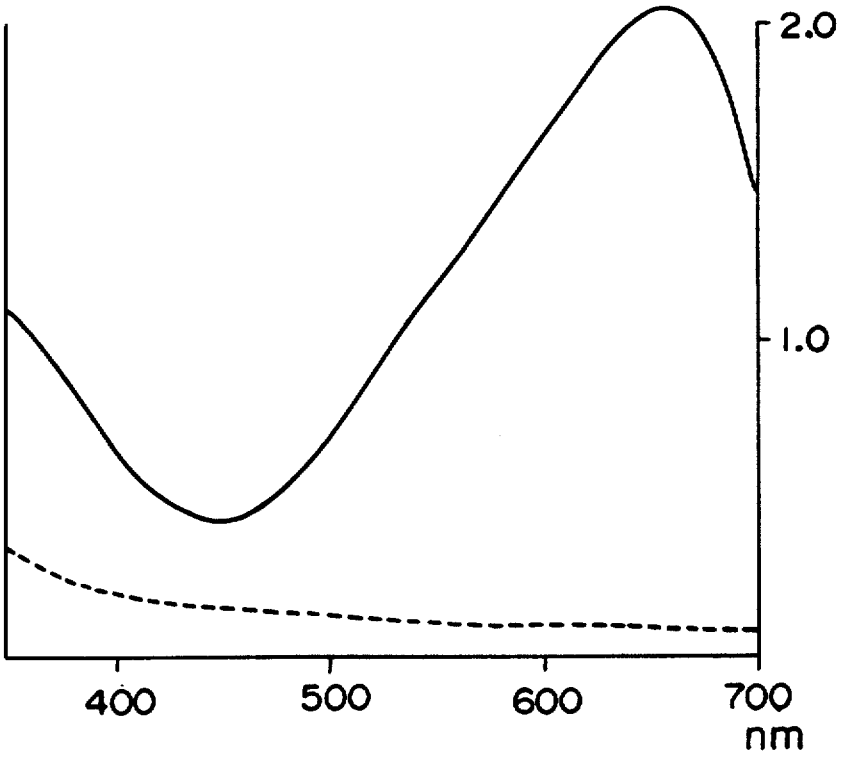
Figure 27:
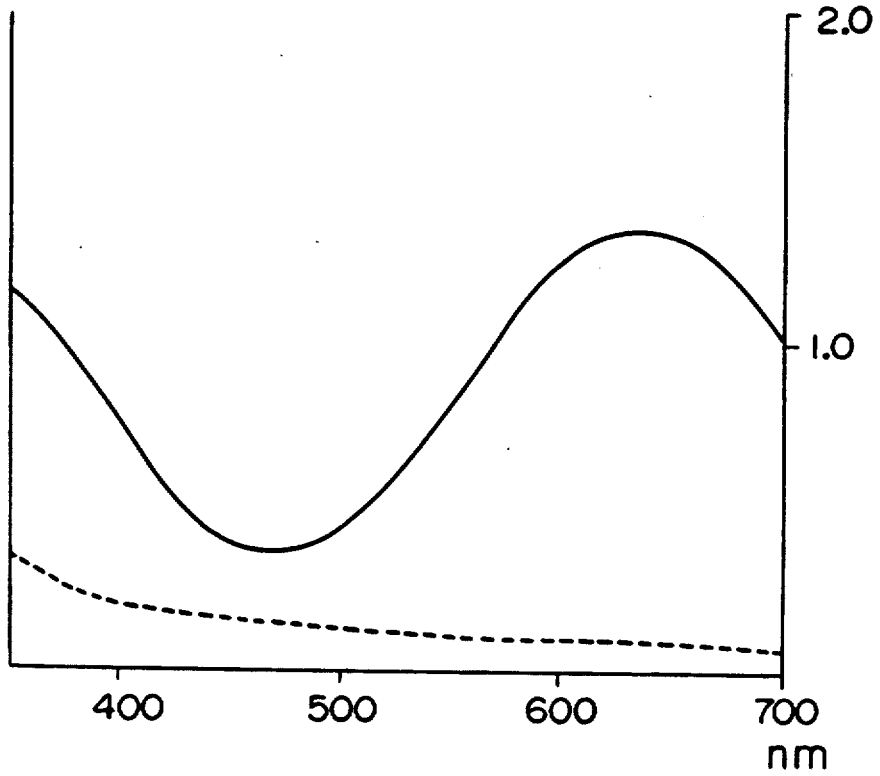
Figure 28:
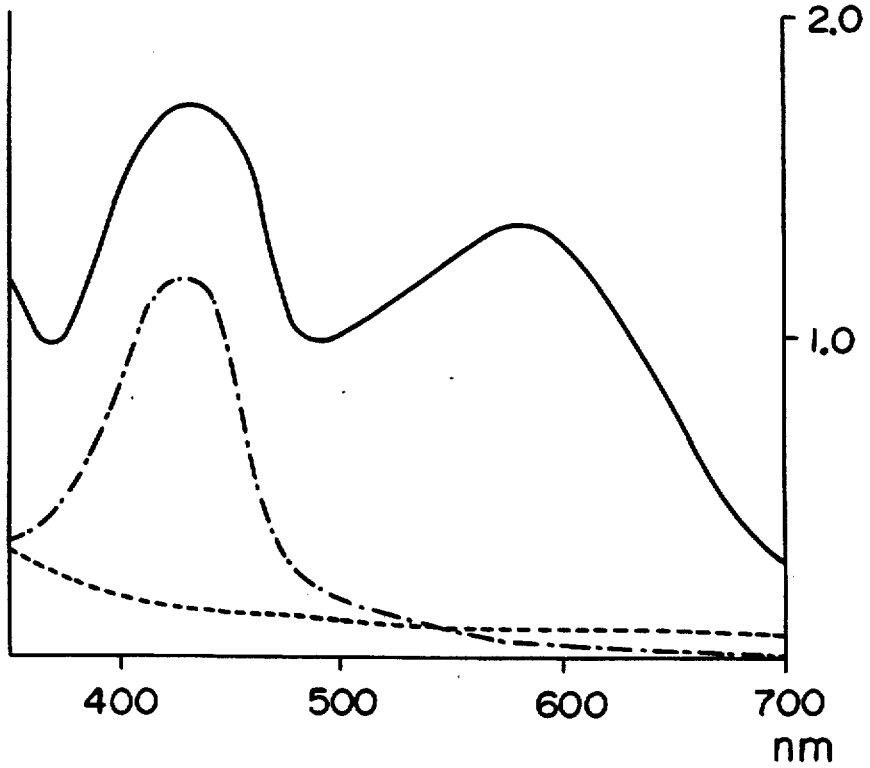
Figure 29:
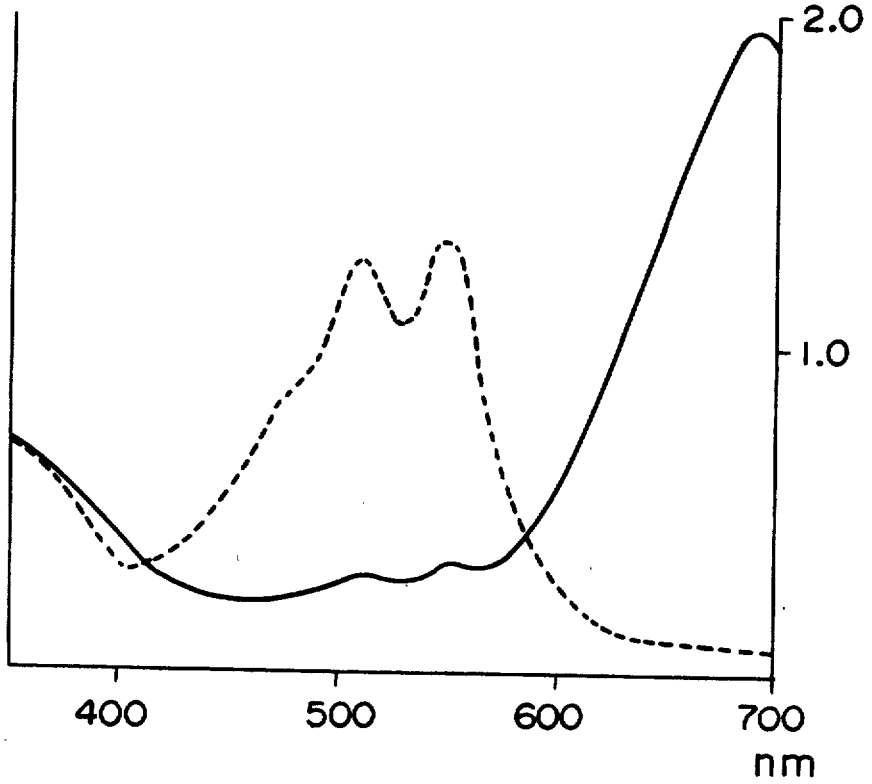
Figure 30:
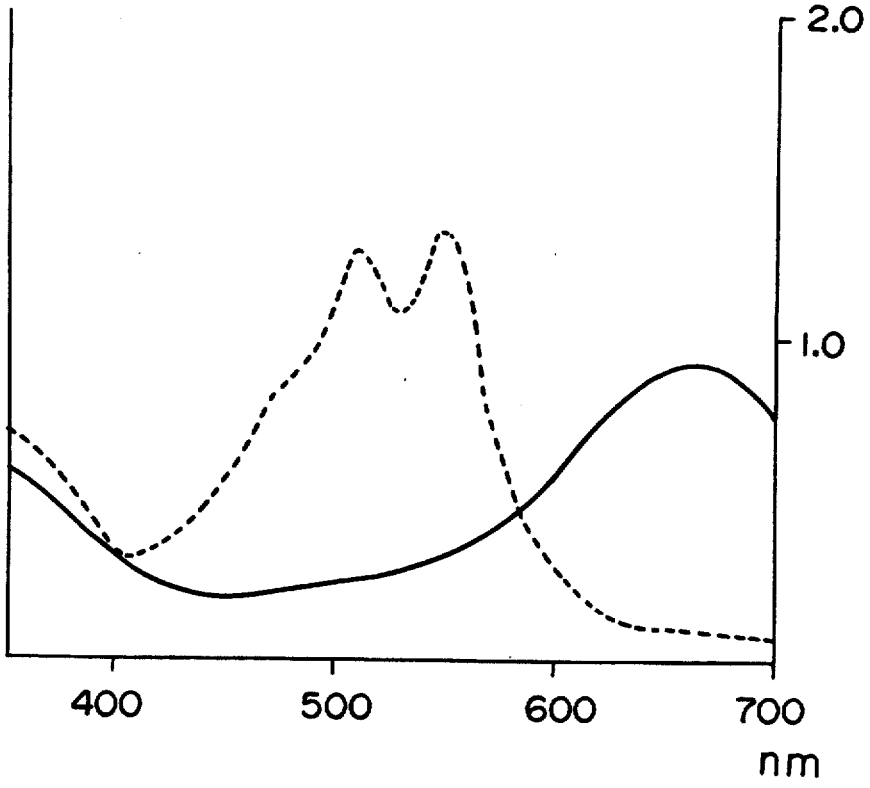
Figure 31:
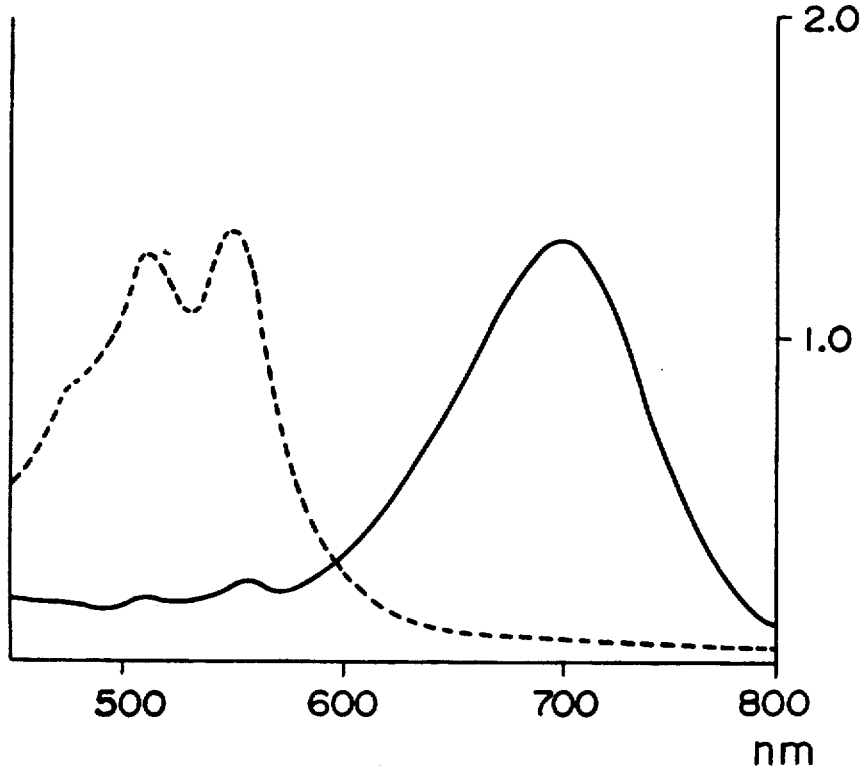
Figure 32:
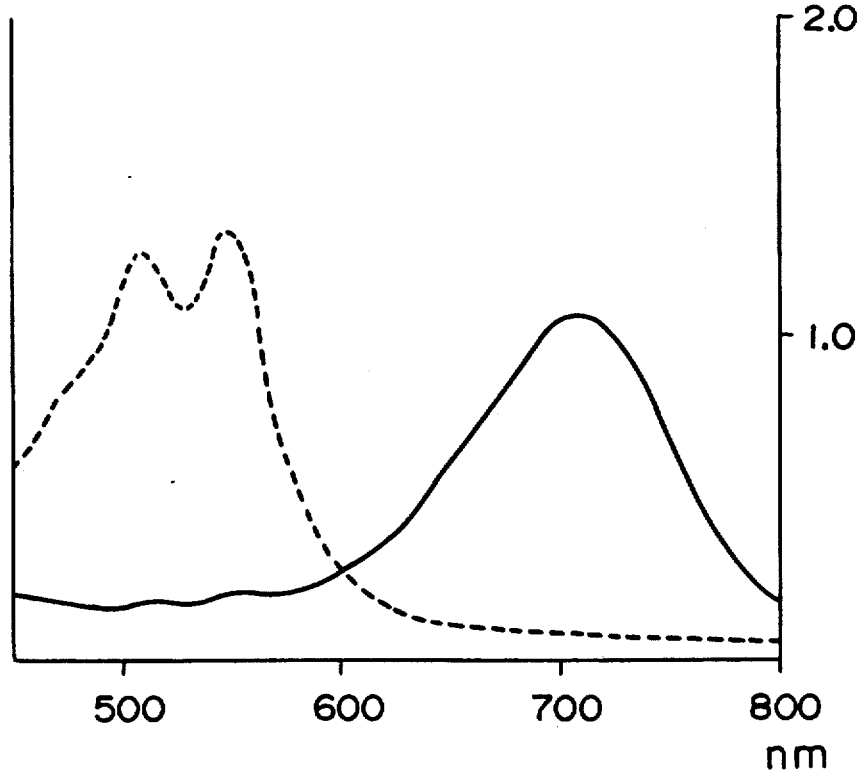
Figure 33:
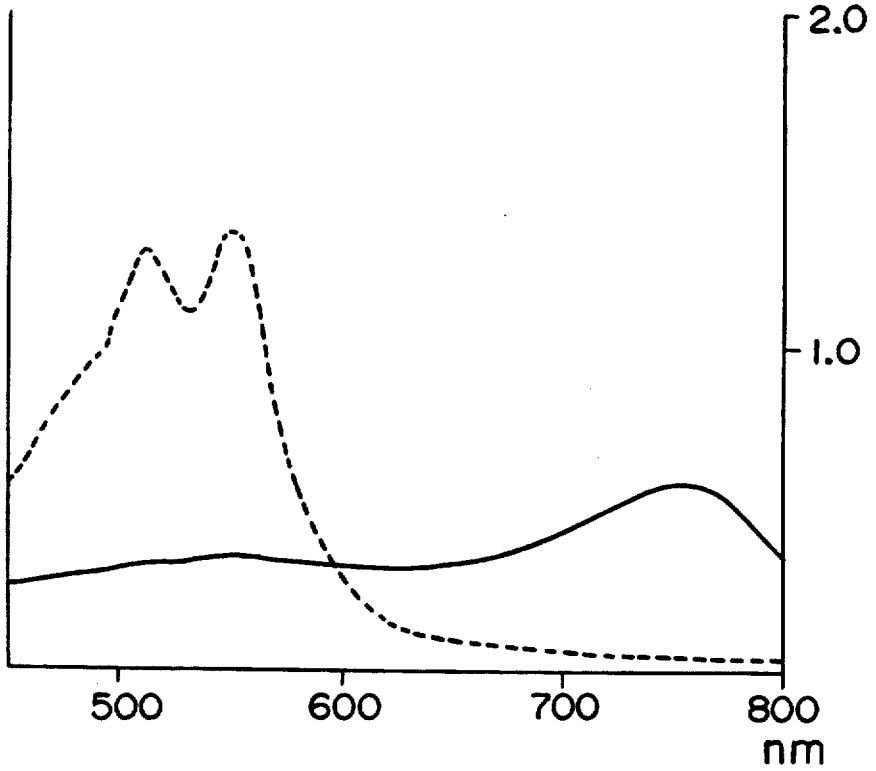
Figure 34:
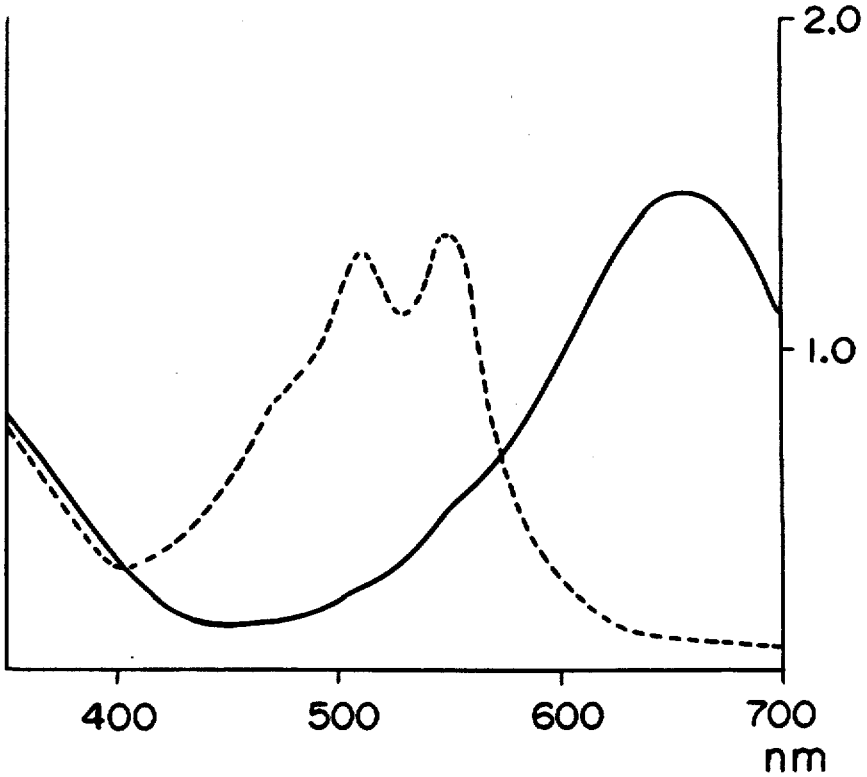
Figure 35:
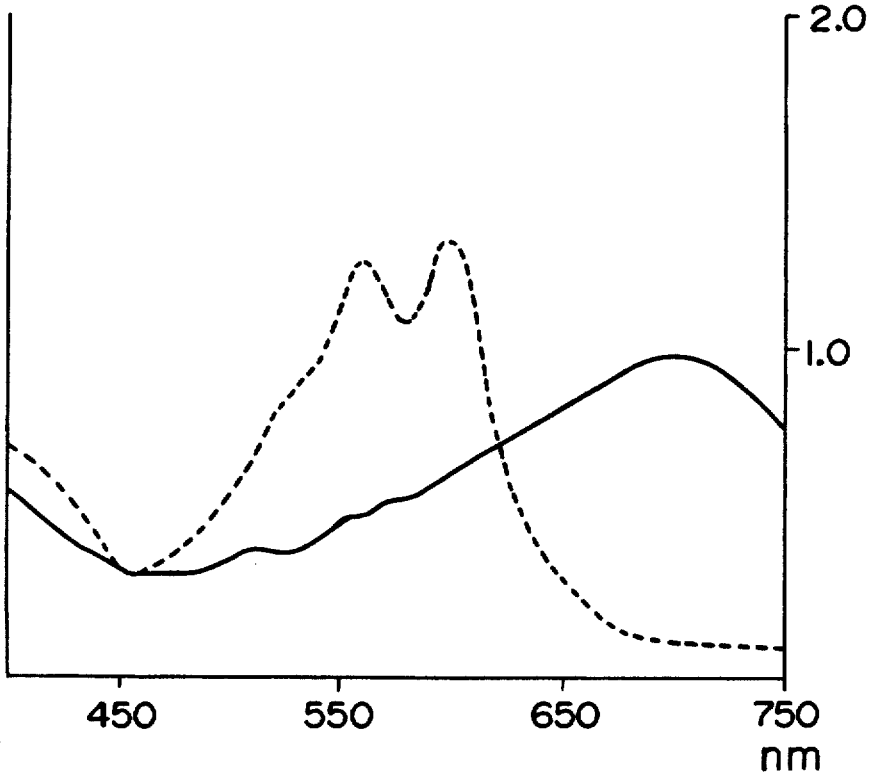
Figure 36:
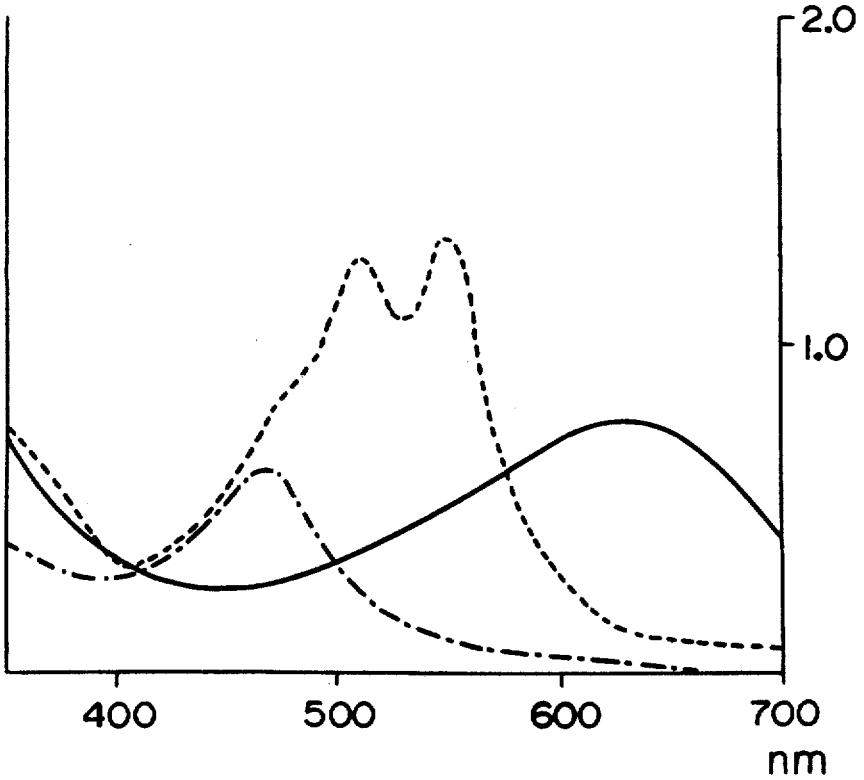
Figure 37:
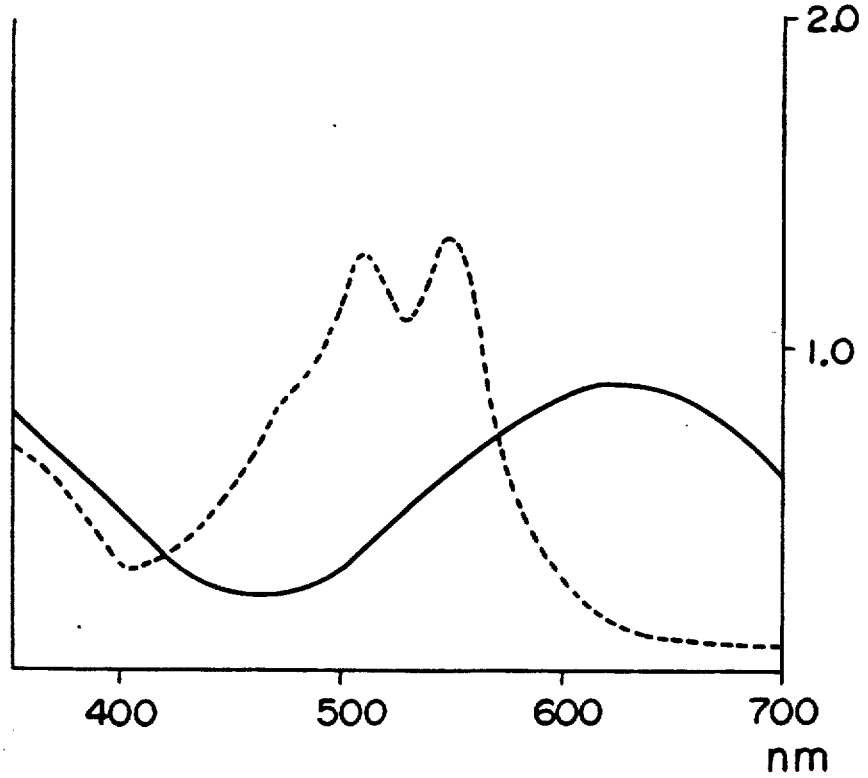
Figure 38:
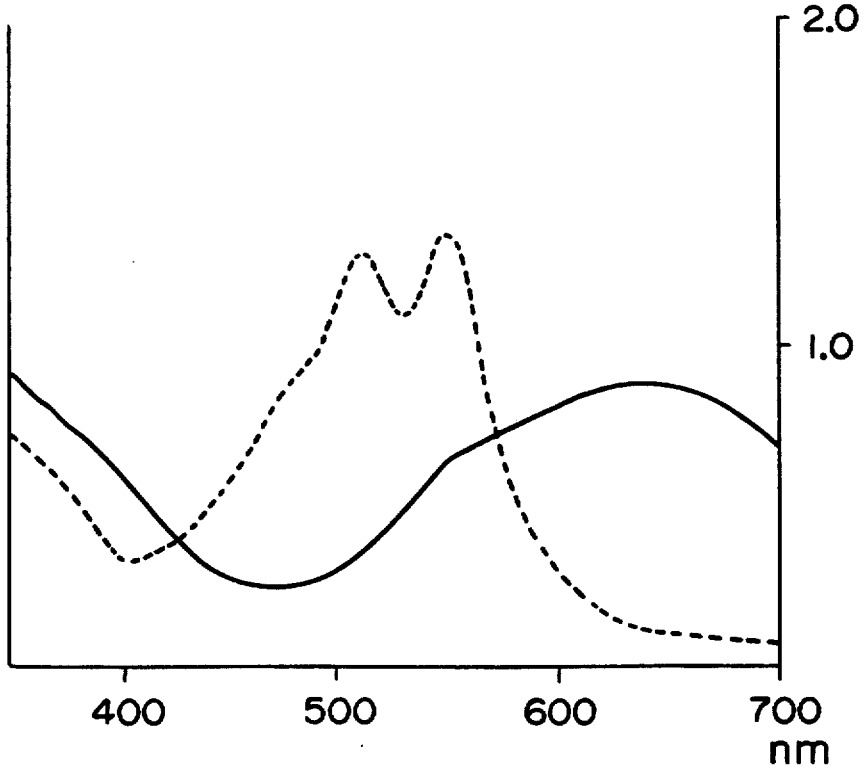
Figure 39:
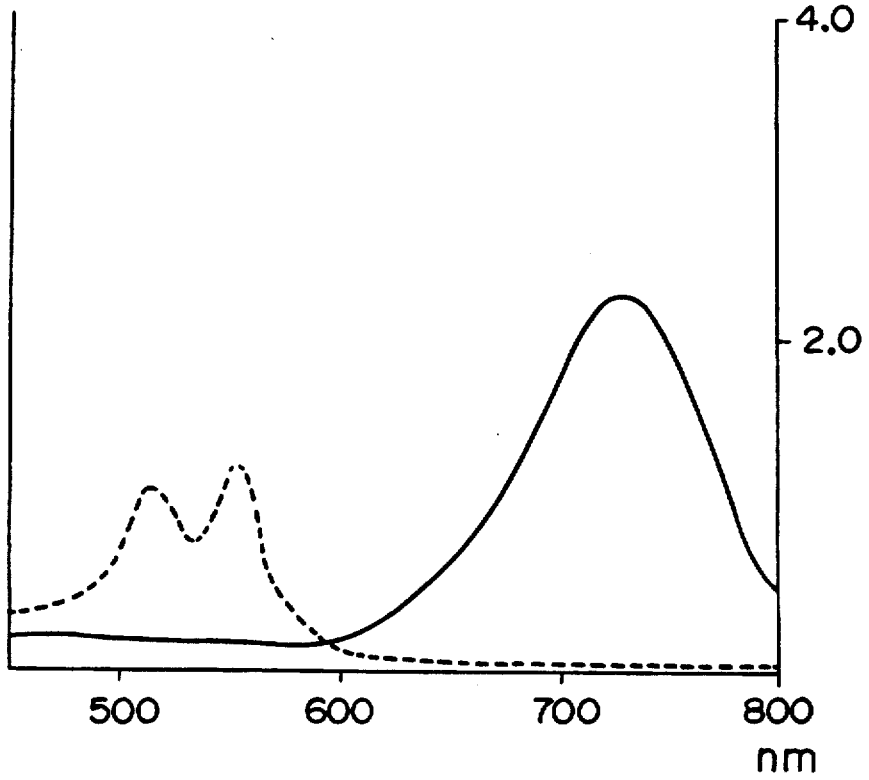
Figure 40:
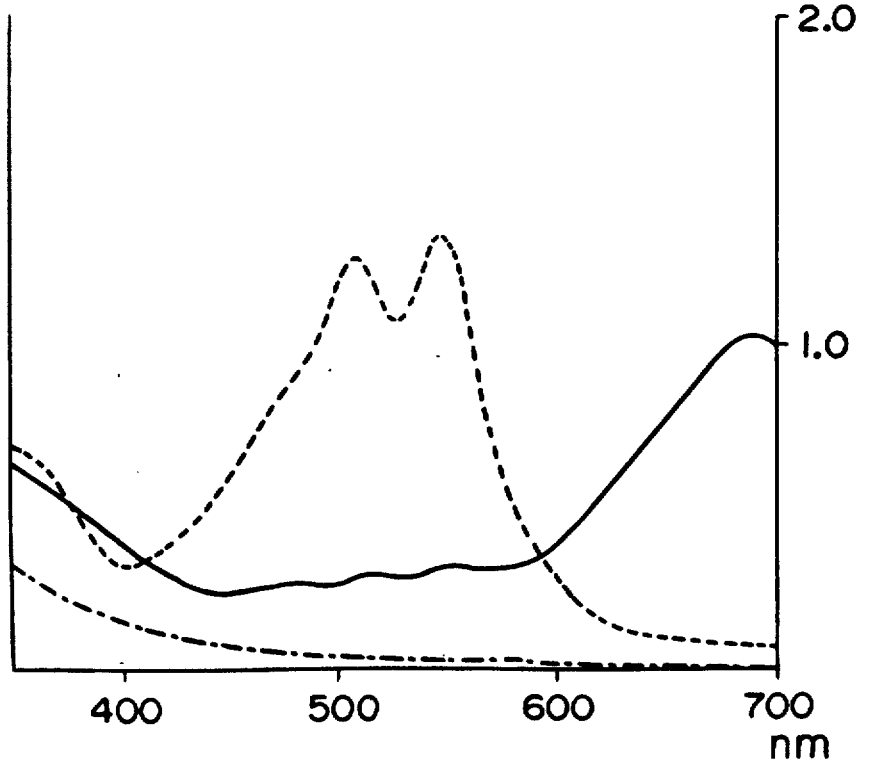
Figure 41:
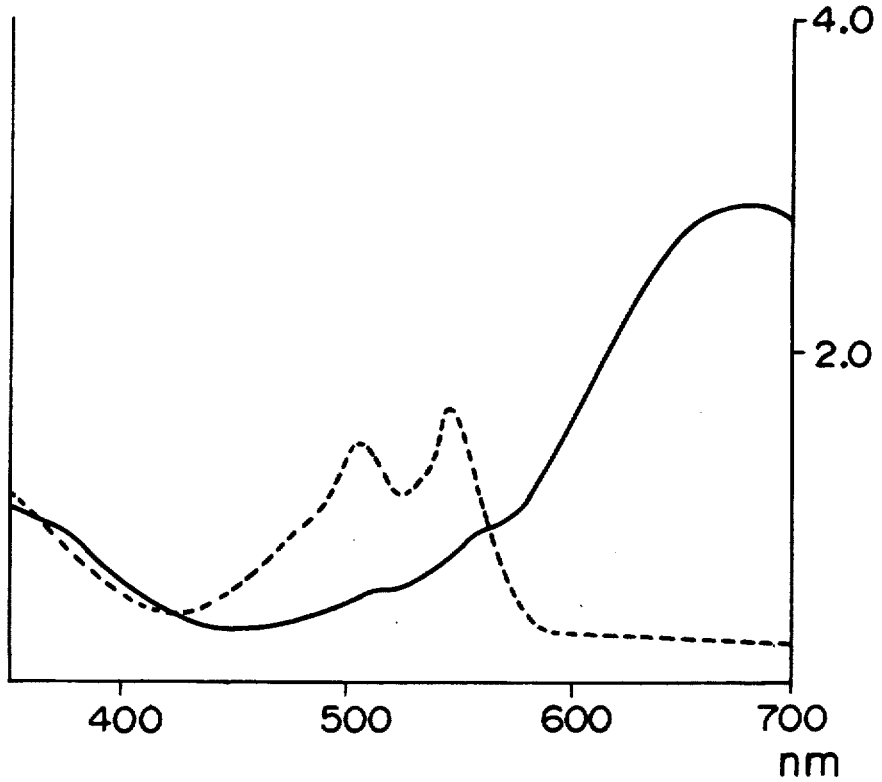
Figure 42:
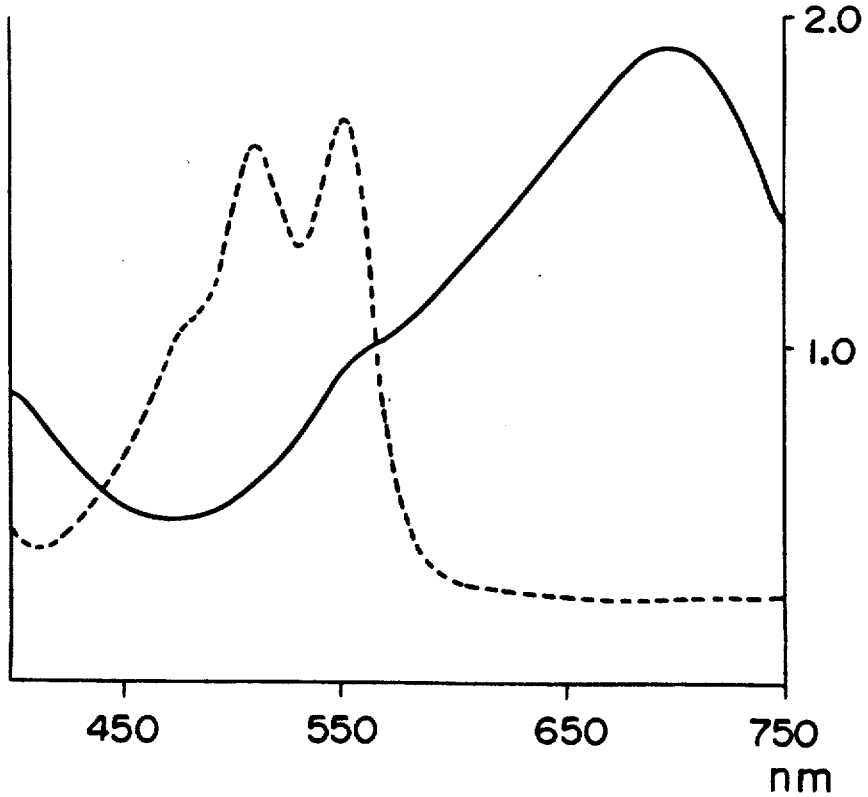
Figure 43:
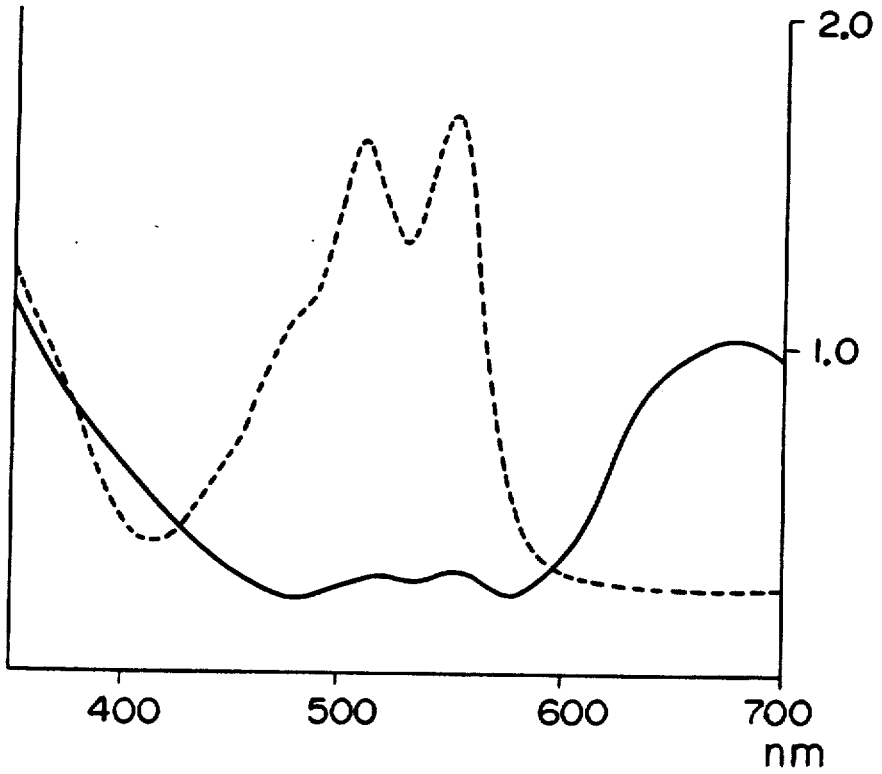
Figure 44:
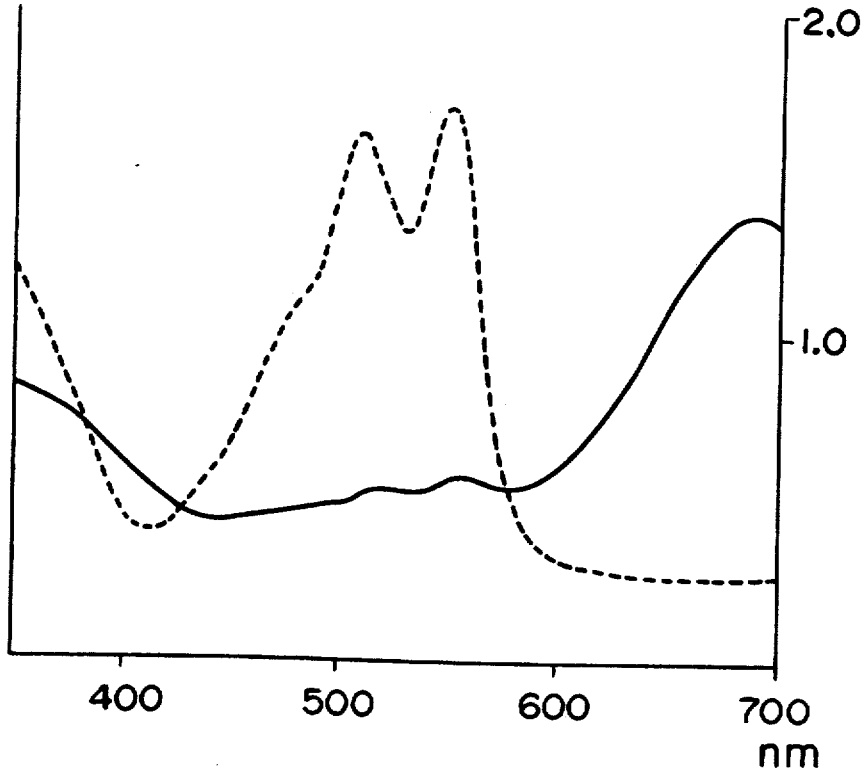
Figure 45:
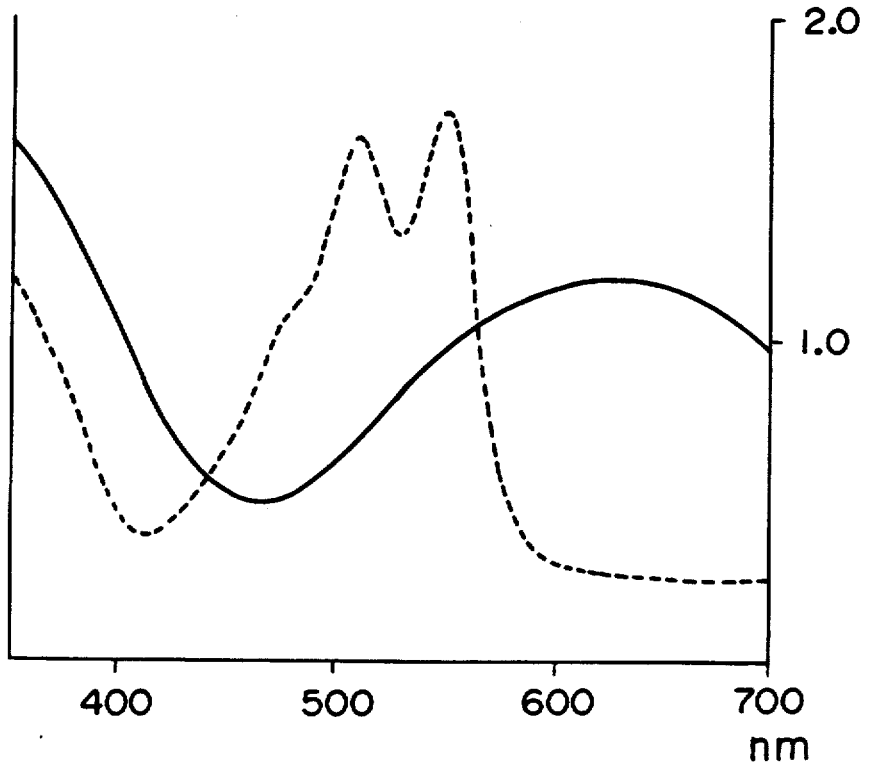
Figure 46:
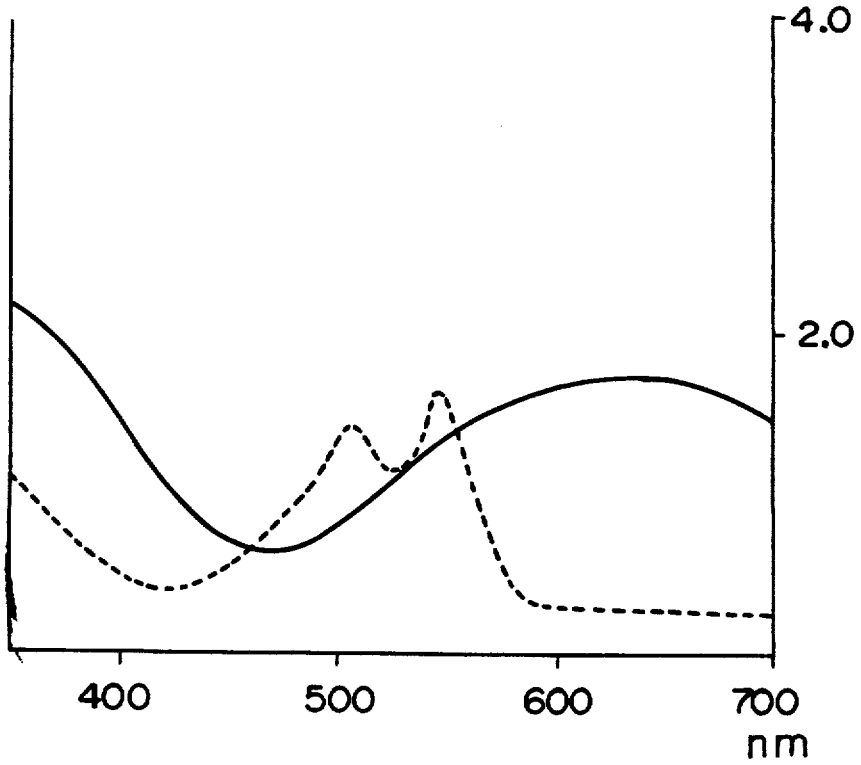
Figure 47:
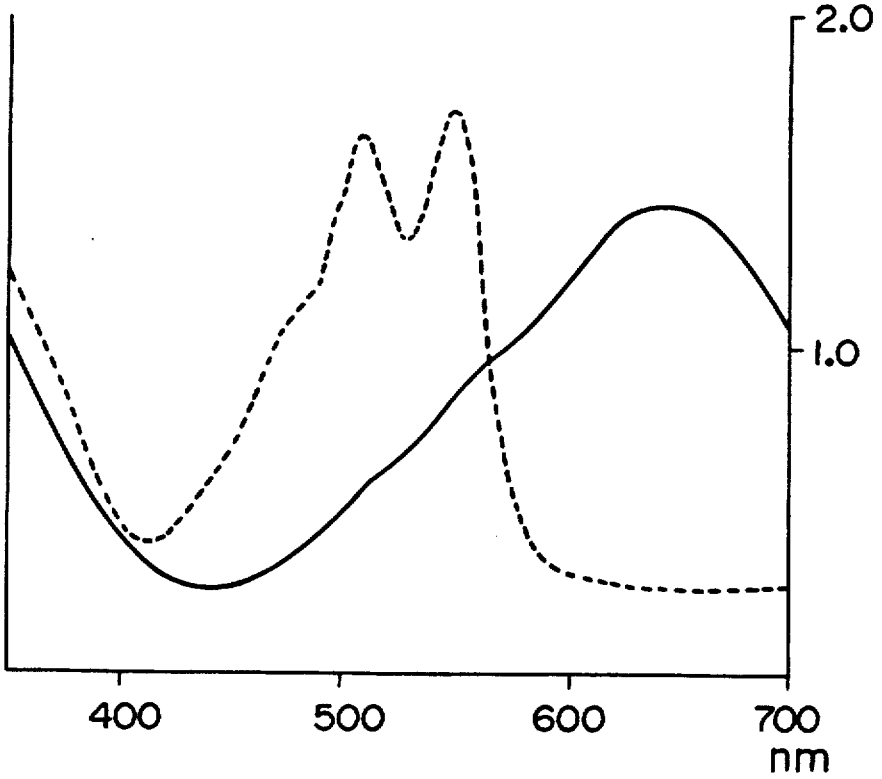
Figure 48:
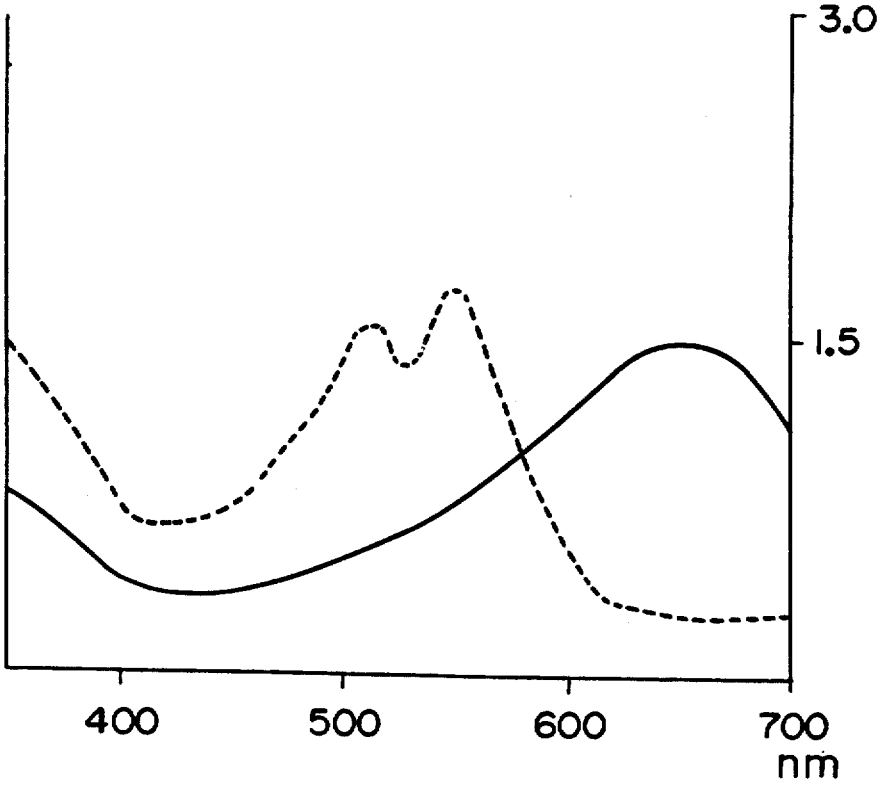
Figure 49:
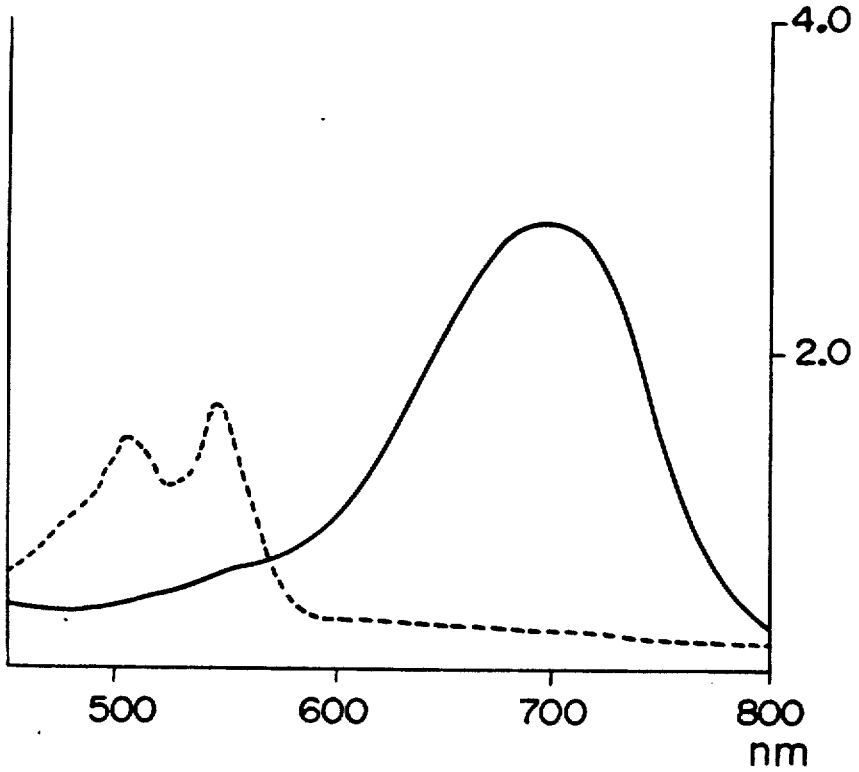
Figure 50:
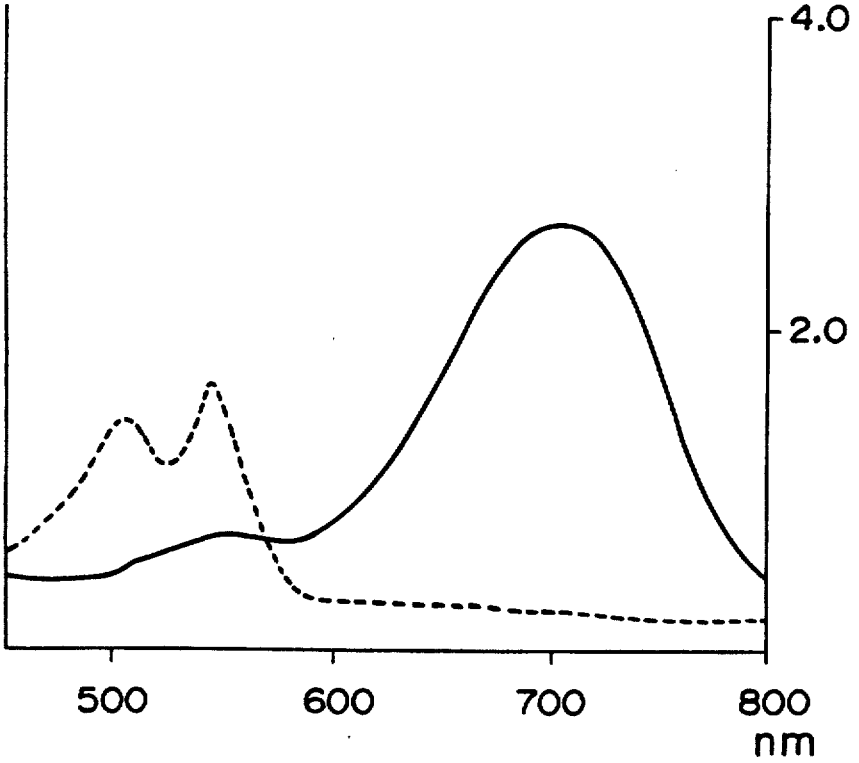
Figure 51:
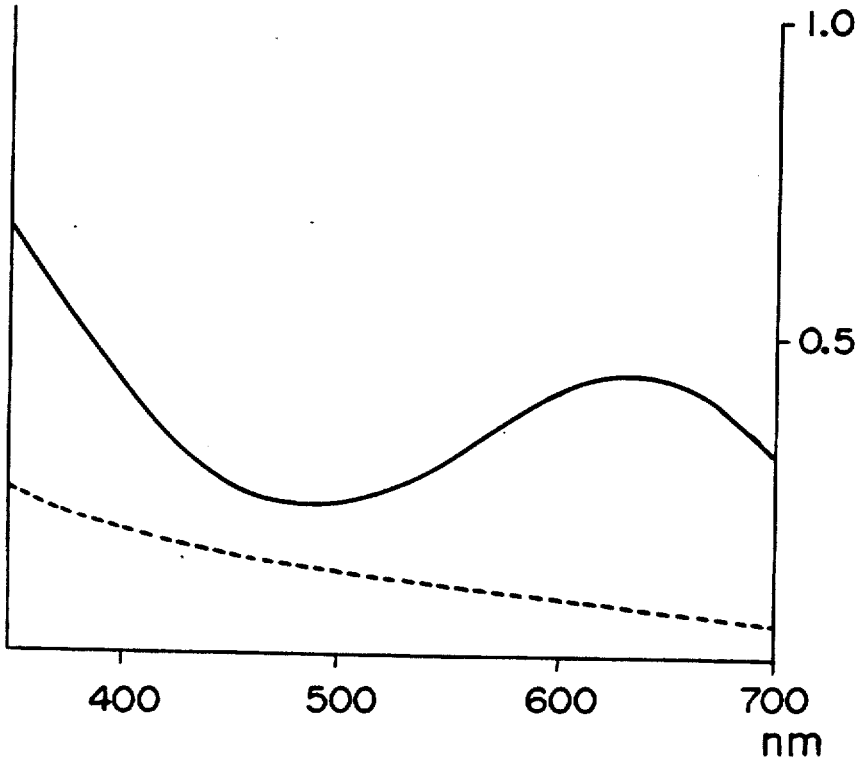
Figure 52:
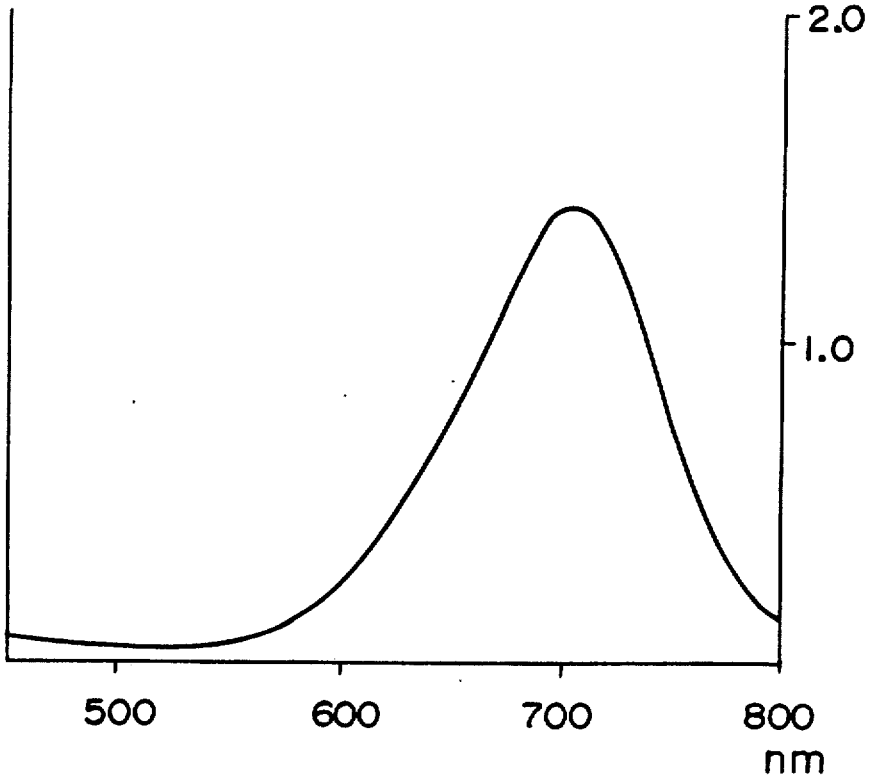
Figure 53:
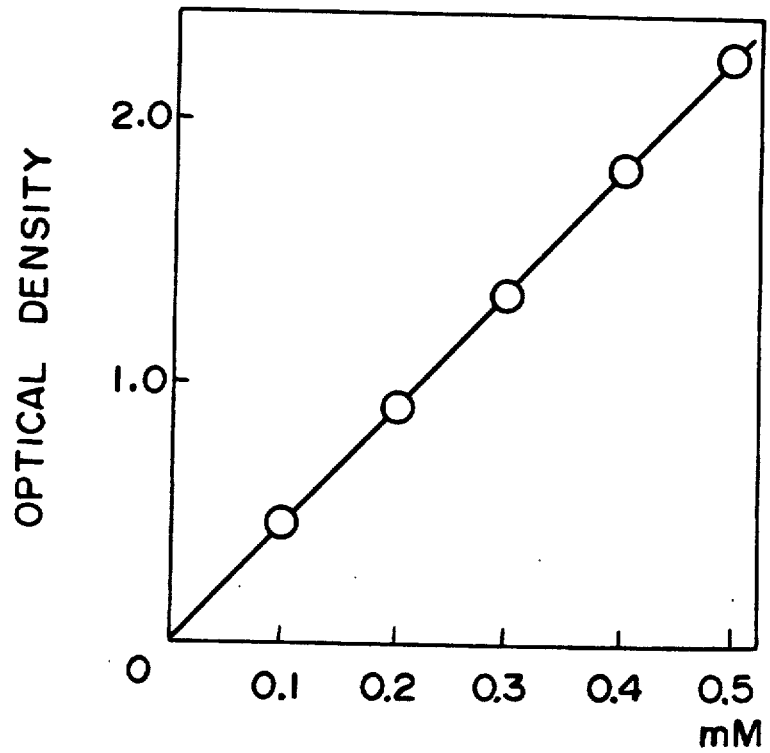
Figure 54:
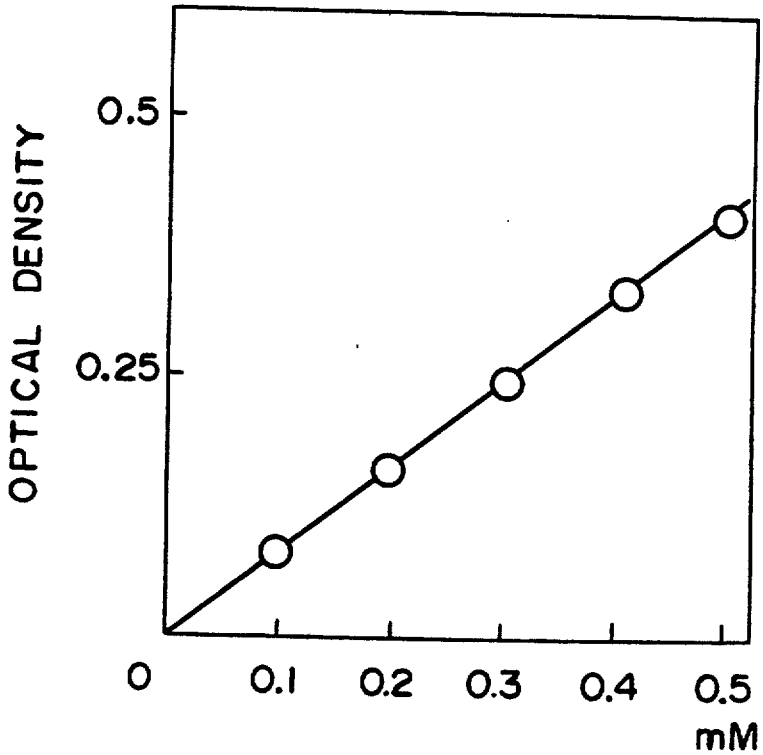
Figure 55:
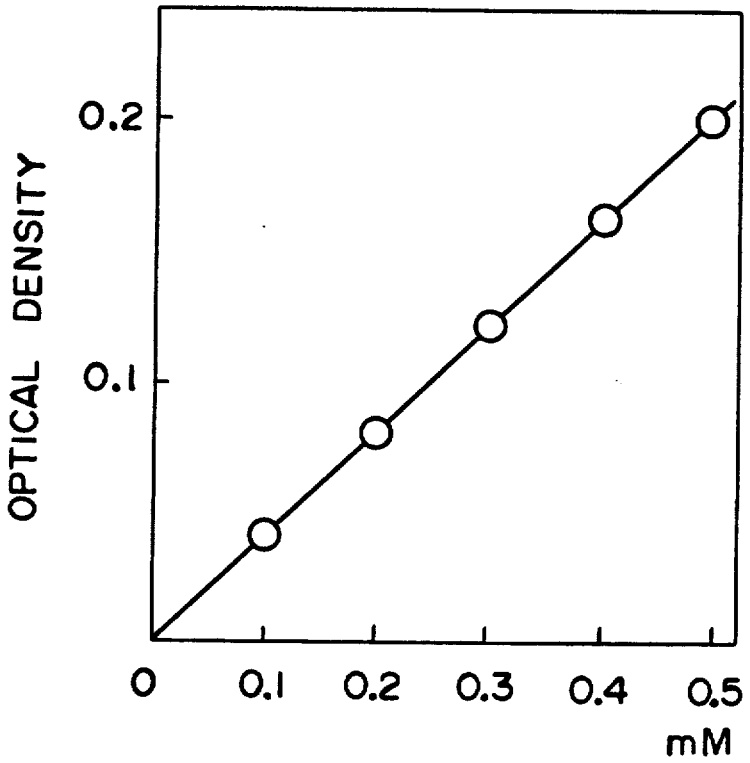
Figure 56:
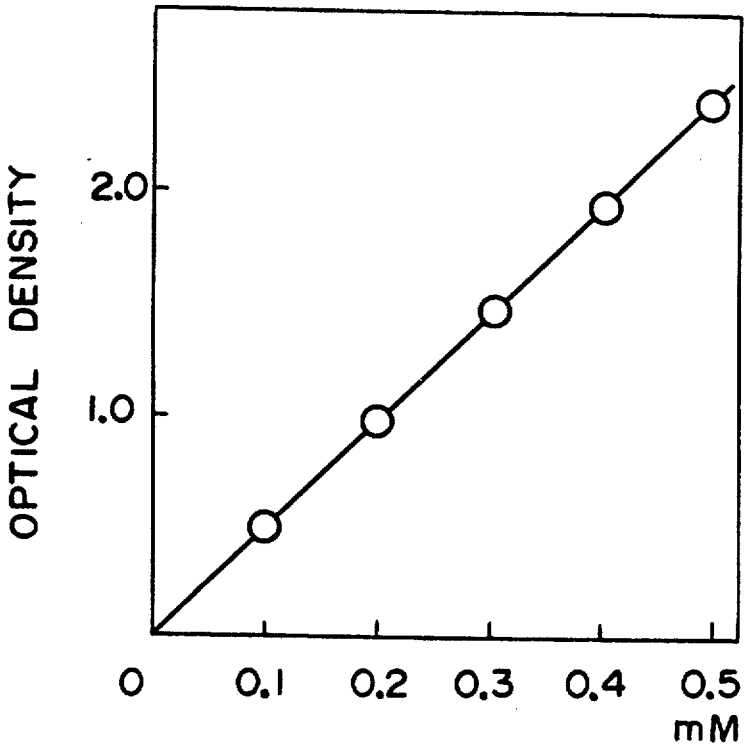
Figure 57:
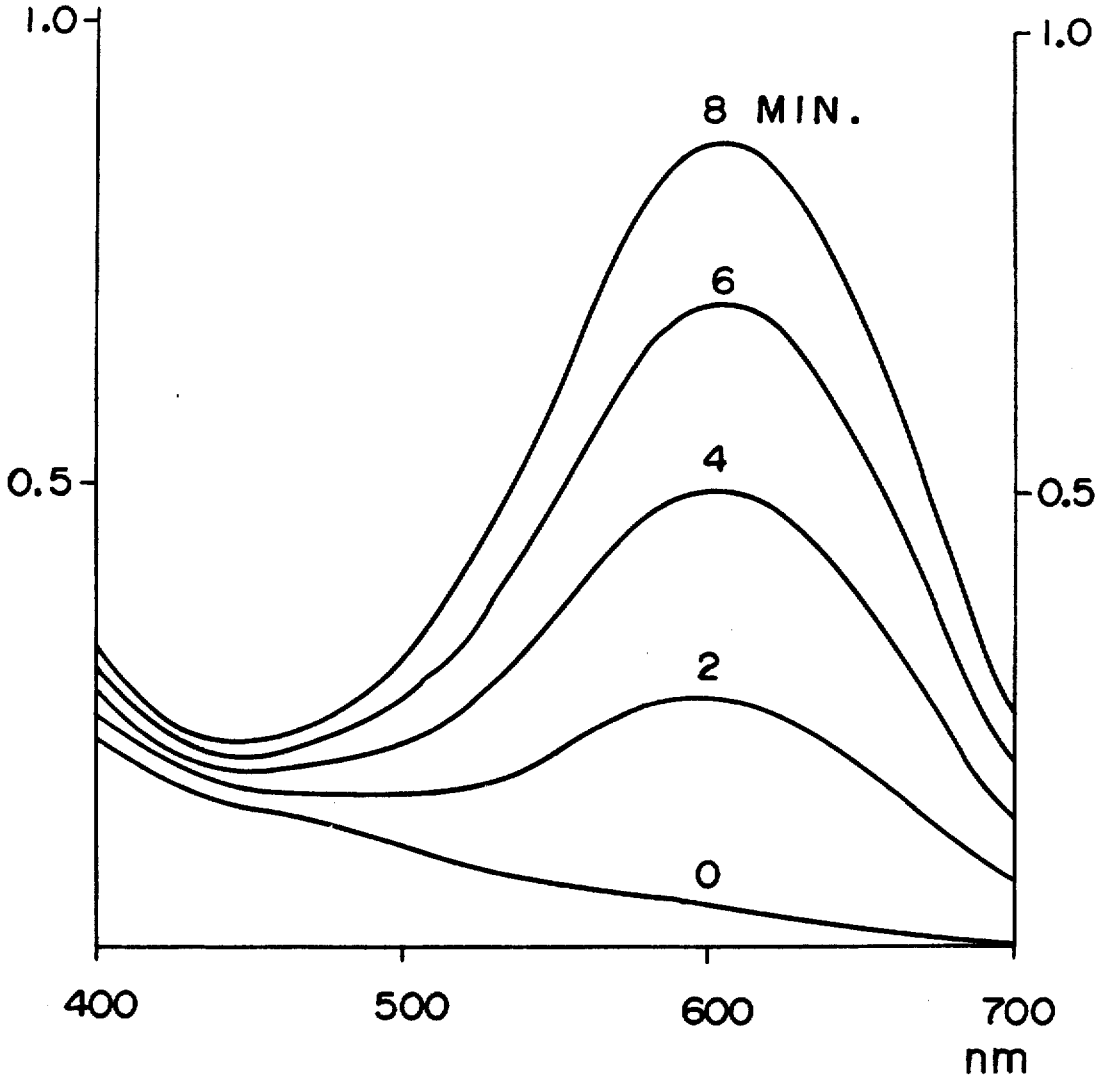
Figure 58:
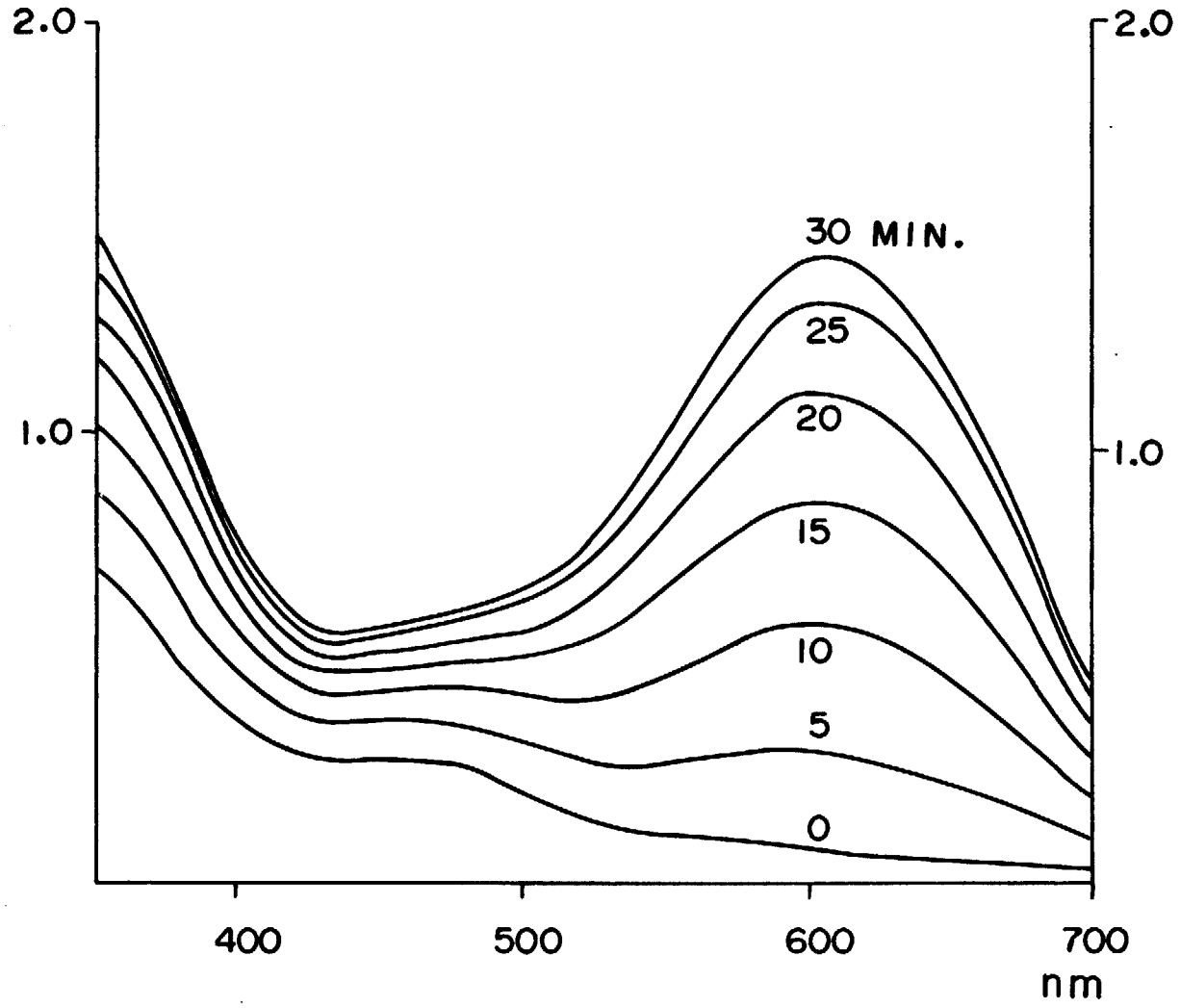
Figure 59:
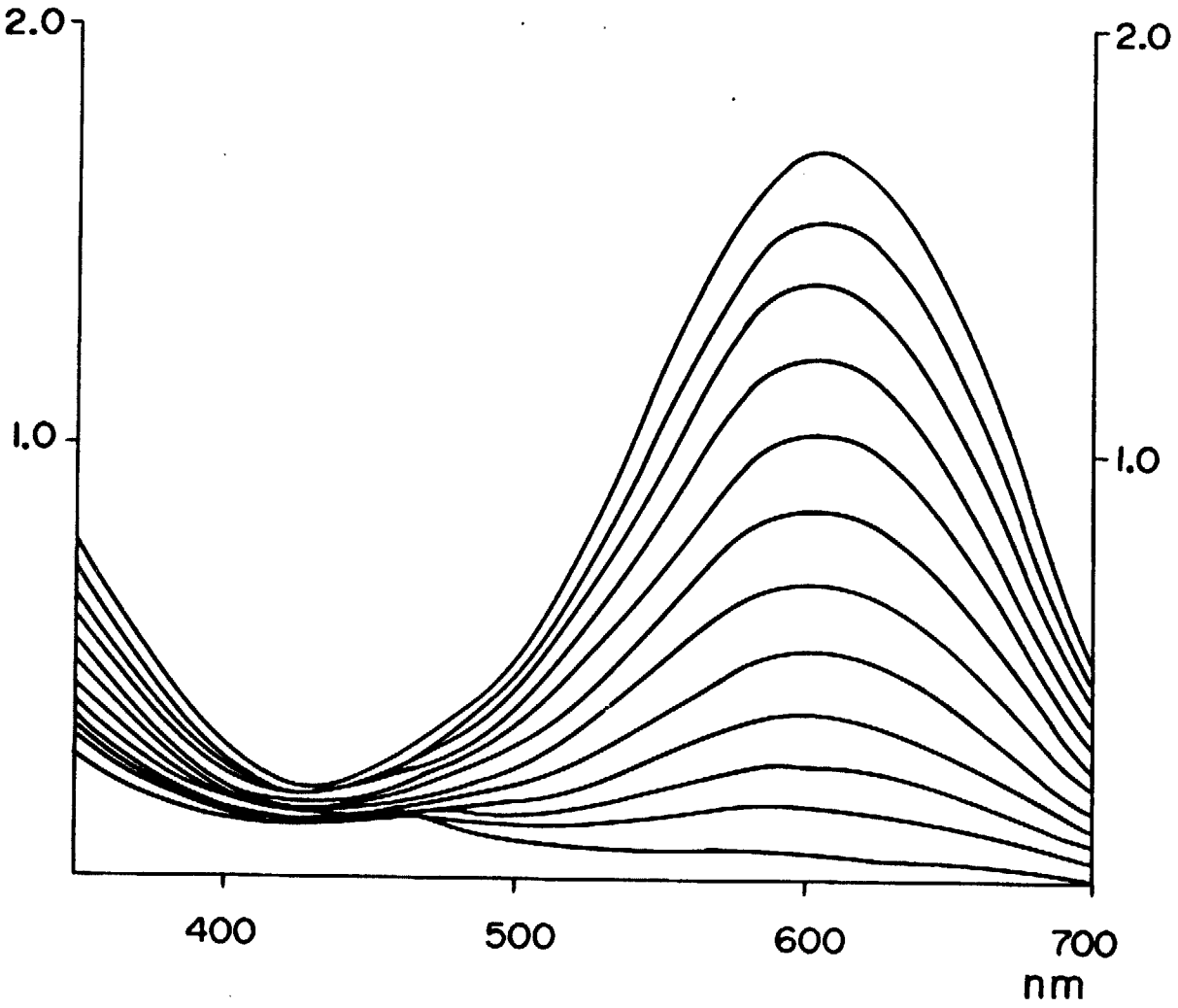
Figure 60:
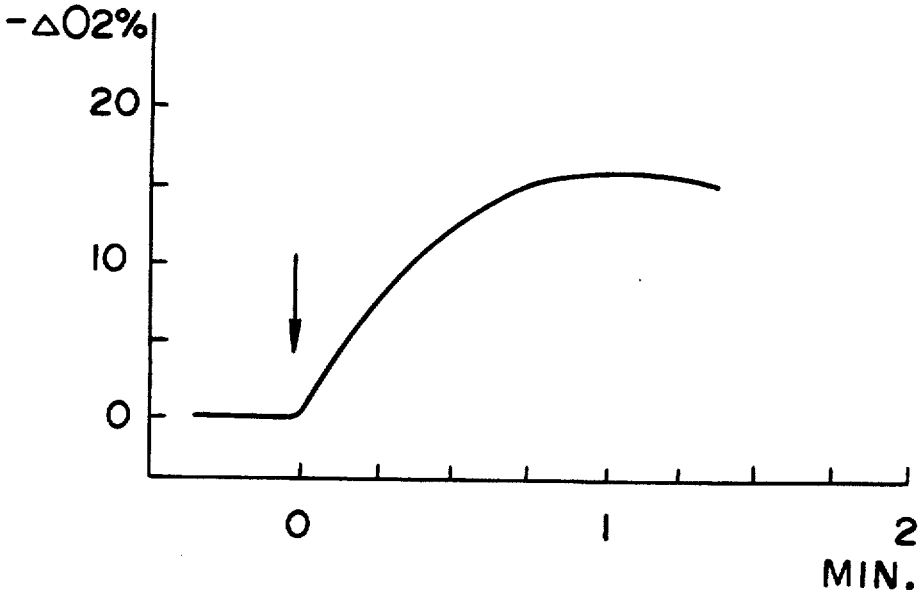
Figure 61:
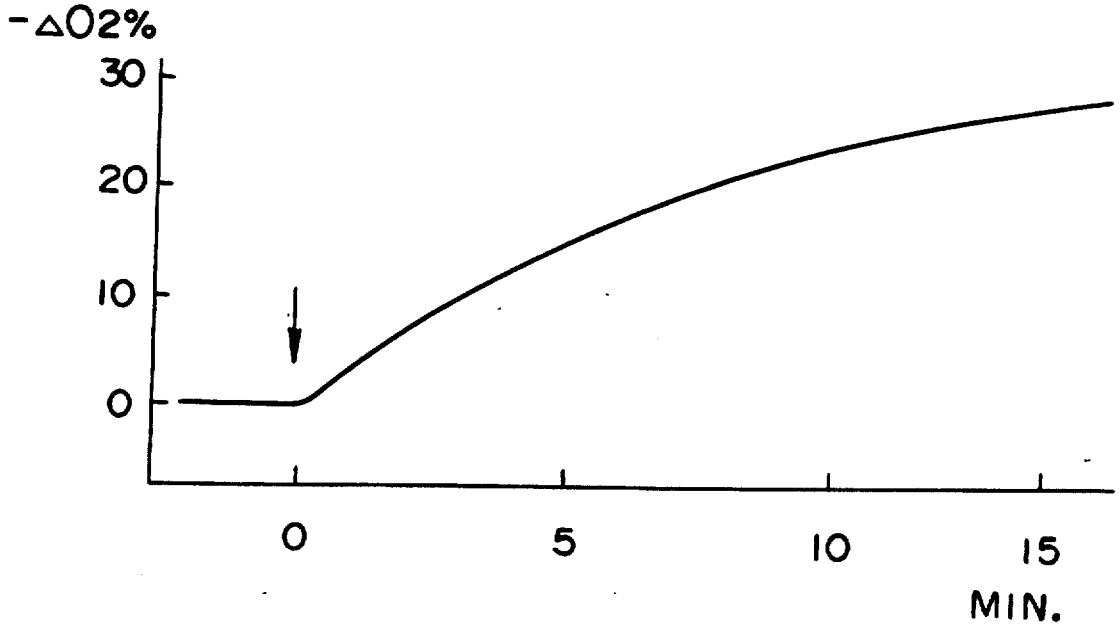

N,N-dimethyl-p-phenylenediamine: N,N-DMPD; thus:

FIG. 5: 2,6-DBAP, laccase and phenol;

FIG. 6: N,N-DEPD, ASOD and phenol;

FIG. 7: N,N-DMPD, ASOD and phenol;

FIG. 8: 2,6-DBAP, ASOD and o-methylaniline;

FIG. 9: 2,6-DBAP, ASOD and m-methylaniline;

FIG. 10: 2,6-DBAP, ASOD and 4-chloro-1-naphthol;

FIG. 11: 2,6-DBAP, ASOD and Clève's acid;

FIG. 12: 2,6-DBAP, ASOD and 1-hydroxy-2-naphthoic acid;

FIG. 13: N,N-DEPD, laccase and 1-naphthol-2-sulfonate;

FIG. 14: 2,6-DBAP, ASOD and o-chlorophenol;

FIG. 15: 2,6-DBAP, ASOD and m-aminophenol;

FIG. 16: 2,6-DBAP, ASOD and m-phenylenediamine;

FIG. 17: 2,6-DBAP, ASOD and 2,6-dibromophenol;

FIG. 18: 2,6-DBAP, ASOD and 2,6-dimethoxyphenol;

FIG. 19: 2,6-DBAP, ASOD and 3,5-dimethylphenol;

FIG. 20: 2,6-DBAP, ASOD and 2,6-dimethylphenol;

FIG. 21: 2,6-DBAP, ASOD and 2,4-dimethylphenol;

FIG. 22: 2,6-DBAP, ASOD and 2,3-dimethylphenol;

FIG. 23: 2,6-DBAP, ASOD and 2,5-dimethylphenol;

FIG. 24: 2,6-DBAP, ASOD and anthranilic acid;

FIG. 25: 2,6-DBAP, ASOD and N,N-dimethylaniline;

FIG. 26: 2,6-DBAP, ASOD and aniline;
FIG. 27: 2,6-DBAP, ASOD and m-chloroaniline;
FIG. 28: 2,6-DBAP, ASOD and o-aminophenol;
FIG. 29: N,N-DEPD, ASOD and o-chlorophenol;
FIG. 30: N,N-DEPD, ASOD and m-phenylenediamine;
FIG. 31: N,N-DEPD, ASOD and o-methylaniline;
FIG. 32: N,N-DEPD, ASOD and m-methylaniline;
FIG. 33: N,N-DEPD, ASOD and Clève's acid;
FIG. 34: N,N-DEPD, ASOD and 1-naphthol-2-sulfonate;
FIG. 35: N,N-DEPD, ASOD and 2,6-dibromophenol;
FIG. 36: N,N-DEPD, ASOD and 2,6-dimethoxyphenol;
FIG. 37: N,N-DEPD, ASOD and 2,6-dimethylphenol;
FIG. 38: N,N-DEPD, ASOD and 2,5-dimethylphenol;
FIG. 39: N,N-DEPD, ASOD and N,N-dimethylaniline;
FIG. 40: N,N-DEPD, ASOD and aniline;
FIG. 41: N,N-DMPD, ASOD and o-chlorophenol;
FIG. 42: N,N-DMPD, ASOD and 2,6-dibromophenol;
FIG. 43: N,N-DMPD, ASOD and anthranilic acid;
FIG. 44: N,N-DMPD, ASOD and aniline;
FIG. 45: N,N-DMPD, ASOD and α-naphthol;
FIG. 46: N,N-DMPD, ASOD and 4-chloro-1-naphthol;
FIG. 47: N,N-DMPD, ASOD and 1-naphthol-2-sulfonate;
FIG. 48: N,N-DMPD, ASOD and m-phenylenediamine;
FIG. 49: N,N-DMPD, ASOD and o-methylaniline;
FIG. 50: N,N-DMPD, ASOD and m-methylaniline;
FIG. 51: 2,6-DBAP, ASOD and m-bromoaniline;
FIG. 52: 2,6-DBAP, tyrosinase and N,N-ethyl-hydroxyethylanilin FIG. 53 is the standard curve of 2,6-DBAP using 1-naphthol-2-sulfonate and ASOD:

FIG. 54 is the standard curve of N,N-DEPD using phenol and ASOD;

FIG. 55 is the standard curve of phenol using N,N-diethyl-p-phenylenediamine and ASOD;

FIG. 56 is the standard curve of 2,6-DBAP using 2,5-dimethylphenol and ASOD;

FIG. 57 shows the changes in the absorption curve of pigment at 2-minute intervals during the reaction during α-glucosidase assay using phenol-α-glucoside and ASOD;

FIG. 58 shows the changes in the absorption curve of pigment at 5-minute intervals during the reaction during AlP assay using phenylphosphate and ASOD;

FIG. 59 shows the changes in the absorption curve of pigment at 2-minute intervals during the reaction during esterase assay using phenyl acetate and ASOD;

FIG. 60 is a graph of oxygen consumption ratio versus reaction time using 2,6-DBAP, 2,5-dimethylphenol and ASOD; and FIG. 61 is a graph of oxygen consumption ratio versus reaction time using 2,6-DBAP, 2,5-dimethylphenol and laccase.

The following examples illustrate the conditions, the compound [I], the uses, etc. of the present invention, but are not to be construed as limiting.

EXAMPLE 1

Figure 1:
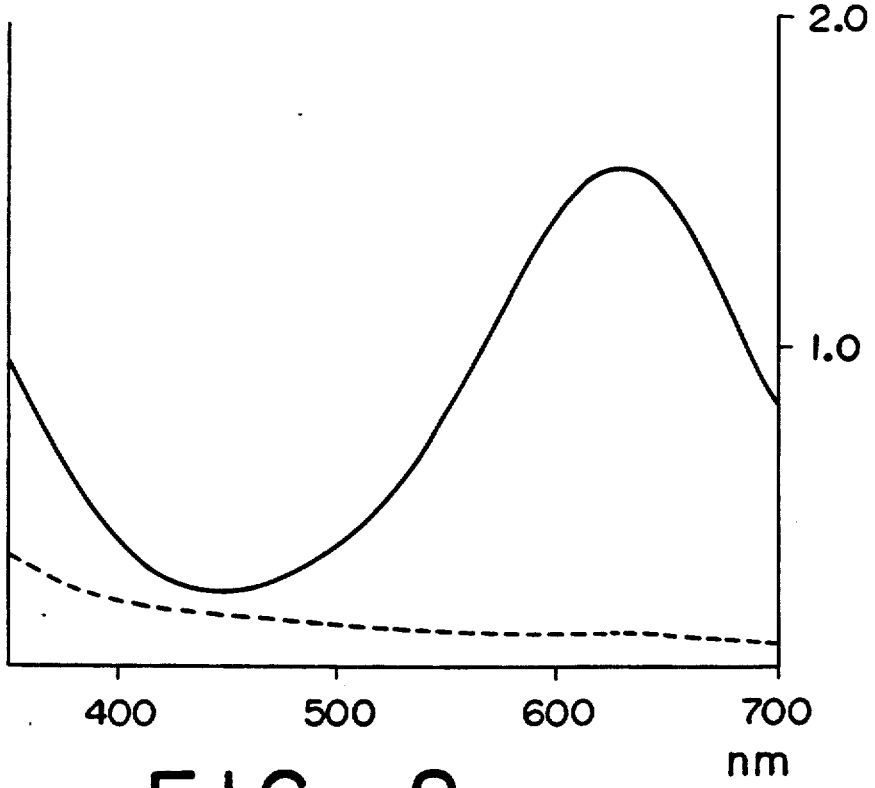
FIG. 1 is the absorption curve of pigment using 2,6-dibromo-4-aminophenol, ASOD and 1-naphthol-2-sulfonate (solid line)

Colorimetry using 2,6-dibromo-4-aminophenol, ascorbate oxidase (hereinafter called ASOD) and 1-naphthol-2-sulfonate:

2,6-dibromo-4-aminophenol hydrochloride was dissolved in a 0.1M phosphate buffer (pH 7.0) to prepare a 0.5 mM solution (solution A). 1-Naphthol-2-sulfonate was dissolved in a 0.1M phosphate buffer (pH 7.0) to prepare a 0.5 mM solution (solution B). ASOD (100 μl, 130 U) obtained from Sechium edule (Jap. Unexam. Pat. Publ. No. 56-88793) was added to a mixture of solution A (1.0 ml) and solution B (1.0 ml), and the mixture was incubated at 37° C. for 10 mins. The absorption wavelength of pigment formed is shown in FIG. 1 (solid line). A 0.1M phosphate buffer (pH 7.0) was used in place of solution B as a control. The results are shown in FIG. 1 (dotted line). The specific absorption maximum was found at 630 nm and thus 2,6-dibromo-4-aminophenol can be quantitatively measured.

The standard curve for 2,6-dibromo-4-aminophenol was prepared by incubating various concentrations of 2,6-dibromo-4-aminophenol (2 ml), 1-naphthol-2-sulfonate (0.5 mM, 1 ml) and ASOD (100 μl, 103 U) at 37° C. for 10 mins., and measuring at 630 nm (FIG. 53).

EXAMPLE 2

Colorimetry using 2,6-Dibromo-4-Aminophenol, ASOD and Phenol

In Example 1, potassium 1-naphthol-2-sulfonate was replaced by phenol (10 mM), but the other operations were performed in the same way.

Figure 2:
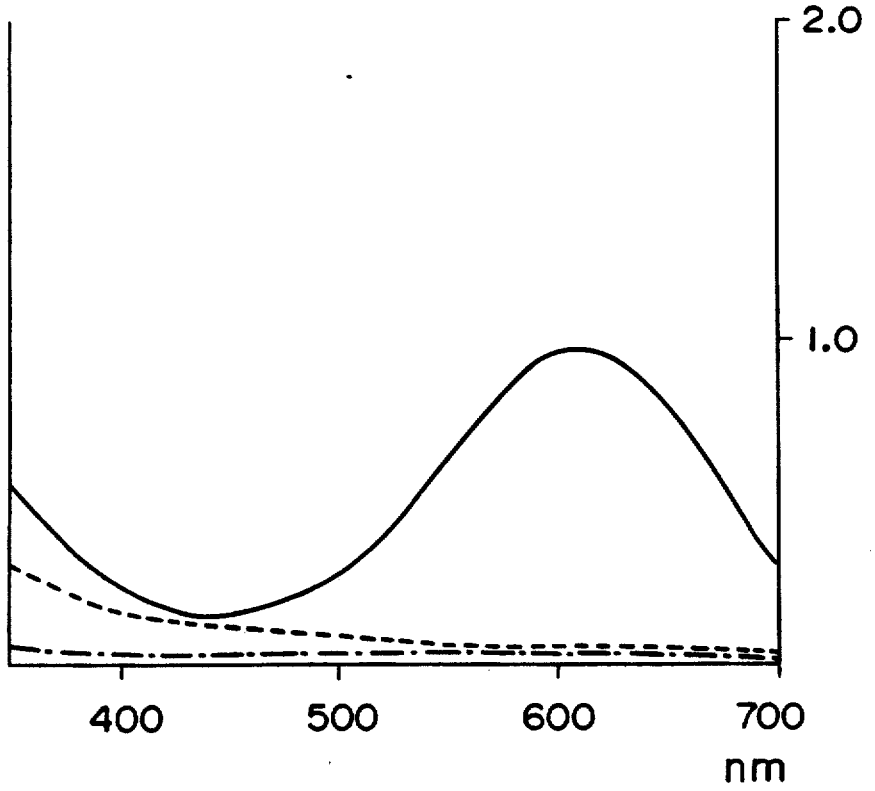
FIG. 2 is the absorption curve of pigment using 2,6-dibromo-4-aminophenol, ASOD and phenol (solid line)

The absorption curve of the pigment formed is shown in FIG. 2 (solid line). The absorption curve using a 0.1M phosphate buffer (pH 7.0) in place of phenol is shown in FIG. 2 (dotted line). 2,6-Dibromo-4-aminophenol can be measured by using ASOD and phenol at 610 nm.

Next, the 2,6-dibromo-4-aminophenol solution is replaced by 0.1M phosphate buffer (pH 7.0) to measure the absorption [FIG. 2 (—●—)].

As shown hereinabove, 2,6-dibromo-4-aminophenol or phenol can be quantitatively determined by the present method.

EXAMPLE 3

Colorimetry using 2,6-dibromo-4-aminophenol, laccase and 1-naphthol-2-sulfonate 2,6-Dibromo-4-aminophenol hydrochloride was dissolved in a 0.1M phosphate buffer (pH 7.0) to prepare a 0.5 mM solution (solution A). Potassium 1-naphthol-2-sulfonate was dissolved in a 0.1M phosphate buffer (pH 7.0) to prepare a 0.5 mM solution (solution B).

Laccase (100 μl, 80 U) obtained from Polyporus versicolor was added to a mixture of solutions A (1.0 ml) and B (1.0 ml) and the resulting mixture was incubated at 37° C. for 24 mins.

Figure 3:
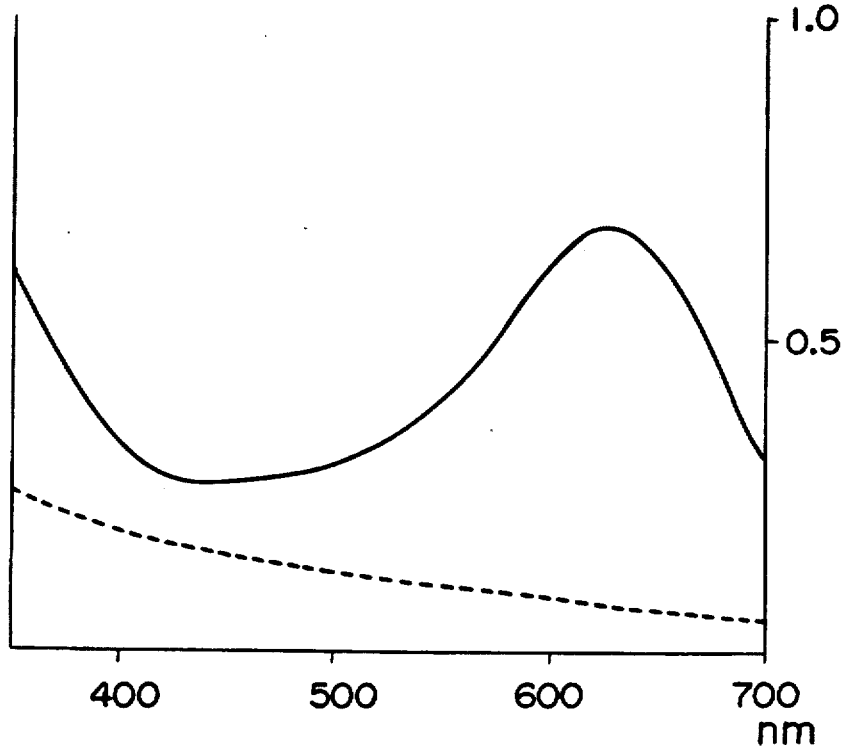
FIG. 3 is the absorption curve of pigment using 2,6-dibromo-4-aminophenol, laccase and 1-naphthol-2-sulfonate (solid line)

The absorption curve of the generated pigment is shown in FIG. 3 (solid line). As a control, potassium 1-naphthol-2-sulfonate was replaced by 0.1M phosphate buffer (pH 7.0). (FIG. 3, dotted line).

2,6-Dibromo-4-aminophenol can be quantitatively measured at 630 nm using laccase and potassium 1-naphthol-2-sulfonate.

EXAMPLE 4

Colorimetry using 2,6-Dibromo-4-Aminophenol, Laccase and 2,5-dimethylphenol

In Example 3, potassium 1-naphthol-2-sulfonate was replaced by 2,5-dimethylphenol (10 mM).

Figure 4:
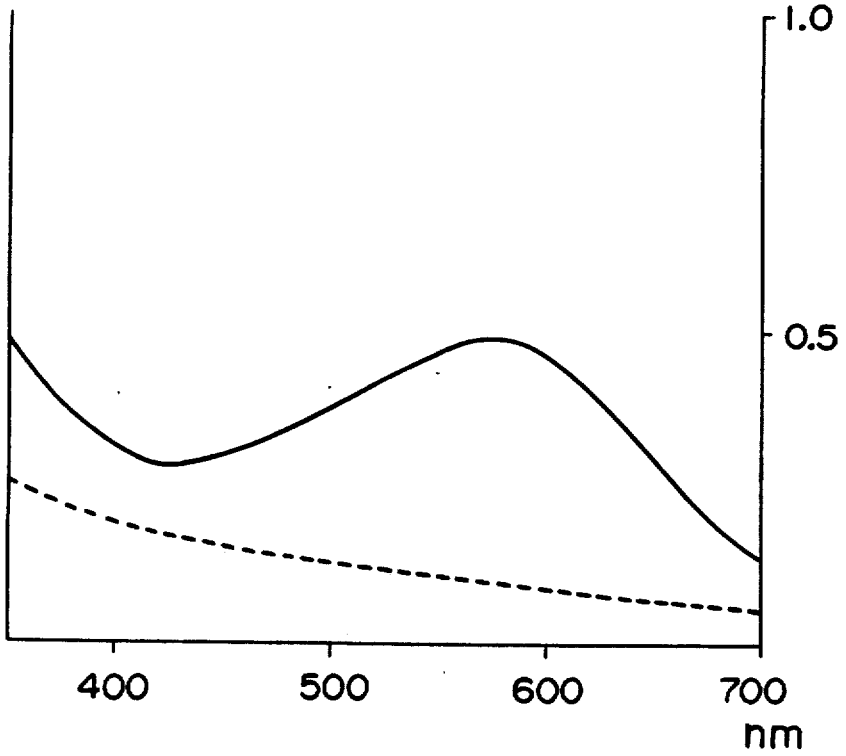
FIG. 4 is the absorption curve of pigment using 2,6-dibromo-4-aminophenol, laccase and 2,5-dimethylphenol (solid line)

The absorption curve of the generated pigment is shown in FIG. 4 (solid line). Also, results when 2,5-dimethylphenol is replaced by 0.1M phosphate buffer (pH 7.0) are shown in FIG. 4 (dotted line).

As illustrated hereinabove, 2,6-dibromo-4-aminophenol can be assayed by using laccase and 2,5-dimethylphenol.

The above laccase was replaced by tyrosinase (50 μl, 100 U) to obtain an absorption curve similar to FIG. 4 (specific absorption wavelength 585 nm, $\Delta OD_{585nm}=0.8$).

1 mM 2,6-dibromo-4-aminophenol and 10 mM 2,5-dimethylphenol in a 0.1M phosphate buffer (pH 7.0, 1 ml) was added to the incubation cell assembled with an oxygen electrode and preincubated at 37° C. ASOD solution (100 μl, 250 U) was added thereto and the mixture was incubated at 37° C. The electrochemical changes were measured with an oxygen electrode starting from zero time, that is, the time of ASOD addition, to measure the oxygen consumption ratio. The results are shown in FIG. 60.

ASOD hereinabove was replaced by laccase (100 μl, 200 U). The oxygen consumption ratio is shown in FIG. 61.

EXAMPLE 5

Colorimetry using 2,6-Dibromo-4-Aminophenol, Laccase and Phenol

In Example 3, potassium 1-naphthol-2-sulfonate was replaced by phenol (10 mM).

The absorption curve of the generated pigment is shown in FIG. 5 (solid line). Phenol was replaced by a 0.1M phosphate buffer (pH 7.0) (FIG. 5, dotted line).

As shown by the above, phenol or 2,6-dibromo-4-aminophenol can be assayed at 600 nm.

EXAMPLE 6

Colorimetry using N,N-Diethyl-p-Phenylenediamine, ASOD and Phenol

N,N-diethyl-p-phenylenediamine-dihydrochloride was dissolved in 0.1M phosphate buffer (pH 7.0) to prepare a 1 mM solution (solution A). Phenol was dissolved in a 0.1M phosphate buffer (pH 7.0) to prepare a 10 mM solution (solution B). ASOD (100 μl, 130 U) was added to the mixture of solution A (1.0 ml) and solution B (1.0 ml) and the mixture was incubated at 37° C. for 20 mins. The absorption curve of the generated pigment is shown in FIG. 6 (solid line). The same reaction, but in which the phenol solution was replaced by a 0.1M phosphate buffer (pH 7.0), was carried out. The results are shown in FIG. 6 (dotted line). As shown by the above, N,N-diethyl-p-phenylenediamine or phenol can be assayed at 670 nm.

The standard curve of the above can be prepared as follows:

Various concentrations of N,N-diethyl-p-phenylenediamine solution (2 ml), phenol (10 mM, 1.0 ml) and ASOD (100 μl, 130 U) were incubated at 37° C. for 10 mins. and colorimetrically measured at 670 nm to prepare the standard curve of N,N-diethyl-p-phenylenediamine (FIG. 54).

Various concentrations of phenol (1 ml), N,N-diethyl-p-phenylenediamine (1 mM, 2 ml) and ASOD (100 μl, 130 U) were incubated at 37° C. for 10 mins. and colorimetrically measured at 670 nm to prepare the standard curve of phenol (FIG. 55).

EXAMPLE 7

Colorimetry using N,N-Dimethyl-p-Phenylenediamine, ASOD and Phenol

In Example 6, N,N-diethyl-p-phenylenediamine dihydrochloride was replaced by N,N-dimethyl-p-phenylenediamine dihydrochloride and the mixture was incubated for 30 mins.

The absorption curve of the generated pigment is shown in FIG. 7 (solid line). Also, the phenol solution was replaced by a 0.1M phosphate buffer (pH 7.0) (FIG. 7, dotted line).

As shown by the above, N,N-dimethyl-p-phenylene diamine and phenol can be assayed at 655 nm.

EXAMPLE 8

Colorimetry using 2,6-Dibromo-4-Aminophenol, ASOD and o-methylaniline

In Example 1, potassium 1-naphthol-2-sulfonate was replaced by o-methylaniline (0.5 mM).

The absorption curve of the generated pigment is shown in FIG. 8 (solid line). Also a test in which o-methylaniline was replaced by 0.1M phosphate buffer (pH 7.0) is shown in FIG. 8 (dotted line).

As illustrated hereinabove, 2,6-dibromo-4-aminophenol can be assayed at 670 nm by using ASOD and o-methylaniline.

EXAMPLE 9

Colorimetry using 2,6-Dibromo-4-Aminophenol, ASOD and m-methylaniline

In Example 1, potassium 1-naphthol-2-sulfonate was replaced by m-methylaniline (0.5 mM).

The absorption curve of the generated pigment is shown in FIG. 9 (solid line). Also, a test conducted in which m-methylaniline was replaced by a 0.1M phosphate buffer (pH 7.0). The results are shown in FIG. 9 (dotted line).

As illustrated hereinabove, 2,6-dibromo-4-aminophenol can be assayed at 670 nm by using ASOD and m-methylaniline.

EXAMPLE 10

Colorimetry using 2,6-Dibromo-4-Aminophenol, ASOD and 4-chloro-1-naphthol

In Example 1, potassium 1-naphthol-2-sulfonate was replaced by 4-chloro-1-naphthol (0.5 mM).

The absorption curve of the generated pigment is shown in FIG. 10 (solid line). Also, the results when 4-chloro-1-naphthol was replaced by a 0.1M phosphate buffer (pH 7.0) are shown in FIG. 10 (dotted line).

As illustrated hereinabove, 2,6-dibromo-4-aminophenol can be assayed at 580 nm by using ASOD and 4-chloro-1-naphthol.

EXAMPLE 11

Colorimetry using 2,6-Dibromo-4-Aminophenol, ASOD and Clève's acid

In Example 1, potassium 1-naphthol-2-sulfonate was replaced by Clève's acid (0.5 mM).

The absorption curve of the generated pigment is shown in FIG. 11 (solid line). Also, the results when Clève's acid was replaced by a 0.1M phosphate buffer (pH 7.0) are shown in FIG. 11 (dotted line).

As illustrated hereinabove, 2,6-dibromo-4-aminophenol can be assayed at 560 nm by using ASOD and Clève's acid.

EXAMPLE 12

Colorimetry using 2,6-Dibromo-4-Aminophenol, ASOD and 1-Hydroxy-2-Naphthoic Acid In Example 1, potassium 1-naphthol-2-sulfonate was replaced by 1-hydroxy-2-naphthoic acid.

The absorption curve of the generated pigment is shown in FIG. 12 (solid line). Also, the results when 1-hydroxy-2-naphthoic acid was replaced by a 0.1M phosphate buffer (pH 7.0) are shown in FIG. 12 (dotted line).

As illustrated hereinabove, 2,6-dibromo-4-aminophenol can be assayed at 590 nm by using ASOD and 1-hydroxy-2-naphthoic acid.

EXAMPLE 13

Colorimetry using N,N-Diethyl-p-phenylenediamine, Laccase and 1-Naphthol-2-Sulfonate In Example 3, 2,6-diethyl-p-phenylenediamine.2HCl was replaced by N,N-diethyl-p-phenylenediamine.2HCl (1 mM).

The absorption curve of the generated pigment is shown in FIG. 13 (solid line). Also, the results when potassium 1-naphthol-2-sulfonate was replaced by 0.1M phosphate buffer (pH 7.0) are shown in FIG. 13 (dotted line).

As illustrated hereinabove, N,N-diethyl-p-phenylenediamine can be assayed at 660 nm by using laccase and potassium 1-naphthol-2-sulfonate.

EXAMPLE 14

Colorimetry using 2,6-Dibromo-4-Aminophenol, ASOD and o-chlorophenol

In Example 1, potassium 1-naphthol-2-sulfonate was replaced by o-chlorophenol (0.1 mM).

The absorption curve of the generated pigment is shown in FIG. 14 (solid line). Also, the results when o-chlorophenol was replaced by a 0.1M phosphate buffer (pH 7.0) are shown in FIG. 14 (dotted line).

As illustrated hereinabove, 2,6-dibromo-4-aminophenol can be assayed at 650 nm by using ASOD and o-chlorophenol.

EXAMPLE 15

Colorimetry using N,N-Dimethyl-p-phenylenediamine, ASOD and M-phenylenediamine:

In Example 1, potassium 1-naphthol-2-sulfonate was replaced by m-aminophenol (0.5 mM).

The absorption curve of the generated pigment is shown in FIG. 15 (solid line). Also, the results when m-aminophenol was replaced by a 0.1M phosphate buffer (pH 7.0) are shown in FIG. 15 (dotted line).

As illustrated hereinabove, 2,6-dibromo-4-aminophenol can be assayed at 565 nm by using ASOD and m-aminophenol.

EXAMPLE 16

Colorimetry Using N,N-diethyl-p-phenylenediamine, ASOD and m-phenylenediamine:

In Example 1, potassium 1-naphthol-2-sulfonate was replaced by m-phenylenediamine (0.5 mM).

The absorption curve of the generated pigment is shown in FIG. 16 (solid line). Also, the results when m-phenylenediamine was replaced by a 0.1M phosphate buffer (pH 7.0) are shown in FIG. 16 (dotted line).

As illustrated hereinabove, 2,6-dibromo-4-aminophenol can be assayed at 565 nm by using ASOD and m-phenylenediamine.

The absorption curve of the results when ASOD, m-phenylenediamine and phosphate buffer are used, is also shown in FIG. 16 (—●—).

EXAMPLE 17

Colorimetry using 2,6-Dibromo-4-Aminophenol, ASOD and 2,6-dibromophenol

In Example 1, potassium 1-naphthol-2-sulfonate was replaced by 2,6-dibromophenol:

The absorption curve of the generated pigment is shown in FIG. 17 (solid line). Also, the results when 2,6-dibromophenol was replaced by a 0.1M phosphate buffer (pH 7.0) are shown in FIG. 17 (dotted line).

As illustrated hereinabove, 2,6-dibromo-4-aminophenol can be assayed at 670 nm by using ASOD and 2,6-dibromophenol.

EXAMPLE 18

Colorimetry using 2,6-Dibromo-4-Aminophenol, ASOD and 2,6-Dimethoxyphenol

In Example 1, potassium 1-naphthol-2-sulfonate was replaced by 2,6-dimethoxyphenol (0.1 mM).

The absorption curve of the generated pigment is shown in FIG. 18 (solid line). Also, the results when 2,6-dimethoxyphenol was replaced by a 0.1M phosphate buffer (pH 7.0) are shown in FIG. 18 (dotted line).

As illustrated hereinabove, 2,6-dibromo-4-aminophenol can be assayed at 580 nm by using ASOD and 2,6-dimethoxyphenol.

EXAMPLE 19

Colorimetry using 2,6-Dibromo-4-Aminophenol, ASOD and 3,5-Dimethylphenol

In Example 1, potassium 1-naphthol-2-sulfonate was replaced by 3,5-dimethylphenol (0.5 mM).

The absorption curve of the generated pigment is shown in FIG. 19 (solid line). Also, the results when 3,5-dimethylphenol was replaced by a 0.1M phosphate buffer (pH 7.0) are shown in FIG. 19 (dotted line).

As illustrated hereinabove, 2,6-dibromo-4-aminophenol can be assayed at 620 nm by using ASOD and 3,5-dimethylphenol.

EXAMPLE 20

Colorimetry using 2,6-Dibromo-4-Aminophenol, ASOD and 2,6-Dimethylphenol

In Example 1, potassium 1-naphthol-2-sulfonate was replaced by 2,6-dimethylphenol (0.5 mM).

The absorption curve of the generated pigment is shown in FIG. 20 (solid line). Also, the results when 2,6-dimethylphenol was replaced by a 0.1M phosphate buffer (pH 7.0) are shown in FIG. 20 (dotted line).

As illustrated hereinabove, 2,6-dibromo-4-aminophenol can be assayed at 580 nm by using ASOD and 2,6-dimethylphenol.

EXAMPLE 21

Colorimetry using 2,6-Dibromo-4-Aminophenol, ASOD and 2,4-Dimethylphenol

In Example 1, potassium 1-naphthol-2-sulfonate was replaced by 2,4-dimethylphenol (0.5 mM).

The absorption curve of the generated pigment is shown in FIG. 21 (solid line). Also, the results when 2,4-dimethylphenol was replaced by 0.1M phosphate buffer (pH 7.0) are shown in FIG. 21 (dotted line).

As illustrated hereinabove, 2,6-dibromo-4-aminophenol can be assayed at 585 nm by using ASOD and 2,4-dimethylphenol.

EXAMPLE 22

Colorimetry using 2,6-Dibromo-4-Aminophenol, ASOD and 2,3-Dimethylphenol

In Example 1, potassium 1-naphthol-2-sulfonate was replaced by 2,3-dimethylphenol (0.5 mM).

The absorption curve of the generated pigment is shown in FIG. 22 (solid line). Also, the results when 2,3-dimethylphenol was replaced by a 0.1M phosphate buffer (pH 7.0) are shown in FIG. 22 (dotted line).

As illustrated hereinabove, 2,6-dibromo-4-aminophenol can be assayed at 590 nm by using ASOD and 2,3-dimethylphenol.

EXAMPLE 23

Colorimetry using 2,6-Dibromo-4-Aminophenol, ASOD and 2,5-Dimethylphenol

In Example 1, potassium 1-naphthol-2-sulfonate was replaced by 2,5-dimethylphenol (10 m).

The absorption curve of the generated pigment is shown in FIG. 23 (solid line). Also, the results when 2,5-dimethylphenol was replaced by 0.1M phosphate buffer (pH 7.0) are shown in FIG. 23 (dotted line).

As illustrated hereinabove, 2,6-dibromo-4-aminophenol can be assayed at 585 nm by using ASOD and 2,5-dimethylphenol.

Various concentrations of 2,6-dibromo-4-aminophenol (2 ml), 2,5-dimethylphenol (13.3 mM, 1 ml) and ASOD (100 μl, 130 U) are incubated at 37° C. for 10 mins., and colorimetrically measured at 585 nm to obtain the standard curve of 2,6-dibromo-4-aminophenol (FIG. 56).

EXAMPLE 24

Colorimetry using 2,6-Dibromo-4-Aminophenol, ASOD and Anthranilic Acid

In Example 1, potassium 1-naphthol-2-sulfonate was replaced by anthranilic acid (0.5 mM).

The absorption curve of the generated pigment is shown in FIG. 24 (solid line). Also, the results when anthranilic acid was replaced by a 0.1M phosphate buffer (pH 7.0) are shown in FIG. 24 (dotted line).

As illustrated hereinabove, 2,6-dibromo-4-aminophenol can be assayed at 640 nm by using ASOD and anthranilic acid.

EXAMPLE 25

Colorimetry using 2,6-Dibromo-4-Aminophenol, ASOD and N,N-Dimethylaniline

In Example 1, potassium 1-naphthol-2-sulfonate was replaced by N,N-dimethylaniline (0.5 mM).

The absorption curve of the generated pigment is shown in FIG. 25 (solid line). Also, the results when N,N-dimethylaniline was replaced by a 0.1M phosphate buffer (pH 7.0) are shown in FIG. 25 (dotted line).

As illustrated hereinabove, 2,6-dibromo-4-aminophenol can be assayed at 700 nm by using ASOD and N,N-dimethylaniline.

EXAMPLE 26

Colorimetry using 2,6-Dibromo-4-Aminophenol, ASOD and Aniline

In Example 1, potassium 1-naphthol-2-sulfonate was replaced by aniline (0.5 mM).

The absorption curve of the generated pigment is shown in FIG. 26 (solid line). Also, the results when aniline was replaced by a 0.1M phosphate buffer (pH 7.0) are shown in FIG. 26 (dotted line).

As illustrated hereinabove, 2,6-dibromo-4-aminophenol can be assayed at 630 nm by using ASOD and aniline.

EXAMPLE 27

Colorimetry using 2,6-Dibromo-4-Aminophenol, ASOD and m-Chloroaniline

In Example 1, potassium 1-naphthol-2-sulfonate was replaced by m-chloroaniline (0.5 mM).

The absorption curve of the generated pigment is shown in FIG. 27 (solid line). Also, the results when m-chloroaniline was replaced by a 0.1M phosphate buffer (pH 7.0) are shown in FIG. 27 (dotted line).

As illustrated hereinabove, 2,6-dibromo-4-aminophenol can be assayed at 635 nm by using ASOD and m-chloroaniline.

EXAMPLE 28

Colorimetry using 2,6-Dibromo-4-Aminophenol, ASOD and o-Aminophenol

In Example 1, potassium 1-naphthol-2-sulfonate was replaced by o-aminophenol (0.5 mM).

The absorption curve of the generated pigment is shown in FIG. 28 (solid line). Also, the results when o-aminophenol was replaced by a 0.1M phosphate buffer (pH 7.0) are shown in FIG. 28 (dotted line).

As illustrated hereinabove, 2,6-dibromo-4-aminophenol can be assayed at 580 nm by using ASOD and o-aminophenol.

The absorption curve of the reaction was ASOD and o-aminophenol is also shown in FIG. 28 (—●—).

EXAMPLE 29

Colorimetry using N,N-Diethyl-p-Phenylenediamine, ASOD and o-Chlorophenol

In Example 6, phenol was replaced by o-chlorophenol (0.1 mM).

The absorption curve of the generated pigment is shown in FIG. 29 (solid line). Also, the results when o-chlorophenol was replaced by a 0.1M phosphate buffer (pH 7.0) are shown in FIG. 29 (dotted line).

As illustrated hereinabove, N,N-diethyl-p-phenylenediamine can be assayed at 690 nm by using ASOD and o-chlorophenol.

EXAMPLE 30

Colorimetry using N,N-Diethyl-p-Phenylenediamine, ASOD and m-Phenylenediamine In Example 6, phenol was replaced by m-phenylenediamine (0.5 mM).

The absorption curve of the generated pigment is shown in FIG. 30 (solid line). Also, the results when m-phenylenediamine was replaced by a 0.1M phosphate buffer (pH 7.0) are shown in FIG. 30 (dotted line).

As illustrated hereinabove, N,N-diethyl-p-phenylenediamine can be assayed at 665 nm by using ASOD and m-phenylenediamine.

EXAMPLE 31

Colorimetry using N,N-Diethyl-p-Phenylenediamine, ASOD and o-Methylaniline

In Example 6, phenol was replaced by o-methylaniline (0.5 mM).

The absorption curve of the generated pigment is shown in FIG. 31 (solid line). Also, the results when o-methylaniline was replaced by a 0.1M phosphate buffer (pH 7.0) are shown in FIG. 31 (dotted line).

As illustrated hereinabove, N,N-diethyl-p-phenylenediamine can be assayed at 700 nm by using ASOD and o-methylaniline.

EXAMPLE 32

Colorimetry using N,N-Diethyl-p-Phenylenediamine, ASOD and m-Methylaniline

In Example 6, phenol was replaced by m-methylaniline (0.5 mM).

The absorption curve of the generated pigment is shown in FIG. 32 (solid line). Also the results when m-methylaniline was replaced by a 0.1M phosphate buffer (pH 7.0) are shown in FIG. 32 (dotted line).

As illustrated hereinabove, N,N-diethyl-p-phenylenediamine can be assayed at 710 nm by using ASOD and m-methylaniline.

EXAMPLE 33

Colorimetry using N,N-Diethyl-p-Phenylenediamine, ASOD and Clève's acid

In Example 6, phenol was replaced by Clève's acid (0.5 mM).

The absorption curve of the generated pigment is shown in FIG. 33 (solid line). Also, the results when Clève's acid was replaced by a 0.1M phosphate buffer (pH 7.0) are shown in FIG. 33 (dotted line).

As illustrated hereinabove, N,N-diethyl-p-phenylenediamine can be assayed at 755 nm by using ASOD and Clève's acid.

EXAMPLE 34

Colorimetry using N,N-Diethyl-p-Phenylenediamine, ASOD and 1-Naphthol-2-Sulfonate In Example 6, phenol was replaced by potassium 1-naphthol-2-sulfonate (0.5 mM).

The absorption curve of the generated pigment is shown in FIG. 34 (solid line). Also, the results when potassium 1-naphthol-2-sulfonate was replaced by a 0.1M phosphate buffer (pH 7.0) are shown in FIG. 34 (dotted line).

As illustrated hereinabove, N,N-diethyl-p-phenylenediamine can be assayed at 655 nm by using ASOD and potassium 1-naphthol-2-sulfonate.

EXAMPLE 35

Colorimetry using N,N-Diethyl-p-Phenylenediamine, ASOD and 2,6-Dibromophenol

In Example 6, phenol was replaced by 2,6-dibromophenol (0.5 mM).

The absorption curve of the generated pigment is shown in FIG. 35 (solid line). Also, the results when 2,6-dibromophenol was replaced by a 0.1M phosphate buffer (pH 7.0) are shown in FIG. 35 (dotted line).

As illustrated hereinabove, N,N-diethyl-p-phenylenediamine can be assayed at 700 nm by using ASOD and 2,6-dibromophenol.

EXAMPLE 36

Colorimetry using N,N-Diethyl-p-Phenylenediamine, ASOD and 2,6-Dimethoxyphenol

In Example 6, phenol was replaced by 2,6-dimethoxyphenol (0.5 mM).

The absorption curve of the generated pigment is shown in FIG. 26 (solid line). Also, the results when 2,6-dimethoxyphenol was replaced by a 0.1M phosphate buffer (pH 7.0) are shown in FIG. 36 (dotted line).

As illustrated hereinabove, N,N-diethyl-p-phenylenediamine can be assayed at 630 nm by using ASOD and 2,6-dimethoxyphenol.

The absorption curve of the reaction with ASOD and 2,6-dimethoxyphenol is also shown in FIG. 36 (— ● —).

EXAMPLE 37

Colorimetry using N,N-Diethyl-p-Phenylenediamine, ASOD and 2,6-Dimethylphenol

In Example 6, phenol was replaced by 2,6-dimethylphenol (10 mM).

The absorption curve of the generated pigment is shown in FIG. 37 (solid line). Also, the results when 2,6-dimethylphenol was replaced by a 0.1M phosphate buffer (pH 7.0) are shown in FIG. 37 (dotted line).

As illustrated hereinabove, N,N-diethyl-p-phenylenediamine can be assayed at 630 nm by using ASOD and 2,6-dimethylphenol.

EXAMPLE 38

Colorimetry using N,N-Diethyl-p-Phenylenediamine, ASOD and 2,5-Dimethylphenol

In Example 6, phenol was replaced by 2,5-dimethylphenol (10 mM).

The absorption curve of the generated pigment is shown in FIG. 38 (solid line). Also, the results when 2,5-dimethylphenol was replaced by a 0.1M phosphate buffer (pH 7.0) are shown in FIG. 38 (dotted line).

As illustrated hereinabove, N,N-diethyl-p-phenylenediamine can be assayed at 640 nm by using ASOD and 2,5-dimethylphenol.

EXAMPLE 39

Colorimetry using N,N-Diethyl-p-Phenylenediamine, ASOD and N,N-Dixethylaniline

In Example 6, phenol was replaced by N,N-dimethylaniline (0.5 mM).

The absorption curve of the generated pigment is shown in FIG. 39 (solid line). Also, the results when N,N-dimethylaniline was replaced by a 0.1M phosphate buffer (pH 7.0) are shown in FIG. 39 (dotted line).

As illustrated hereinabove, N,N-diethyl-p-phenylenediamine can be assayed at 730 nm by using ASOD and N,N-dimethylaniline.

EXAMPLE 40

Colorimetry using N,N-Diethyl-p-Phenylenediamine, ASOD and Aniline

In Example 6, phenol was replaced by aniline (0.5 mM).

The absorption curve of the generated pigment is shown in FIG. 40 (solid line). Also, the results when aniline was replaced by a 0.1M phosphate buffer (pH 7.0) are shown in FIG. 40 (dotted line).

As illustrated hereinabove, N,N-diethyl-p-phenylenediamine can be assayed at 690 nm by using ASOD and aniline.

The absorption curve of the reaction of ASOD and aniline is also shown in FIG. 40 (—●—).

EXAMPLE 41

Colorimetry using N,N-Dimethyl-p-Phenylenediamine, ASOD and o-chlorophenol:

In Example 7, phenol was replaced by o-chlorophenol (0.1 mM).

The absorption curve of the generated pigment is shown in FIG. 41 (solid line). Also, the results when o-chlorophenol was replaced by a 0.1M phosphate buffer (pH 7.0) are shown in FIG. 41 (dotted line).

As illustrated hereinabove, N,N-dimethyl-p-phenylenediamine can be assayed at 680 nm by using ASOD and o-chlorophenol.

EXAMPLE 42

Colorimetry using N,N-Dimethyl-p-Phenylenediamine, ASOD and 2,6-Dibromophenol In Example 7, phenol was replaced by 2,6-dibromophenol (0.5 mM).

The absorption curve of the generated pigment is shown in FIG. 42 (solid line). Also, the results when 2,6-dibromophenol was replaced by a 0.1M phosphate buffer (pH 7.0) are shown in FIG. 42 (dotted line).

As illustrated hereinabove, N,N-dimethyl-p-phenylenediamine can be assayed at 695 nm by using ASOD and 2,6-dibromophenol.

EXAMPLE 43

Colorimetry using N,N-Dimethyl-p-Phenylenediamine, ASOD and Anthranilic Acid In Example 7, phenol was replaced by anthranilic acid (0.5 mM).

The absorption curve of the generated pigment is shown in FIG. 43 (solid line). Also, the results when anthranilic acid was replaced by a 0.1M phosphate buffer (pH 7.0) are shown in FIG. 43 (dotted line).

As illustrated hereinabove, N,N-dimethyl-p-phenylenediamine can be assayed at 680 nm by using ASOD and anthranilic acid.

EXAMPLE 44

Colorimetry using N,N-Dimethyl-p-Phenylenediamine, ASOD and Aniline

In Example 7, phenol was replaced by aniline.

The absorption curve of the generated pigment is shown in FIG. 44 (solid line). Also, the results in which aniline was replaced by a 0.1M phosphate buffer (pH 7.0) are shown in FIG. 44 (dotted line).

As illustrated hereinabove, N,N-dimethyl-p-phenylenediamine can be assayed at 690 nm by using ASOD and aniline.

EXAMPLE 45

Colorimetry using N,N-Dimethyl-p-Phenylenediamine, ASOD and 2-Naphthol

In Example 7, phenol was replaced by 2-naphthol (0.5 mM).

The absorption curve of the generated pigment is shown in FIG. 45 (solid line). Also, the results when 2-naphthol was replaced by a 0.1M phosphate buffer (pH 7.0) are shown in FIG. 45 (dotted line).

As illustrated hereinabove, N,N-dimethyl-p-phenylenediamine can be assayed at 630 nm by using ASOD and 2-naphthol.

EXAMPLE 46

Colorimetry Using N,N-dimethyl-p-phenylenediamine, ASOD and 4-chloro-1-naphthol In Example 7, phenol was replaced by 4-chloro-1-naphthol (0.5 mM).

The absorption curve of the generated pigment is shown in FIG. 46 (solid line). Also, the results when 4-chloro-1-naphthol was replaced by a 0.1M phosphate buffer (pH 7.0) are shown in FIG. 46 (dotted line).

As illustrated hereinabove, N,N-dimethyl-p-phenylenediamine can be assayed at 640 nm by using ASOD and 4-chloro-1-naphthol.

EXAMPLE 47

Colorimetry Using N,N-dimethyl-p-phenylenediamine, ASOD and 1-naphthol-2-sulfonate In Example 7, phenol was replaced by potassium 1-naphthol-2-sulfonate (0.5 mM).

The absorption curve of the generated pigment is shown in FIG. 47 (solid line). Also, the results when potassium 1-naphthol-2-sulfonate was replaced by a 0.1M phosphate buffer (pH 7.0) are shown in FIG. 47 (dotted line).

As illustrated hereinabove, N,N-dimethyl-p-phenylenediamine can be assayed at 650 nm by using ASOD and potassium 1-naphthol-2-sulfonate.

EXAMPLE 48

Colorimetry Using N,N-dimethyl-p-phenylenediamine, ASOD and m-phenylenediamine In Example 7, phenol was replaced by m-phenylenediamine (0.5 mM).

The absorption curve of the generated pigment is shown in FIG. 48 (solid line). Also, the results when m-phenylenediamine was replaced by a 0.1M phosphate buffer (pH 7.0) are shown in FIG. 48 (dotted line).

As illustrated hereinabove, N,N-dimethyl-p-phenylenediamine can be assayed at 650 nm by using ASOD and m-phenylenediamine.

EXAMPLE 49

Colorimetry Using N,N-dimethyl-p-phenylenediamine, ASOD and o-methylaniline

In Example 7, phenol was replaced by o-methylaniline (0.5 mM).

The absorption curve of the generated pigment is shown in FIG. 49 (solid line). Also, the results when o-methylaniline was replaced by a 0.1M phosphate buffer (pH 7.0) are shown in FIG. 49 (dotted line).

As illustrated hereinabove, N,N-dimethyl-p-phenylenediamine can be assayed at 695 nm by using ASOD and o-methylaniline.

EXAMPLE 50

Colorimetry Using N,N-dimethyl-p-phenylenediamine, ASOD and m-methylaniline

In Example 7, phenol was replaced by m-methylaniline (0.5 mM).

The absorption curve of the generated pigment is shown in FIG. 50 (solid line). Also, the results when m-methylaniline was replaced by a 0.1M phosphate buffer (pH 7.0) are shown in FIG. 50 (dotted line).

As illustrated hereinabove, N,N-dimethyl-p-phenylenediamine can be assayed at 705 nm by using ASOD and m-methylaniline.

EXAMPLE 51

Colorimetry Using 2,6-dibromo-4-aminophenol, ASOD and m-bromoaniline

In Example 1, potassium 1-naphthol-2-sulfonate was replaced by m-bromoaniline (0.5 mM).

The absorption curve of the generated pigment is shown in FIG. 51 (solid line). Also, the results when m-bromoaniline was replaced by a 0.1M phosphate buffer (pH 7.0) are shown in FIG. 51 (dotted line).

As illustrated hereinabove, 2,6-dibromo-4-aminophenol can be assayed at 635 nm by using ASOD and m-bromoaniline.

EXAMPLE 52

Colorimetry Using 2,6-dibromo-4-aminophenol, tyrosinase and N,N-ethyl-hydroxyethylaniline 2,6-dibromo-4-aminophenol hydrochloride was dissolved in a 0.1M phosphate buffer (pH 7.0) to prepare a 0.05M solution (solution A). N,N-ethyl-hydroxyethylaniline was dissolved in a 0.1M phosphate buffer (pH 7.0) to prepare a 5 mM solution (solution B). A tyrosinase solution (50 μl, 100 U) was added to a mixture of solution A (1.0 ml) and B (1.0 ml), and the mixture was incubated at 37° C. for 10 mins.

The absorption curve of the generated pigment is shown in FIG. 52, in which the specific absorption is at 705 nm, and 2,6-dibromo-4-aminophenol can be assayed at 705 nm.

Pigments showing the same specific absorption was obtained using ASOD and laccase, respectively, in place of tyrosinase.

EXAMPLE 53

Colorimetry Using 2,6-dibromo-4-aminophenol, ASOD and m-chlorophenol

In Example 1, potassium 1-naphthol-2-sulfonate was replaced by m-chlorophenol (0.1 mM).

The absorption maximum of the generated pigment was at approximately 650 nm. As a result, 2,6-dibromo-p-aminophenol can be assayed at 650 nm using ASOD and m-chlorophenol.

EXAMPLE 54

Colorimetry Using 2,6-dibromo-4-aminophenol, ASOD and o-chloroaniline

In Example 1, potassium 1-naphthol-2-sulfonate was replaced by o-chloroaniline (0.5 mM).

The absorption maximum of the generated pigment was at approximately 630 nm. As a result, 2,6-dibromo-p-aminophenol can be assayed at 630 nm using ASOD and o-chloroaniline.

EXAMPLE 55

Colorimetry Using 2,6-dibromo-4-aminophenol, ASOD and p-chlorophenol

In Example 1, potassium 1-naphthol-2-sulfonate was replaced by p-chlorophenol (1 mM).

The absorption maximum of the generated pigment was at approximately 620 nm. As a result, 2,6-dibromo-p-aminophenol can be assayed at 620 nm using ASOD and p-chlorophenol.

EXAMPLE 56

Colorimetry Using 2,6-dibromo-4-aminophenol, ASOD and p-bromophenol

In Example 1, potassium 1-naphthol-2-sulfonate was replaced by p-bromophenol (1 mM).

The absorption maximum of the generated pigment was at approximately 600 nm. As a result, 2,6-dibromo-p-aminophenol can be assayed at 600 nm using ASOD and p-bromophenol.

EXAMPLE 57

Colorimetry Using 2,6-dibromo-4-aminophenol, ASOD and 2,4-dichlorophenol

In Example 1, potassium 1-naphthol-2-sulfonate was replaced by 2,4-dichlorophenol (0.1 mM).

The absorption maximum of the generated pigment was at approximately 660 nm. As a result, 2,6-dibromo-p-aminophenol can be assayed at 660 nm using ASOD and 2,4-dichlorophenol.

EXAMPLE 58

Colorimetry Using 2,6-dibromo-4-aminophenol, ASOD and 2,-4-dibromophenol

In Example 1, potassium 1-naphthol-2-sulfonate was replaced by 2,4-dibromophenol (1 mM).

The absorption maximum of the generated pigment was at approximately 660 nm. As a result, 2,6-dibromo-p-aminophenol can be assayed at 660 nm using ASOD and 2,4-dibromophenol.

EXAMPLE 59

Colorimetry Using N,N-diethyl-p-phenylenediamine, ASOD and α-naphthol

In Example 6, phenol was replaced by α-naphthol (0.5 mM).

The absorption maximum of the generated pigment was at approximately 620 nm. As a result, N,N-diethyl-p-phenylenediamine can be assayed at 620 nm using ASOD and α-naphthol.

EXAMPLE 60

Colorimetry Using N,N-diethyl-p-phenylenediamine, ASOD and m-chlorophenol

In Example 6, phenol was replaced by m-chlorophenol (0.5 mM).

The absorption maximum of the generated pigment was at approximately 695 nm. As a result, N,N-diethyl-p-phenylenediamine can be assayed at 695 nm using ASOD and m-chlorophenol.

EXAMPLE 61

Colorimetry Using N,N-diethyl-p-phenylenediamine, ASOD and 2,3-dimethylphenol In Example 6, phenol was replaced by 2,3-dimethylphenol (10 mM).

The absorption maximum of the generated pigment was at approximately 625 nm. As a result, N,N-diethyl-p-phenylenediamine can be assayed at 625 nm using ASOD and 2,3-dimethylphenol.

EXAMPLE 62

Colorimetry Using N,N-diethyl-p-phenylenediamine, ASOD and Anthranilic Acid

In Example 6, phenol was replaced by anthranilic acid (0.5 mM).

The absorption maximum of the generated pigment was at approximately 680 nm. As a result, N,N-dimethyl-p-phenylenediamine can be assayed at 680 nm using ASOD and anthranilic acid.

EXAMPLE 63

Colorimetry Using N,N-diethyl-p-phenylenediamine, ASOD and 2,4-dimethylphenol

In Example 6, phenol was replaced by 2,4-dimethylphenol (10 mM).

The absorption maximum of the generated pigment was at approximately 630 nm. As a result, N,N-diethyl-p-phenylenediamine can be assayed at 630 nm using ASOD and 2,4-dimethylphenol.

EXAMPLE 64

Colorimetry Using N,N-dimethyl-p-phenylenediamine, ASOD and N,N-dimethylaniline

In Example 7, phenol was replaced by N,N-dimethylaniline (0.5 mM).

The absorption maximum of the generated pigment was at approximately 725 nm. As a result, N,N-dimethyl-p-phenylenediamine can be assayed at 725 nm using ASOD and N,N-dimethylaniline.

EXAMPLE 65

Assay Method of CAP

S-Benzyl-L-cysteinyl-p-dimethylaminoanilide (100 mg), obtained by a conventional dehydration condensation of N,N-dimethyl-p-phenylenediamine.2 HCl, N-benzyloxycarbonyl-S-benzyl-L-cysteine and dicyclohexylcarbodiimide, followed by removing the protective group, was dissolved in a mixture of dioxane (3 ml) and 0.16N-HCl, and mixed with 0.1M triethanolaminecitrate buffer (pH 7.4, 100 ml) containing 1.25% Tween 80 (surface active agent) to prepare a synthetic substrate solution. The substrate solution (2 ml), p-xylenol (5 mM, 0.1 ml) and laccase (2000 U/ml, 100 μl) were mixed in a cell for colorimetry and the mixture was preincubated at 37° C. Pregnant serum containing CPA (238 mU/ml) was admixed therein to start the reaction. The absorption ratio after 30 mins. measured at 600 nm was $O.D._{600}=0.18$. As a result, CAP assay can desirably be performed by this method.

EXAMPLE 66

Assay Method of CAP

In Example 65, N,N-dimethyl-p-phenylenediamine.2HCl was replaced by 3,5-dibromo-4-hydroxyaniline to prepare S-benzyl-L-cysteine-3,5-dibromo-4-hydroxyanilide, and the remaining procedure was conducted the same as in Example 65.

The absorption ratio after 30 mins. was measured at 585 nm to obtain $O.D._{585}=0.195$. As a result, CAP assay can desirably be performed by this method.

EXAMPLE 67

In Example 66, laccase was replaced by ASOD (1320 U/ml) and the remaining procedure was conducted as in that example. $O.D._{585}=0.175$ was obtained. CAP assay can desirably be performed by this method.

EXAMPLE 68

In Example 65, N,N-dimethyl-p-phenylenediamine.2HCl was replaced by N,N-diethyl-p-phenylenediamine to obtain S-benzyl-L-crysteinyl-p-diethylaminoanilide, and p-xylenol (5 mM) was replaced by 1-naphthol-2-sulfonate (2 mM). The absorbency was measured at 655 nm to obtain $O.D._{655}=0.205$. CAP assay can desirably be performed by this method.

EXAMPLE 69

Assay of α-chymotrypsin p-Dimethylaminoaniline.2HCl and N-benzyloxycarbonyl-L-tyrosine were condensed with dicyclohexylcarbodiimide, and the protective group was removed by palladium-carbon catalyst, then the resulting compound was reacted with benzoylchloride to obtain as a synthetic substrate N-benzoyl-L-tyrosinyl-p-dimethylaminoanilide. The synthetic substrate (30 mg) was dissolved in acetone (5 ml) to prepare an original substrate solution. 0.1M Tris-HCl buffer (pH 7.8, 100 ml) (containing 5 mM calcium chloride and 1% Tween 80) was added to the original solution to prepare a substrate solution.

The substrate solution (2 ml), p-xylenol (15 mM, 0.1 ml) and laccase (2000 U/ml, 100 μl) were mixed well in a colorimetric cell, and the mixture was preincubated at a constant temperature of 37° C. α-Chymotrypsin (3 mg/ml, 50 μl) was added thereto to start the reaction. The absorbency after 30 mins. was measured at 600 nm to obtain $O.D._{600}=0.48$. As a result, α-chymotrypsin can desirably be assayed by this method.

EXAMPLE 70

Assay Method of Trypsin

N-benzyloxycarbonyl-L-tryptophan and N,N-diethyl-p-phenylenediamine were condensed with dicyclohexylcarbodiimide under ice cooling, and the protective group was removed by palladium-carbon catalyst, then the product was acetylated with acetic anhydride to obtain N-acetyl-L-tryptophan-p-diethylaminoanilide. This compound (30 mg) was dissolved in acetone (5 ml) to prepare an original substrate solution. 0.1M Tris-HCl buffer (pH 7.8, 100 ml, containing 5 mM calcium chloride and 1% Tween 80) was added to prepare the synthetic substrate solution.

The synthetic substrate solution (2 ml), 1-naphthol-2-sulfonate (2 mM, 0.1 ml) and laccase (2000 U/ml), 100 μl) were mixed well in a colorimetric cell and the mixture was preincubated at a constant temperature of 37° C. Trypsin (50 μl) was added thereto to start the reaction. The absorbency after 30 mins. was measured at 655 nm to obtain $O.D._{655}=0.38$. As a result, trypsin can desirably be assayed by this method.

EXAMPLE 71

Assay Method of α-chymotrypsin

In Example 69, p-dimethylaminoaniline 2HCl was replaced by p-diethylaminoaniline to obtain N-benzyl-L-tyrosinyl-p-diethylaminoanilide. This compound (30 mg) was dissolved in acetone (5 ml) to prepare an original substrate solution. The substrate solution was prepared the same way as in Example 69.

Then, in Example 69, p-xylenol (5 mM) was replaced by 1-naphthyl-2-sulfonate (2 mM) and the absorbency was measured at 655 nm to obtain $O.D._{655}=0.52$. As a result, α-chymotrypsin can desirably be assayed by this method.

EXAMPLE 72

Assay Method of α-chymotrypsin 3,5-Dibromo-4-hydroxyaniline and N-benzyloxycarbonyl-L-tyrosine were condensed by a conventional dehydration condensation with dicyclohexylcarbodiimide and the protective group was removed by palladium-carbon catalyst, then the product was reacted with benzoylchloride to obtain a synthetic substrate comprising N-benzoyl-L-tyrosine-3,5-dibromo-4-hydroxyanilide. The synthetic substrate (30 mg) was dissolved in acetone (5 ml) to prepare the original substrate solution. 0.1M Trist-HCl buffer (pH 7.8, 100 m containing 5 mM calcium chloride and 1% Tween 80) was added thereto to prepare the substrate solution.

The substrate solution (2 ml), p-xylenol (5 mM, 0.1 ml) and laccase (2000 U/ml, 100 μl) were mixed well in a colorimetric cell and the mixture was preincubated at a constant temperature of 37° C. α-Chymotrypsin (3 mg/ml, 50 μl) was added to start the reaction. The absorbency after 39 mins. was measured at 585 nm ($O.D._{585}=0.465$). As a result, α-chymotrypsin can desirably be measured by this method.

EXAMPLE 73

Assay Method of α-chymotrypsin

In Example 72, laccase was replaced by ASOD (1320 U/ml, 100 μl) to obtain the absorption ratio $O.D._{585}=0.452$. As a result, α-chymotrypsin can desirably be measured by this method.

EXAMPLE 74

α-Glucosidase Assay Using phenyl-α-D-glucoside and ASOD

Phenyl-α-D-glucoside (Nakarai Chem. Co.) (0.24 mM) dissolved in a 0.1M phosphate buffer (pH 7.0, 2 ml), 2,6-dibromo-4-aminophenol (1 mM, 1 ml) and ASOD obtained from Sechium edule (1320 U/ml, 100 μl) were mixed in a colorimetric cell and preincubated to constant temperature at 30° C. α-Glucosidase (Toyobo Co., 3000 U/ml, 10 μl) was added thereto to start the reaction, and changes of absorption wavelength were recorded every 2 mins. The result are shown in FIG. 57. As a result, α-glucosidase activity can be assayed at 610 nm by reacting with liberated phenol from substrate phenyl-α-D-glucosidase, ASOD and a coupler.

EXAMPLE 75

Assay Method of α-amylase

A hydroxyl group in maltopentaose was conventionally acetylated with sodium acetate and acetic anhydride. The thus-obtained maltopentaose-β-heptadeca acetate was mixed with phenol and anhydrous zinc chloride to effect a coupling reaction. The obtained α- and β-phenylhexadeca acetylmaltopentaoside was deacetylated in a sodium methoxide solution in methanol. The phenyl hexadecamaltopentaoside thus obtained was dissolved in a 0.05M glycerophosphate buffer (pH 7.0) containing 2% α-cyclodextrin to prepare a 0.4% substrate solution. An enzyme solution (50 μl) containing α-glucosidase (500 U/ml) and β-glucosidase (100 U/ml), 2,6-dibromo-4-aminophenol (5 mM, 50 μl) and laccase (2000 U/ml, 100 μl) was thoroughly mixed in a colorimetric cell and the mixture was preincubated at 37° C. α-Amylase (Boehringer g.m.b.H., 5000 I.U./lit., 500 μl) was added to start the reaction. The absorption after 20 mins. was $O.D._{610}=0.412$. As a result, a-amylase activity can desirably be measured by this method.

EXAMPLE 76

Assay Method of Amylase using o-chlorophenylmaltopentaoside, 2,6-dibromo-4-aminophenol and Laccase An α, β-mixture of o-chlorophenylmaltopentaoside was dissolved in a 0.05M glycerophosphate buffer (pH 7.0) containing 2% α-cyclodextrin to prepare a 0.4% substrate solution. The substrate solution (2 ml), an enzyme solution (50 μl) containing α-glucosidase (500 u/ml) and β-glucosidase (100 U/ml), 2,6-dibromo-4-aminophenol (5 mM, 50 μl) and laccase (2000 U/ml, 100 μl) were mixed thoroughly in a colorimetric cell and preincubated at 37° C. α-Amylase (Boehringer, 5000 I.U./lit., 500 μl) was added thereto to start the reaction. The absorbency after 20 mins. was measured at 650 nm to obtain $O.D._{650}=0.38$. As a result, α-amylase activity can desirably be assayed by this method.

EXAMPLE 77

Assay Method of α-amylase

A hydroxyl group in maltopentaose is acetylated by a conventional method using sodium acetate and acetic anhydride. The obtained maltopentaose-α-heptadeca acetate, 2,6-dibromophenol and anhydrous zinc chloride were conventionally used to effect a coupling reaction to obtain α- and β-2,6-dibromophenyl hexadeca acetylmaltopentaoside. This product was deacetylated by sodium methoxide in methanol to obtain 2,6-dibromophenylhexadeca maltopentaoside which was dissolved in a 0.05M glycerophosphate buffer (pH 7.0) containing α-cyclodextrin 2% to prepare a 0.4% substrate solution.

The substrate solution (2 ml), an enzyme solution (50 μl) containing α-glucosidase (500 U/ml) and β-glucosidase (100 U/ml), 2,6-dibromo-4-aminophenol (5 mM, 50 μl) and laccase (2000 U/ml, 100 μl) were mixed thoroughly in a colorimetric cell and preincubated at a constant temperature of 37° C. α-Amylase (Boehringer, 5000 I.U./lit., 50 μl) was added thereto start the reaction. The absorbency after 20 mins. was $O.D._{670}=0.387$. As a result, α-amylase can desirably be measured by this method.

EXAMPLE 78

Assay Method of α-amylase

In Example 77, laccase was replaced by ASOD (1310 U/ml) to obtain an absorbency of $O.D._{670}=0.378$. As a result, α-amylase activity can desirably be assayed by this method.

EXAMPLE 79

Assay Method of AlP Using Phenylphosphate and ASOD

Phenylphosphate .2Na (5 mM, 2 ml) dissolved in a 0.1M Tris-HCl buffer (pH 8.0), 2,6-dibromo-4-aminophenol (1 mM, 1 ml) and ASOD (1320 U/ml, 100 μl) obtained from Sechium edule were mixed thoroughly in a colorimetric cell and preincubated at 30° C. AlP (Boehringer, 400 U/0.17 ml, 10 μl) was added thereto to start the reaction, and the changes of absorbency were checked every 5 mins. The results are shown in FIG. 58. AlP activity can be assayed by reacting the liberated phenol from phenylphosphate, ASOD and a coupler.

EXAMPLE 80

Assay Method of AlP 2,6-dibromo phenylphosphate obtained by esterification of a phosphate and 2,6-dibromophenol were dissolved in a 0.1M Tris-HCl buffer (pH 8.0) to prepare a substrate solution (5 mM). This substrate solution (2 ml), 2,6-dibromo-4-aminophenol (1 mM, 1 ml) and laccase (2000 U/ml, 100 μl) were mixed thoroughly in a colorimetric cell and preincubated at 37° C. AlP (Boehringer, 400 U/0.17 ml, 10 μl) was added thereto to start the reaction. The absorbency after 30 mins. was $O.D._{670}=1.253$. AlP can desirably be assayed by this method.

EXAMPLE 81

Assay Method of Esterase Using Phenyl Acetate and ASOD

Phenyl acetate (Tokyo Kasei K.K., 5 mM, 1 ml) dissolved in a 0.1M phosphate buffer (pH 7.0), 2,6-dibromo-4-aminophenol (0.5 mM, 1 ml) and ASOD obtained from Sechium edule (60 U/ml, 20 μl) were mixed thoroughly in a colorimetric cell and preincubated at 30° C. Lipase (Toyo Jozo Co., 2545 U/ml, 100 μl) was added thereto to start the reaction and the changes of absorption every 2 mins. were measured (FIG. 59). As a result, lipase (esterase) can desirably be assayed by reacting the liberated phenol from substrate phenylacetate, ASOD and coupler.

EXAMPLE 82

Assay Method of Bacterial Endotoxin

Boc-Arg($NO_2$)-OH and N,N-diethylamino-p-phenylenediamine were condensed by a water soluble carbodiimide and the protective group removed to prepare H-Arg ($NO_2$)-diethylaminoanilide. Boc-Leu-Gly-ester was de-esterified by an alkali to obtain Boc-Leu-Gly-OH. Both of these products were condensed in butanol by a water soluble carbodiimide to obtain Boc-Leu-Gly-Arg($NO_2$)-diethyl-aminoanilide, which was split at the —$NO_2$ group by palladium catalytic reduction to prepare Boc-Leu-Gly-Arg-diethylaminoanilide. The product was dissolved in a 0.2M Tris-HCl buffer (pH 7.3) containing 0.005M $CaCl_2$ to prepare a substrate solution (2.5 mM). The substrate solution (2 ml), 1-naphthol-2-sulfonate (2 mM, 1 ml) and laccase (2000 U/ml, 100 μl) were mixed thoroughly in a colorimetric cell and preincubated at 37° C. An endotoxin activation enzyme (50 μl) was added thereto to start the reaction. The absorbency at 655 nm was measured ($O.D._{655}=0.268$). As a result, bacterial endotoxin can be assayed by this method. [Preparation of endotoxin activation enzyme]:

Blood lymphocytes (about 100 ml) were collected, carefully avoiding contamination, from Tachypleus tridentatus (about 2 kg weight) (Jap. Pat. Publ. No. 51-40131). Amoebocytes, separated by centrifugation, were washed with 3% aq. NaCl to obtain ameobocyte pellets. A buffer solution (Tris-HCl 0.05M; $CaCl_2$0.001M; NaCl 0.15M; pH 7.2) was added at a ratio of 1/10 v/v of the original blood lymphocytes, and the mixture was stirred thoroughly in a sterilized homogenizer and subjected to freeze-thawing and centrifugation at 50,000 rpm for 15 mins. to obtain the supernatant which was designated Amoebocyte lysate Tachypleus (ALT). This ALT was gel-filtered through Sephadex G-50 (Pharmacia Fine Chem. Co.) according to the method of Young et al. [N. S. Young et al., J. Clin. Invest., 51, 1790 (1972)] to obtain a fraction containing a precursor of amidase, which was treated by endotoxin prepared from Salmonella minesota R595 [M, Niwa et al. Jap. J. Med. Sci. Biol., 26, 20 (1973)] to obtain an endotoxin activation enzyme.

What is claimed is:

[1. A method for assaying a compound of the formula

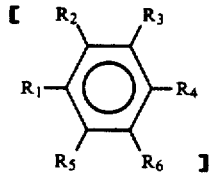

wherein $R_1$ is hydroxyl or amino, or hydrogen if at least one of $R_2$, $R_3$, $R_4$, $R_5$ and $R_6$ is hydroxyl or amino, and $R_2$, $R_3$, $R_4$, $R_5$ and $R_6$ are hydrogen, halogen, lower alkyl, lower alkoxy, amino, substituted amino, hydroxy, carboxyl, or sulfo, or $R_5$ and $R_6$ together form a ring, comprising establishing reaction system containing the compound to be assayed and a coupler and an oxidase that consumes $O_2$ and effects an exzymatic oxidative condensation of said compound to be assayed and said coupler, simultaneously generating a pigment, without the formation of any $H_2O_2$; and measuring a detectable change in said reaction system to assay said compound.]

[2. An assay method according to claim 1, in which $R_1$ is amino, or hydrogen if at least one of $R_2$, $R_3$, $R_4$, $R_5$ and $R_6$ is amino, and $R_2$, $R_3$, $R_4$, $R_5$ and $R_6$ have the same meanings as before, said coupler being a compound of the formula

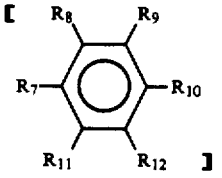

wherein $R_7$ is hydroxyl, amino or substituted amino, and $R_8$, $R_9$, $R_{10}$, $R_{11}$ and $R_{12}$ are hydrogen, halogen, lower alkyl, lower alkoxy, amino, substituted amino, hydroxyl, carboxyl or sulfo, or $R_{11}$ and $R_{12}$ together form a ring.]

[3. An assay method according to claim 1, in which $R_1$ is hydroxyl, or hydrogen if at least one of $R_2$, $R_3$, $R_4$, $R_5$ and $R_6$ is hydroxyl, and $R_2$, $R_3$, $R_4$, $R_5$ and $R_6$ have the same meanings as before, said coupler being a compound of the formula

[ 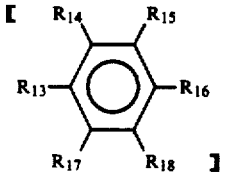 ]

wherein $R_{13}$ is amino or substituted amino, and $R_{14}$, $R_{15}$, $R_{16}$, $R_{17}$ and $R_{18}$ are hydrogen, halogen, lower alkyl, lower alkoxy, amino substituted amino, hydroxyl, carboxyl or sulfo, or $R_{17}$ and $R_{18}$ together form a ring.]

[4. An assay method according to claim 1, wherein said oxidase is an oxidase for an aromatic ring compound having a hydroxyl or amino substituent.]

[5. An assay method according to claim 4, wherein said oxidase is ascorbate oxidase, laccase or tyrosinase.]

[6. An assay method according to claim 1, wherein said detectable change is the amount of consumed oxygen or generated pigment.]

[7. An assay method according to claim 6, and performing said measurement electrochemically.]

[8. An assay method according to claim 7, and performing said measurement by an oxygen electrode.]

[9. An assay method according to claim 6, and performing said measurement of the amount of generated pigment by a colorimetric assay at a specific absorption wavelength thereof.]

[10. An assay method according to claim 1, wherein said compound to be assayed is generated from a synthetic substrate by the action of a hydrolase.]

[11. An assay method according to claim 10, wherein said hydrolase is a peptidase or protease and the synthetic substrate is a compound of the formula

[ 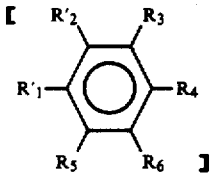 ]

wherein one of $R'_1$ and $R'_2$ is $R_{19}CO—NH—$ and the other is hydrogen, in which $R_{19}CO—$ is an amino acid residue or peptide residue, and $R_3$, $R_4$, $R_5$ and $R_6$ have the same meanings as before.]

[12. An assay method according to claim 10, wherein said hydrolase is glycosidase and the synthetic substrate is a compound of the formula

[ 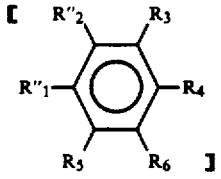 ]

wherein one of $R''_1$ and $R''_2$ is $(S)_n—O—$ and the other is hydrogen, in which S is a monosaccharide unit and n is integer greater than 1, and $R_3$, $R_4$, $R_5$ and $R_6$ have the same meanings as before.]

[13. An assay method according to claim 10, wherein said hydrolase is a phosphatase and the synthetic substrate is a compound of the formula

[ 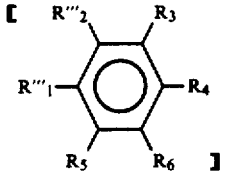 ]

wherein one of $R'''_1$ and $R'''_2$ is

[ 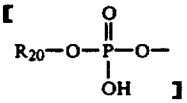 ]

and the other is hydrogen, in which $R_{20}$

[ 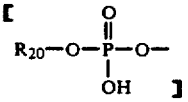 ]

or a substituted or unsubstituted glycerol residue, and $R_3$, $R_4$, $R_5$ and $R_6$ have the same meanings as before.]

[14. An assay method according to claim 10, wherein said hydrolase is an esterase or lipase, and the synthetic substrate is a compound of the formula

[ 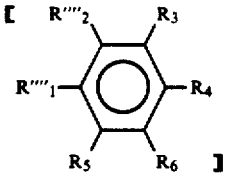 ]

wherein one of $R''''_1$ and $R''''_2$ is $R_{21}CO—O—$ and the other is hydrogen, in which $R_{21}CO—$ is a fatty acid residue, and $R_3$, $R_4$, $R_5$ and $R_6$ have the same meanings as before.]

15. A method for assaying a hydrolase, comprising the steps of: generating from a synthetic substrate by the action of said hydrolase a compound of the formula

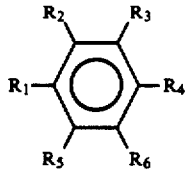

wherein $R_1$ is hydroxyl or amino, or hydrogen if at least one of $R_2$, $R_3$, $R_4$, $R_5$ and $R_6$ is hydroxyl or amino, and $R_2$, $R_3$, $R_4$, $R_5$ and $R_6$ are hydrogen, halogen, lower alkyl, lower alkoxy, amino, substituted amino, hydroxy, [carobxyl] *carboxyl*, or sulfo, or $R_5$ and $R_6$ together form a *fused benzene* ring; establishing a reaction system containing [a] said compound and a coupler and an oxidase that consumes $O_2$ and effects an enzymatic oxidative condensation of said compound and said coupler, simultaneously generating a pigment, without the formation of any $H_2O_2$; measuring a detectable change in said reaction system to assay said compound; and relating the assay of said compound to said hydrolase consumed in generating said compound, thereby to assay said hydrolase.

16. An assay method according to claim 15, wherein the said hydrolase assay is an assay of [piptidase] *peptidase* or protease.

17. An assay method according to claim 15, wherein the said hydrolase assay is an assay of glycosidase.

18. An assay method according to claim 15, wherein the said hydrolase assay is an assay of phosphatase.

19. An assay method according to claim 15, wherein the said hydrolase assay is an assay of esterase or lipase.

*20. An assay method according to claim 15, in which $R_1$ is amino, or hydrogen if at least one of $R_2$, $R_3$, $R_4$, $R_5$ and $R_6$ is amino, and $R_2$, $R_3$, $R_4$, $R_5$ and $R_6$ have the same meanings as before, said coupler being a compound of the formula*

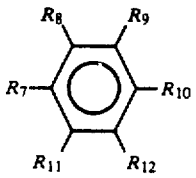

*wherein $R_7$ is hydroxyl, amino or substituted amino, and $R_8$, $R_9$, $R_{10}$, $R_{11}$ and $R_{12}$ are hydrogen, halogen, lower alkyl, lower alkoxy, amino, substituted amino, hydroxyl, carboxyl or sulfo, or $R_{11}$ and $R_{12}$ together form a fused benzene ring.*

*21. An assay method according to claim 15, in which $R_1$ is hydroxyl, or hydrogen if at least one of $R_2$, $R_3$, $R_4$, $R_5$ and $R_6$ is hydroxyl, and $R_2$, $R_3$, $R_4$, $R_5$ and $R_6$ have the same meanings as before, said coupler being a compound of the formula*

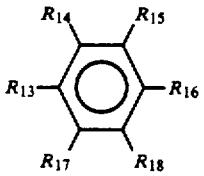

*wherein $R_{13}$ is amino or substituted amino, and $R_{14}$, $R_{15}$, $R_{16}$, $R_{17}$ and $R_{18}$ are hydrogen, halogen, lower alkyl, lower alkoxy, amino, substituted amino, hydroxyl, carboxyl or sulfo, or $R_{17}$ and $R_{18}$ together form a fused benzene ring.*

*22. An assay method according to claim 15, wherein said oxidase is an oxidase for an aromatic ring compound having a hydroxyl or amino substituent.*

*23. An assay method according to claim 22, wherein said oxidase is ascorbate oxidase, lactase or tyrosinase.*

*24. An assay method according to claim 15, wherein said detectable change is the amount of consumed oxygen or generated pigment.*

*25. An assay method according to claim 24, and performing said measurement electrochemically.*

*26. An assay method according to claim 25, and performing said measurement by an oxygen electrode.*

*27. An assay method according to claim 24, and performing said measurement of the amount of generated pigment by a colorimetric assay at a specific absorption wavelength thereof.*

*28. An assay method according to claim 15, wherein said hydrolase is a peptidase or protease and the synthetic substrate is a compound of the formula*

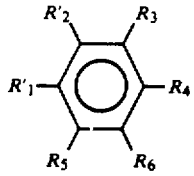

*wherein one of $R'_1$ and $R'_2$ is $R_{19}CO—NH—$ and the other is hydrogen, in which $R_{19}CO—$ is an amino acid residue or peptide residue, and $R_3$, $R_4$, $R_5$ and $R_6$ have the same meanings as before.*

*29. An assay method according to claim 15, wherein said hydrolase is glycosidase and the synthetic substrate is a compound of the formula*

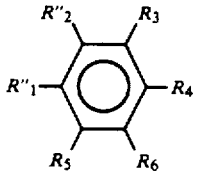

*wherein one of $R''_1$ and $R''_2$ is $(S)_n—O—$ and the other is hydrogen, in which S is a monosaccharide unit and n is integer greater than 1, and $R_3$, $R_4$, $R_5$ and $R_6$ have the same meanings as before, and wherein the linkages between the monosaccharide units and between the monosaccharide unit and the phenyl ring can be hydrolyzed by said glycosidase.*

*30. An assay method according to claim 15, wherein said hydrolase is a phosphatase and the synthetic substrate is a compound of the formula*

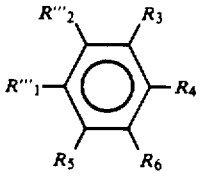

*wherein one of $R'''_1$ and $R'''_2$ is*

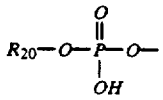

*and the other is hydrogen, in which $R_{20}$ is*

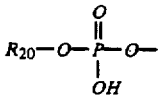

*or a substituted or unsubstituted glycerol residue, and $R_3$, $R_4$, $R_5$ and $R_6$ have the same meanings as before.*

*31. An assay method according to claim 15, wherein said hydrolase is an esterase or lipase, and the synthetic substrate is a compound of the formula*

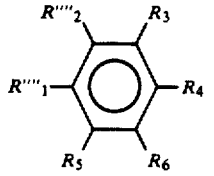

*wherein one of $R''''_1$ and $R''''_2$ is $R_{21}CO—O—$ and the other is hydrogen, in which $R_{21}CO—$ is a fatty acid residue, and $R_3$, $R_4$, $R_5$ and $R_6$ have the same meanings as before.*

* * * * *